(12) United States Patent
Legoupy et al.

(10) Patent No.: US 9,714,261 B2
(45) Date of Patent: Jul. 25, 2017

(54) IONIC LIQUID SUPPORTED ORGANOTIN REAGENTS FOR THE MANUFACTURING OF RADIOPHARMACEUTICALS COMPOUNDS

(71) Applicants: CENTRE NATIONAL DE LA RECHERCHE SCIENTIFIQUE (CNRS), Paris (FR); UNIVERSITE DE NANTES, Nantes (FR); UNIVERSITE D'ANGERS, Angers (FR); UNIVERSITE DU MAINE, Le Mans (FR); INSERM (INSTITUT NATIONAL DE LA SANTE ET DE LA RECHERCHE MEDICALE), Paris (FR); CENTRE HOSPITALIER UNIVERSITAIRE DE NANTES, Nantes (FR)

(72) Inventors: Stephanie Legoupy, Saint Georges sur Loire (FR); Djibril Faye, Eragny sur Oise (FR); Jean-Francois Gestin, Thouare sur Loire (FR); Holisoa Rajerison, Angers (FR); Alain Faivre-Chauvet, Reze (FR); Fabien Boeda, Angers (FR)

(73) Assignees: CENTRE NATIONAL DE LA RECHERCHE SCIENTIFIQUE (CNRS), Paris (FR); UNIVERSITE DE NANTES, Nantes (FR); UNIVERSITE D' ANGERS, Angers (FR); UNIVERSITE DU MAINE, Le Mans (FR); INSERM (INSTITUT NATIONAL DE LA SANTE ET DE LA RECHERCHE MEDICALE), Paris (FR); CENTRE HOSPITALIER UNIVERSITAIRE DE NANTES, Nantes (FR)

( * ) Notice: Subject to any disclaimer, the term of this patent is extended or adjusted under 35 U.S.C. 154(b) by 0 days.

(21) Appl. No.: 15/109,856

(22) PCT Filed: Jan. 7, 2015

(86) PCT No.: PCT/EP2015/050180
§ 371 (c)(1),
(2) Date: Jul. 6, 2016

(87) PCT Pub. No.: WO2015/104300
PCT Pub. Date: Jul. 16, 2015

(65) Prior Publication Data
US 2016/0326194 A1  Nov. 10, 2016

(30) Foreign Application Priority Data
Jan. 7, 2014  (EP) .................... 14150296

(51) Int. Cl.
*C07F 7/22* (2006.01)
*B01J 19/00* (2006.01)
*B01J 19/24* (2006.01)
*C07B 59/00* (2006.01)
*C07C 69/78* (2006.01)
*C07D 207/46* (2006.01)
*C07K 14/765* (2006.01)
*C07K 16/40* (2006.01)

(52) U.S. Cl.
CPC ......... *C07F 7/2212* (2013.01); *B01J 19/0006* (2013.01); *B01J 19/24* (2013.01); *C07B 59/001* (2013.01); *C07B 59/002* (2013.01); *C07B 59/008* (2013.01); *C07C 69/78* (2013.01); *C07D 207/46* (2013.01); *C07K 14/765* (2013.01); *C07K 16/40* (2013.01); *B01J 2219/24* (2013.01); *C07B 2200/05* (2013.01)

(58) Field of Classification Search
CPC .................................................... C07F 7/2212
See application file for complete search history.

(56) References Cited

FOREIGN PATENT DOCUMENTS

WO    9918053 A1    4/1999

OTHER PUBLICATIONS

Vitz et al. "Ionic liquid supported tin reagents for Stille cross coupling reactions" Green Chemistry, 2007, vol. 9, pp. 431-433.*
Pham et al. "Stille Cross-Coupling Reactions with Tin Reagents Supported on Ionic Liquids" European Journal of Organic Chemistry, 2009, pp. 3249-3257.*
Garg et al. "Preparation and preliminary evaluation of 4-[211At]astato-N-piperidinoethyl benzamide." Nuclear Medicine and Biology, vol. 22, No. 4, 1995, pp. 467-473.
Vaidyanathan et al. "A tin precursor for the synthesis of no-carrier-added [*I]MIBG and [211At]MABG." Journal of Labelled Compounds and Radiopharmaceuticals, vol. 50, 2007, pp. 177-182.
Gifford et al. "Polymer-supported organotin reagent for prosthetic group labeling of biological macromolecules with radioiodine." Bioconjugate Chemistry, vol. 22, 2011, pp. 406-412.
Olofsson et al. "High-speed, highly fluorous organic reactions." Journal of Organic Chemistry, vol. 64, 1999, pp. 4539-4541.

(Continued)

Primary Examiner — Joseph Kosack
(74) Attorney, Agent, or Firm — Young & Thompson

(57) ABSTRACT

An ionic liquid supported organotin reagent of formula (I)

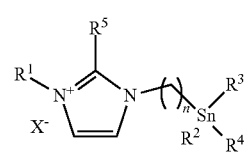

(I)

A process for manufacturing the ionic liquid supported organotin reagent of formula (I), a process for manufacturing an halogenated or radio-halogenated compound using compound of formula (I), a device for implementing the halogenating process and a kit including the compound of formula (I) are also described.

19 Claims, 1 Drawing Sheet

(56) References Cited

OTHER PUBLICATIONS

Fouquet et al. "New monoorganostannanes as efficient reagents for palladium-catalyzed coupling reactions." Journal of Organic Chemistry, vol. 62, 1997, 5242-5243.

Fouquet et al. "Monoalkylstannanes as a new source of allyl radical transfer." Journal of the Chemical Society, Chemical Communications, 1995, 2387-2388.

Pavlinac et al. "Halogenation of organic compounds in ionic liquids." Tetrahedron, vol. 65, 2009, pp. 5625-5662.

Yadav et al. "Efficient halogenation of aromatic systems using N-halosuccinimides in ionic liquids." Advanced Synthesis & Catalysis, vol. 346, 2004, pp. 77-82.

Louaisil et al. "Ionic liquid supported organotin reagents: green tools for stille cross-coupling reactions with brominated substrates." European Journal of Organic Chemistry, 2011, pp. 143-149.

Gosmini et al. "New and simple one-step cobalt-catalyzed preparation of functionalized arylstannanes from the corresponding aryl bromides or iodides." Organic & Biomolecular Chemistry, vol. 3, 2005, pp. 216-217.

Vaidyanathan et al. "A kit method for the high level synthesis of [211At]MABG." Bioorganic & Medicinal Chemistry, vol. 15, 2007, pp. 3430-3436.

Poupon et al. "Removal, recovery, and recycling of triarylphosphonium-supported tin reagents for various organic transformations." Organic Letters, vol. 9, No. 18, 2007, pp. 3591-3594.

Vitz et al. "Ionic liquid supported tin reagents for Stille cross coupling reactions." Green Chemistry, vol. 9, 2007, pp. 431-433.

Pham et al. "Organotin reagents supported on ionic liquid: highly efficient catalytic free radical reduction of alkyl halides." Tetrahedron Letters, vol. 50, 2009, pp. 3780-3782.

Pham et al. "Solvent-free direct reductive amination by catalytic use of an organotin reagent incorporated on an ionic liquid." Chemical Communications, 2009, pp. 6207-6209.

Pham et al. "Stille cross-coupling reactions with tin reagents supported on ionic liquids." European Journal of Organic Chemistry, 2009, pp. 3249-3257.

International Search Report dated Mar. 31, 2015, in corresponding PCT application PCT/EP2015/050180.

European Search Report dated Apr. 24, 2014, in corresponding EP application EP14150296.3.

* cited by examiner

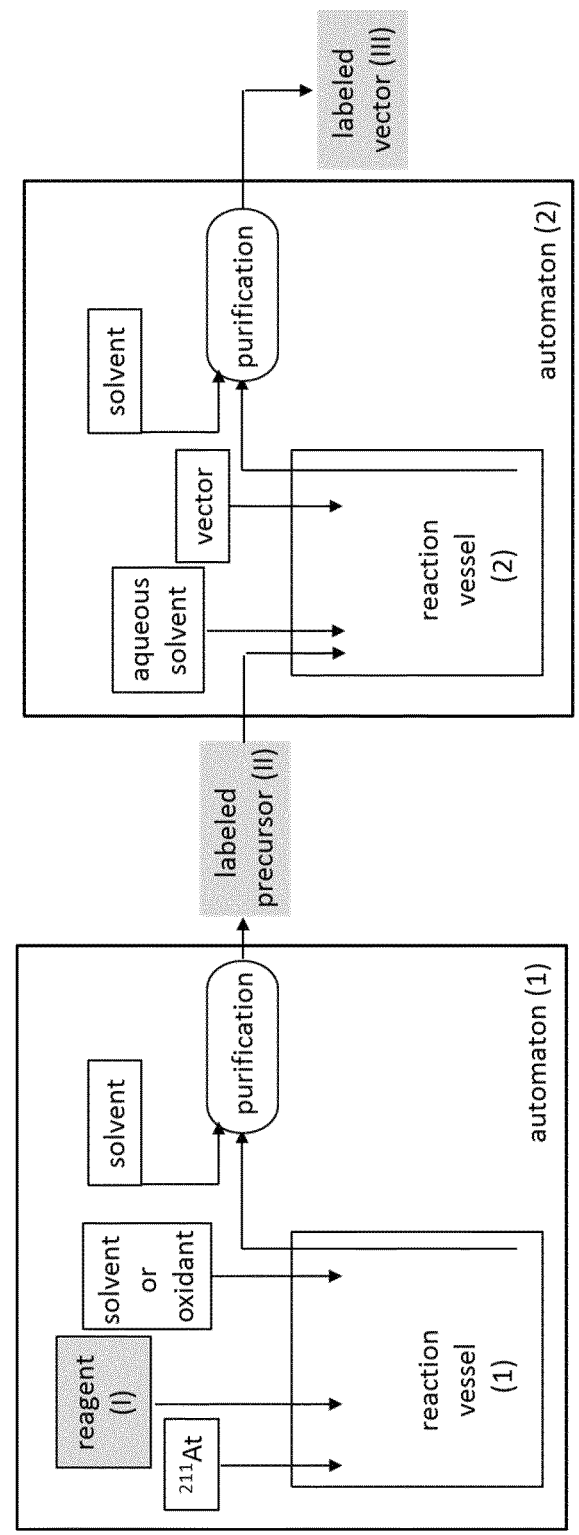

IONIC LIQUID SUPPORTED ORGANOTIN REAGENTS FOR THE MANUFACTURING OF RADIOPHARMACEUTICALS COMPOUNDS

FIELD OF INVENTION

The present invention relates to ionic liquid supported organotin reagents of formula (I)

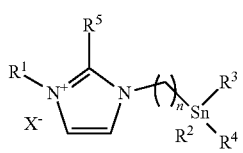

(I)

wherein $X^-$, n, $R^1$, $R^2$, $R^3$, $R^4$ and $R^5$ are as defined below. Especially, $R^4$ represents an aryl or heteroaryl group, said group having vector properties or said group being substituted by at least one reactive function able to react with a vector or said group being substituted by at least one substituent having vector properties.

The invention further relates to a process for manufacturing ionic liquid supported organotin reagents of formula (I). The invention also relates to a labeling process for manufacturing halogenated compounds (II), comprising the use of ionic liquid supported organotin reagents of formula (I):

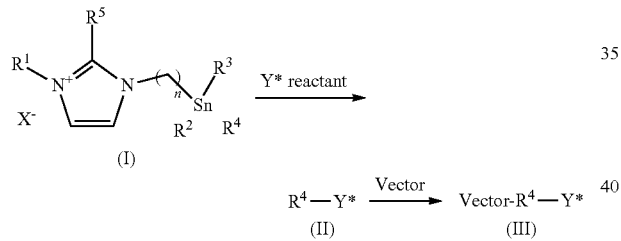

wherein Y* represents a halogen, preferably a radiohalogen

Preferably, the halogen of compounds (II) is a radiohalogen, leading to a radiolabeled compound (II). Radiolabeled compounds (II) obtained by the labeling process of the invention may be used to label vectors, leading to radiopharmaceuticals (III). Another aspect of the invention is a device to implement the labeling process of the invention.

BACKGROUND OF INVENTION

Cancer diseases are among the most important causes of mortality. Radiolabeled drugs, also called radiopharmaceuticals, play an important role in the diagnosis and therapy of cancers. Especially, nuclear medicine is opening new perspectives for diagnostic and functional imaging of tumors, for their characterization (phenotype, proliferation, response to treatment) and that of their environment (vascularization, hypoxia, inflammation, immune response). This characterization of tumors leads to individualized therapeutic strategies. Radiopharmaceuticals are also used in therapy, wherein the vectorization and targeting of radionuclides emitting alpha or beta radiations enables locoregional or systemic therapy.

Radiopharmaceuticals are constituted by two entities: the vector and the radionuclide. Vectors may be peptides, antibodies or organic molecules targeting tumors. Various radionuclides may be used, especially radioactive isotopes of halogens (i.e. radiohalogens), such as for example $^{125}I$ or $^{211}At$. Astatine-211, due to its decay properties (half-life: 7.2 hours; $E_\alpha$: 5.9-7.5 MeV (100%); multiple X-ray emissions 76-92 keV) is considered as one of the most promising radionuclides for the development of targeted alpha-radionuclide therapy.

The labeling of a vector by a radionuclide to form a radiopharmaceutical may be performed either directly or using a labeled precursor comprising a reactive function able to react with a reactive function of the vector. A commonly used labeled precursor for $^{211}At$-labeling of vectors is succinimidyl astatobenzoate (SAB) (scheme 1):

Scheme 1. $^{211}At$-labeling of vectors using succinimidyl astatobenzoate (SAB).

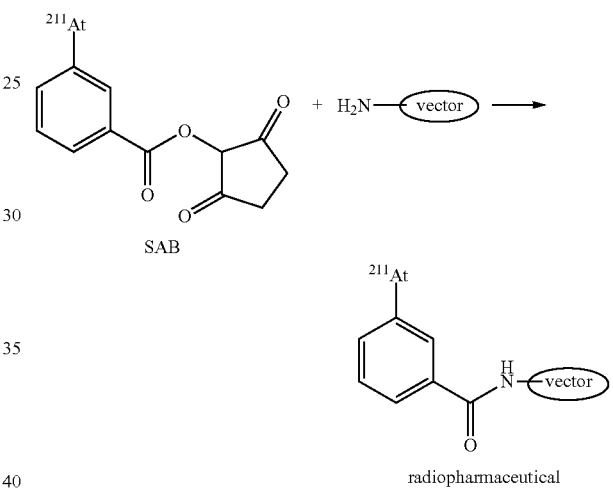

Among methods enabling the introduction of a radiohalogen, especially $^{211}At$, halodemetallation reaction of an organometallic compound with an electrophilic species is commonly used (scheme 2):

Scheme 2. Halodemetallation reaction of an organometallic compound.

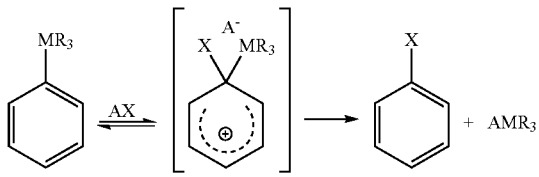

Due to the high reactivity of the carbon-metal bound, the halodemetallation reaction occurs quickly in mild conditions. The rapidity of the reaction enables radiolabeling compounds with radionuclides having short half-lives while providing high specific activities.

Among organometallic compounds suitable for halodemetallation reaction, organotin derivatives are the most interesting due to the weakness of the carbon-tin bond, making of the tin group a good leaving group. Moreover, tin precursors are easily accessible by conventional synthesis methods from a broad variety of compounds. Especially, commonly used processes of labeling with radiohalogens involve tin(IV) derivatives such as tributyl tin or trimethyl tin (Garg et al., Nucl. Med. Biol., 1995, 22(4), 467-473; Vaidyanathan et al., J. Label. Compd Radiopharm., 2007, 50, 177-182). However, the use of this kind of tin derivatives releases by-products difficult to separate from products of interest leading to low chemical and radiochemical purities and decrease of coupling yields.

Moreover, organotin compounds are known to have an important cellular toxicity. Therefore, any contamination by stannic by-products should be avoided when compounds are dedicated to pharmaceutical or veterinary applications. For these reasons, procedures involving usual tin derivatives are excluded in industrial synthesis of pharmaceutical compounds, despite their synthetic interest.

Solid supported tin reagents have been developed to easily eliminate tin reagents excess from the product of interest and to overcome tin contamination (WO99/18053; Gifford et al., Bioconj. Chem., 2011, 22, 406-412). To the knowledge of the Applicant, the sole example of radiolabeling with [211]At using a solid supported organotin reagent was reported by Vaidyanathan et al. for the synthesis of [211]At-MABG (meta-[211]At]Astatobenzylguanidine) (Vaidyanathan et al., Bioorg. Med. Chem., 2007, 15, 3430-3436):

Scheme 3. [211]At-radiolabeling using a solid supported organotin reagent.

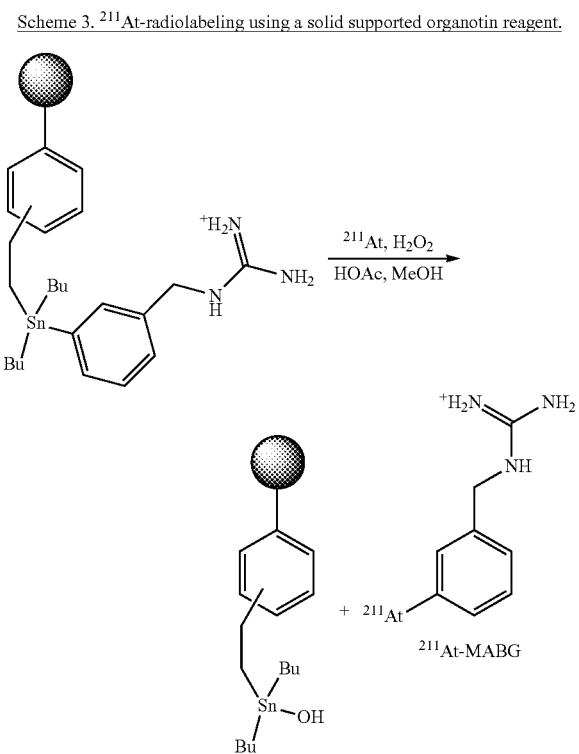

The synthesis of [211]At-MABG was achieved with acceptable yields and good purity (<1 ppm of tin). However, the duration of reaction was quite long and reactivity on solid support was not optimum. Moreover, when using solid supported reagents, it is difficult to automatize the process of synthesis, whereas it is of common practice in radiolabeling processes. Indeed, automatization enables manipulators protection from radiations. Moreover, it accelerates the handling and thus provides higher specific activities and is well-suited to GMP process.

Other attempts have been done recently to overcome tin contamination problems, leading for example to the use of phosphonium grafted organotin (Poupon, et al. Org. Lett. 2007, 9, 3591) and other modified organotin reagents (Olofsson et al. J. Org. Chem. 1999, 64, 4539; Fouquet et al. J. Org. Chem. 1997, 62, 5242; Fouquet et al. J. Chem. Soc. Chem. Comm. 1995, 2387).

There is thus a need for new organotin reagents suitable for halodemetallation reaction to provide radiolabeled compounds with high specific activities and with limited, if any, tin contamination.

In the field of supported reagents, ionic liquids were proposed to replace solid supports. Ionic liquids are onium salts, constituted by the association of an anion and a cation, at least one of which being organic, said onium salts having a melting point below 100° C. The more commonly used ionic liquids have a cation structure centered on nitrogen (tetraalkylammonium, alkylpyridinium, alkylimidazolium), phosphorus (phosphonium), sulfur (sulfonium), 1,4-diazoniabicyclo[2.2.2]octane, sulfethanammonium, prolinium, pyrrolidinium. A large diversity of anions may be used, such as for example halide, acetate, trifluoroacetate, triflate, alkylsulfate, sulfonate, tetrafluoroborate, tetraarylborate, hexafluorophosphate, nitrate, hexafluoroantimonate, prolinate, hydroxide, hydrogen sulfate, tetrachloroferrate, aluminum tetrachloride, perfluorobutylsulfonate, p-toluenesulfonate, formiate, dihydrogen phosphate. The simplest method to exchange the anion of an ionic liquid is ionic metathesis.

As for solid-supported reagents, ionic liquid supported reagents enable simple separation and purification at the end of the reaction, such as for example by filtration on silica, by distillation or by extraction. As for non-supported reagents, ionic liquid supported reagents enable conducting reactions in homogeneous conditions and therefore improve reactivity. Therefore, ionic liquid supported reagents have the advantage to play a dual role of support and solvent. Moreover, in the particular case of a halodemetallation reaction wherein an electrophilic radiohalogen species should be used, the ionic liquid can act as a catalyst for its formation or can enhance its reactivity (Pavlinac et al., Tetrahedron 2009, 65, 5625-5662; Yadav et al., Adv. Synth. Catal. 2004, 346, 77-82).

The Applicant proved the interest of ionic liquid supported organotin reagents for Stille cross coupling reaction, catalytic free radical reduction of alkyl halides and for solvent-free reductive amination (Vitz et al., Green Chem., 2007, 9, 431-433; Louaisil et al., Eur. J. Org. Chem., 2011, 143-149; Pham et al., Chem. Comm., 2009, 6207-6209; Pham et al., Tet. Lett., 2009, 3780-3782). However, to the knowledge of the Applicant, ionic liquid supported organotin reagents have never been used in halodemetallation reaction and even less using radiohalogens.

Considering the potential advantages of ionic liquid supported organotin reagents, the Applicant focused on providing ionic liquid supported organotin reagents suitable for halogenation reaction, especially for the synthesis of "tin free" radiohalogenated compounds. Especially, the Applicant intended providing ionic liquid supported organotin reagents of following formula (I):

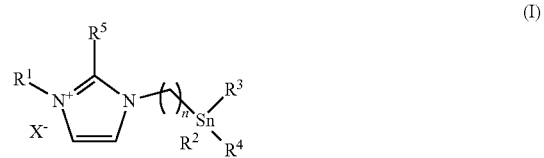

wherein $X^-$, n, $R^1$, $R^2$, $R^3$, $R^4$ and $R^5$ are as defined below. Especially, $R^4$ represents an aryl or heteroaryl group, said group having vector properties, or said group being substituted by at least one reactive function able to react with a vector or said group being substituted by at least one substituent having vector properties.

Moreover, it was intended to provide a method of manufacturing of such ionic liquid supported organotin reagents being a reproducible method and a versatile method, adaptable to a large variety of substrates with various reactive functions or vector properties.

A method described in the prior art to prepare ionic liquid supported organotin reagents involves a reaction between the stannylchloride function in the side chain of an ionic liquid with a Grignard reagent (Scheme 4—Louaisil et al., Eur. J. Org. Chem., 2011, 143-149):

Scheme 4. Substitution reaction by a Grignard reagent.

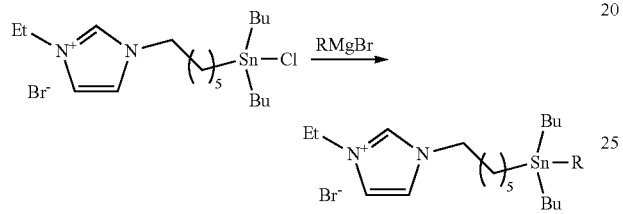

In the case of ionic liquid supported organotin reagents of formula (I) wherein $R^4$ is substituted by at least one substituent having vector properties, such bioactive substituents are sensible to degradation. Therefore, harsh Grignard conditions are not suitable for such case.

Another method described in the prior art to prepare ionic liquid supported organotin reagents involves a substitution reaction of an halogen atom in the side chain of a precursor of an ionic liquid, by a stannyllithium derivative (Scheme 5—Vitz et al., Green Chem., 2007, 9, 431-433).

Scheme 5. Substitution reaction by a stannyllithium derivative.

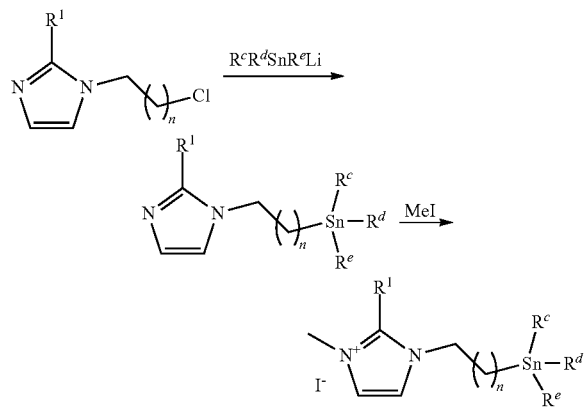

Despite various attempts, above method did not enabled to obtain ionic liquid supported organotin reagents of formula (I) comprising a reactive function. Moreover, the use of very reactive lithium derivatives is not compatible in the case of ionic liquid supported organotin reagents comprising bioactive substituents, which are sensible to degradation.

The Applicant also attempted to adapt method of scheme 5 to prepare ionic liquid supported organotin reagents bearing a reactive function by substituting the halogen atom on an stannylchloride ionic liquid by an aryllithium reactant (Scheme 6).

Scheme 6. Ineffective substitution reaction by an aryllithium.

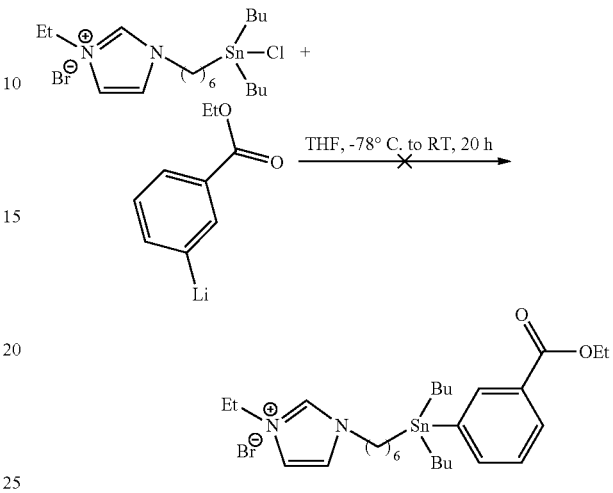

However, the Applicant showed that the substitution by an aryllithium of a stannylchloride derivative of ionic liquid does not provide an ionic liquid supported organotin reagent comprising a reactive function. Especially, this was evidenced with the reaction reported in scheme 6, wherein none of the expected compound was obtained, while unreactive ionic liquid only was recovered after purification.

Therefore, mere transposition of what was known with ionic liquid as support of organotin reagents is not sufficient to provide ionic liquid supported organotin reagents comprising a reactive function.

Gosmini et al. described a cobalt-catalyzed preparation of non-supported functionalized arylstannanes (Gosmini et Périchon, Org. Biomol. Chem., 2005, 3, 216-217). Especially, the following reaction was described:

Scheme 7. Cobalt-catalyzed preparation of non-supported functionalized arylstannanes.

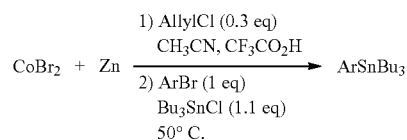

Ar = aryl group comprising a reactive functional substituent

Gosmini conditions comprise a first step of activation of zinc dust and cobalt bromide in presence of allylchloride and trifluoroacetic acid in acetonitrile. Then, arylstannane derivatives are obtained in a one-pot reaction from arylbromides or iodide, in presence of tributylstannylchloride, through the passage to the arylzinc derivative.

The mere transposition of above conditions of Gosmini to stannyl chloride ionic liquid did not enable to obtain expected compounds, even less ionic liquid supported organotin reagents comprising a reactive function. Even with some modifications of the conditions, such as varying the number of equivalents or the temperature of reaction, expected compounds have not been isolated.

An important research work was thus conducted to systematically explore all the parameters of the reaction. Especially, it enabled highlighting that very fine zinc dust should be used and carefully activated before use. Besides, the Applicant evidenced that conducting the reaction in presence of dibromoethane enabled to obtain expected compounds in a reproducible manner, even for ionic liquid comprising a reactive function.

Therefore, the present invention provides ionic liquid supported reagents of formula (I) and a reproducible and versatile process for their preparation.

Reagents of formula (I) of the invention may be used in a halodemetallation reaction, leading to halogenated compounds (II), preferably radiohalogenated compounds, as described in scheme 8.

Scheme 8. General scheme for halodemetallation reaction on reagent (I) leading to halogenated compound (II).

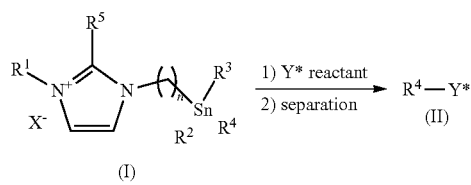

wherein Y* represents a halogen, preferably a radiohalogen

In one embodiment, in compound (II) Y* is preferably a radiohalogen, and compound (II) may react with a biological vector, such as for example an antibody, a peptide or an organic molecule, to provide a radiopharmaceutical (III) useful in nuclear medicine (scheme 9).

Scheme 9. General synthesis of radiopharmaceutical (III) using compound (II).

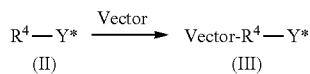

In a specific embodiment, compounds (I) of the invention are of formula (I'''a) and react according to scheme 10 to afford intermediate compound (II'''a) bearing a reactive function A able to react with the reactive function B of a vector, leading to radiopharmaceutical of formula (III'''a).

Scheme 10. Halo-labeling using the ionic liquid supported organotin reagent (I'''a), wherein A and B represent reactive functions and L represents a linker.

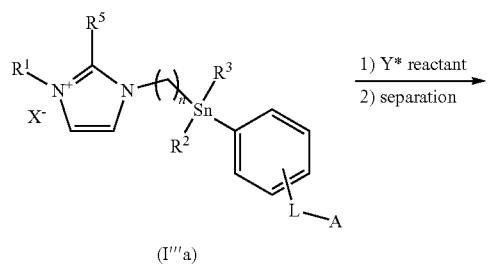

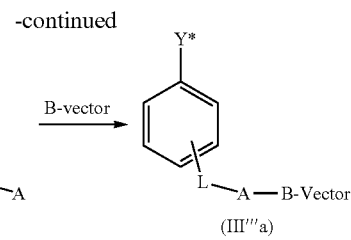

Conditions of radiolabeling with radiohalogen described in the art did not provided expected results. Therefore, an important research work was necessary to determine suitable radiolabeling conditions. The invention thus further relates to a radiolabeling process comprising the reaction of the ionic liquid supported organotin reagent of the invention with a radiohalogen.

The labeled compound (II) may be a radiolabeled vector or can react with a vector, such as an antibody, a peptide or an organic molecule, to provide a radiopharmaceutical (III) useful in nuclear medicine (scheme 9). Reactive function A of the labeled compound (II) and reactive function B of the vector are reactive functions compatible together to form a bound between the labeled compound (II) and the vector, such as for example amine and carboxylic functions leading to an amide bound.

Thanks to the use of the ionic liquid supported reagents of the invention, the purification of the labeled compound (II) may be easily performed in good yields, for example by a filtration on silica gel, distillation or extraction.

Radiolabeling processes are usually performed on automated devices to avoid manipulators irradiation and/or contamination. Moreover, automated devices enable to reduce the time of manufacturing to obtain more important specific activities. Syntheses using ionic liquid supported reagents are performed in homogeneous conditions and with purification methods which present the advantage to be compatible with automated devices. Reactions using non-supported reagents can be automated but require complex, time-consuming and costly systems wherein chromatographic purification unit must be included. Reactions using solid supported reagents require batch process to change the solid substrate.

The Applicant demonstrated that the covalent binding of organotin derivatives on the ionic liquid supported reagents (I) of the invention enables limiting, if any, toxic release of tin when these reagents are used in halodemetallation reactions. Especially, the residual quantity of tin is inferior to 6 ppm, preferably inferior to 3 ppm, in the halogenated compounds obtained using reagents (I) of the invention. Consequently, the tin contamination rate of halogenated products is compatible with pharmaceutical or veterinary applications without further purification as the amount of tin therein is very low. Moreover, as release of tin is avoided, it reduces the environmental impact of the process.

The use of ionic liquid as support instead of solid support also enables to increase the rate of reaction, especially due to a better reactivity in homogeneous medium compared to heterogeneous medium. Increasing the rate of reaction was preponderant more particularly for short half-life radionuclides and leads advantageously to higher specific activities for radiolabeled compounds. Moreover, the use of reagents supported on ionic liquids also opens the possibility to combine effective and fast purifications to innovative automation systems including microfluidic devices.

Therefore, with the ionic liquid supported organotin reagents (I) of the present invention, reactions occur quickly and purification is performed by simple filtration. Radiolabeled compounds with a higher specific activity may thus be obtained. This rapidity of synthesis and purification is all the more important with radionuclides with short half-lives, especially for the 7.2 hours of $^{211}$At.

The ionic liquid supported organotin reagents of the invention display the following further advantages:
- residual derivatives obtained after halogenation reaction and isolation of compounds (II) may be recycled;
- ionic liquid supported organotin reagents (I) and residual derivatives obtained after halogenation reaction and isolation of compounds (II) are odorless and stable at room temperature.

Therefore, the use of the ionic liquid supported organotin reagents (I) of the invention in the halogenation process of the invention enables the manufacturing of radiolabeled compounds (II) and (III) having a high specific activity, without contamination by tin, for preclinical and/or clinical applications, either in pharmaceutical or veterinary uses.

DEFINITIONS

In the present invention, the following terms have the following meanings:

"Activated ester" refers to esters in which the alkoxy group is an electron-withdrawing group, preferably OCH$_2$CN, OCH=CH$_2$, OPip, O3Py, ONp, OTcp, OPcp, O-tetrafluorophenyl, OPfp, O-nitrophenyl, OSu (succinimidyl), sulfosuccinimidyl, ONPhth, ODhbt, OBt. These groups are represented in the scheme below:

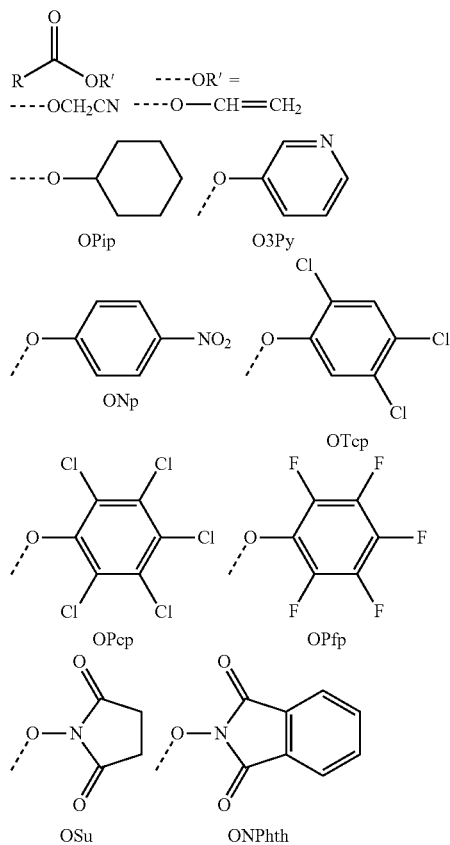

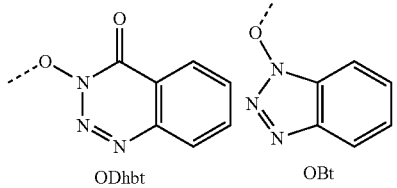

"alkenyl" refers to any linear or branched hydrocarbon chain having at least one double bond, of 2 to 12 carbon atoms, and preferably 2 to 6 carbon atoms.

"alkyl" refers to any saturated linear, cyclic or branched hydrocarbon chain, with 1 to 12 carbon atoms, preferably 1 to 6 carbon atoms, and more preferably methyl, ethyl, propyl, isopropyl, n-butyl, sec-butyl, isobutyl and tert-butyl.

"alkynyl" refers to any linear or branched hydrocarbon chain having at least one triple bond, of 2 to 12 carbon atoms, and preferably 2 to 6 carbon atoms. Non limiting examples of alkynyl groups are ethynyl, 2-propynyl, 2-butynyl, 3-butynyl, 2-pentynyl and its isomers, 2-hexynyl and its isomers—and the like.

"amine" or "primary amine" refers to the group —NH$_2$. "secondary amine" refers to the group —NHR wherein R is different from H, preferably an alkyl group; "tertiary amine" refers to the group —NRR' wherein R and R' are different from H, preferably represent alkyl groups.

"antibody" (Ab) as used herein includes monoclonal antibodies (mAb), polyclonal antibodies, multispecific antibodies (e.g., bispecific antibodies), and antibody fragments, so long as they exhibit the desired biological activity. An "antibody fragment" comprises a portion of an intact antibody, preferably the antigen binding or variable region of the intact antibody. Examples of antibody fragments include Fab, Fab', F(ab')2, and Fv fragments; diabodies; linear antibodies (see U.S. Pat. No. 5,641,870; Zapata et al., Protein Eng. 8(10): 1057-1062 [1995]); single-chain antibody molecules, especially single-chain variable fragment (scFv); and multispecific antibodies formed from antibody fragments.

"aryl" refers to a mono- or polycyclic system of 5 to 20, and preferably 6 to 12, carbon atoms having a single ring (i.e. phenyl) or multiple aromatic rings fused together (e.g. naphtyl) or linked covalently, wherein at least one ring is aromatic. The aromatic ring may optionally include one to two additional rings (either cycloalkyl, heterocyclyl or heteroaryl) fused thereto. Non-limiting examples of aryl comprise phenyl, biphenylyl, biphenylenyl, naphthalen-1- or -2-yl, binaphthyl indenyl, acenaphtylenyl, acenaphtenyl, phenanthryl, pentalenyl, indanyl, tetrahydronaphtyl, dihydronaphthyl, pyrenyl. The aryl group can be substituted by one or more substituents chosen independently of one another, among a hydroxyl group; a linear, cyclic or branched alkyl group comprising 1, 2, 3, 4, 5 or 6 carbon atoms, in particular methyl, ethyl, propyl, butyl; an alkoxy group; a halogen atom, in particular bromine, chlorine and iodine; a nitro group; a cyano group; an azido group; an aldehyde group; a boronato group; a phenyl; CF$_3$; methylenedioxy; ethylenedioxy; SO$_2$NRR', NRR', COOR wherein R and R' are each independently selected from the group consisting of H, alkyl, cycloalkyl, alkenyl, cycloalkenyl, alkynyl, cycloalkynyl and aryl; a second aryl group which may be substituted as recited above.

"azidoalkyl" refers to the general term of alkyl, comprising cycloalkyl and heterocyclyl groups as herein defined, bearing the azido function, commonly represented as R—$N_3$.

"azidoaryl" refers to the general term of aryl, comprising heteroaryl groups, as herein defined, bearing the azido function, commonly represented as Ar—$N_3$.

"bioactive group" or "vector" refers to a molecule being able to recognize a biological target tissue (depending on the pathology to be treated or detected). Preferably, "bioactive group" or "vector" refers to biomolecules, organic compounds or nanocarriers. By "biomolecules", it is understood an antibody or fragments thereof or any antibody construct (like minibodies or diabodies, resulting from antibody engineering) as well as recombinant proteins or synthetic peptides selected to bind target cells (e.g., but not limited to, affibodies). By "organic compounds" it is referred to organic compounds binding cells, or organic compounds transported by transporters expressed by cells (e.g., but not limited to, glucose, amino-acids, biogenic amines), peptides binding specific receptors (e.g. but not limited to somatostatine, cholecystokinine, neurotensine receptors), aptamers, haptens, drugs. In a specific embodiment, "vector" refers to a small organic molecule. Especially, this term may refer, but is not limited to biotin, benzylguanidine, dihydroxyphenylalanine and theirs derivatives. By "nanocarrier" it is referred to compound able to recognize the target cells such as a nanocapsule, a liposome, a dendrimer or a carbon nanotube. These nanocarriers may be linked if necessary to tumor specific ligands.

Bioactive groups and biological targets of interest are illustrated by the non-limiting examples below:

| Bioactive group type | Biological target | Bioactive group family | Examples of bioactive group |
| --- | --- | --- | --- |
| mAb | protein CAIX | Anti CAIX | Cg250 |
| mAb | CTLA-4 | Anti CTLA-4 | Ipilimumab |
| saccharide | TRL4 | | LPS (lipopolysaccharide) |
| peptide | alphavbeta3 integrin | RGD peptides | Cyclo-RGD (GAERTNER, Eur. J. Nucl. Med, 2012), RGD tetramer (CHENG, Eur J. Nucl. Med, 2011) |
| Ab | TNF-α | anti-TNF-α antibody | |
| peptide | somatostatin receptors | somatostatin analogs | OCTREOTIDE, octreotate, 1-Nal$^3$-octreotide (NOC), lanreotide, p-Cl-Phe-cyclo(D-Cys-Tyr-D-Aph(Cbm)-Lys-Thr-Cys)D-Tyr-$NH_2$ (LM3), p-$NO_2$-Phe-cyclo(D-Cys-Tyr-D-Aph(Cbm)-Lys-Thr-Cys)D-Tyr-$NH_2$ (JR10), Cpa-cyclo(D-Cys-Tyr-D-Aph(Cbm)-Lys-Thr-Cys)D-Tyr-$NH_2$, pansomatostatin |
| peptide | gastrin-releasing peptide (GRP) receptors | Bombesin, derivatives and analogs of bombesin | PEG4-Bombesin (D. WILD, Canc. Res., 2011; S. DäPP, Eur J Nucl Med, 2012), Bombesin, -[D-Tyr$^6$, βAla$^{11}$, Thi$^{13}$, Nle$^{14}$]bombesin, $PEG_2$-[D-Tyr$^6$, βAla$^{11}$, Thi$^{13}$, Nle$^{14}$]bombesin, -4-amino-1-carboxymethyl-piperidine-D-Phe-Gln-Trp-Ala-Val-Gly-His-Sta-Leu-$NH_2$, D-Phe-Gln-Trp-Ala-Val-Gly-His-Sta-Leu-$NH_2$, RGD-BBN |
| peptide | neuropeptide Y receptors | neuropeptide Y and analogs | |
| peptide | vasoactive intestinal peptide receptor (VPAC-1) | vasoactive intestinal and analogs | |
| peptide | cholecystokinin 2 receptors (CCK) | CCK analogs | CCK-8, minigastrin |
| peptide | neurokinin-1 receptor | Neurokinin-1 analogs | |
| peptide | melanocortin-1 receptor | α-MSH analogs | Ser-Tyr-Ser-Met-Glu-His-Phe-Arg-Trp-Gly-Lys-Pro-Val (H. Guo, J. Nucl Med, 2010) |
| small molecules | melanocortin-1 receptor | α-MSH analogs | benzamides derivatives (A. Maisonial, J Med Chem, 2011, Eur J Med Chem, 2013) |
| peptide | chemokine receptor 4 (CXCR4) | Chemokine analogs | Gourni; J. Nucl. Med, 2011, 52, 1803: SDF1-alpha, FC131 and analogues, T140 and analogs |

-continued

| Bioactive group type | Biological target | Bioactive group family | Examples of bioactive group |
|---|---|---|---|
| peptide | neurotensin (NT) receptor | Neurotensin, and analogs | |
| small molecule | neurotensin (NT) receptor | neurotensin and analogs | |
| peptide | | insulin and analogs | (M. Contino et al., Advances in Alzheimer's Disease 2 (2013) 13-30) |
| Monobody | IGF-R | Anti-IGF-R | |
| mAb | IGF-R | Anti-IGF-R | R1507 |
| peptide | P-gp | P-gp ligands | |
| mAb | CD20 | Anti CD20 | Tositumomab (BEXXAR), ibritumumab tiuxetan (Zevalin) Rituximab, Ofatumumab |
| mAb | CD22 | Anti-CD22 | epratuzumab |
| mAb | CD33 | Anti-CD33 | gemtuzumab |
| mAb | CD52 | Anti-CD52 | Alemtuzumab |
| mAb | CD44-v6 | Anti- CD44-v6 | U36 |
| mAb | CD105 | Anti-CD105 | TCR105 |
| mAb | CD30 | Anti-CD30 | Brentuximab vedotin (Adcetris) |
| peptide | $\alpha 2\beta 1$ integrin | | Asp-Gly-Glu-Ala (DGEA) peptide |
| steroid | estrogen receptor | estrogen analogs | Estradiol radiolabelling (Academic Radiology, 14, 9, 2007, 1050) |
| mAb | CD164 | Anti-CD164 | 103B2/9E10, N6B6, 67D2, 105A5 (doi: 10.4049/jimmunol. 165.2.840); |
| steroid | progesterone receptors | progestin analogs | 16alpha, 17alpha-dioxolane progestin analogs (J Med Chem. 2006 Jul. 27; 49(15): 4737-44.) |
| mAb | Beta-amyloid | Anti- Beta-amyloid | 11- 1F4; WO2014/089500, Aducanumab (imaging) (coupe) |
| peptide | Beta-amyloid | Beta-amyloid binding | ANA-1, ANA-5 and analogs |
| mAb | FCGR2A | Anti-FCGR2A (Anti-CD32) | 3E8; |
| Small molecule | Porphyrin (biosynthesis precursor of) | Porphyrin precursor | 5-aminolevulinic acid hydrochloride |
| Small molecule | beta-sheet proteins | derivatives of thioflavin-T (ThT) | benzothiazole derivatives (WO2010/053218) |
| mAb | GPA33 | Anti-GPA33 | A33, KRN330 (Investigational New Drugs, August 2014, Volume 32, Issue 4, pp 682-690) |
| Small molecule | neuronal nicotinic acetylcholine receptor (nAChR) | alpha-7 nicotinic receptor binding ligands | A-84543 (3-[(1-methyl-2(S)-pyrrolidinyl)methoxy]pyridine), AFDB-02 (Synthesis and Evaluation of New Analogs of A-84543 as Nicotinic Acetylcholine Receptor Ligands by Ogunjirin, Adebowale E., Ph.D., HOWARD UNIVERSITY, 2011, 112 pages; 3460685), 2-pyrrolidinyloxy-substituted pyridines, Nicotin, epibatidine, RJR-2403, SIB-1508Y, ABT-418, A85380 and derivatives (WO2005/000806); azetidinylmethoxypyridine derivatives |
| affibody | HER-2 | Anti-HER-2 | ZHER2: 342 (J Nucl Med 2009; 50: 417-425), ZHER2: 2891, ZHER2: 2395, ZHER2: 2891-ABD035 and derivatives (J Nucl Med. 2010; 51: 1131-1138; J Nucl Med. 2013 June; 54(6): 961-8.), ABY-025, ABY-028 and derivatives |
| mAb | HER-2 | Anti-HER-2 | Trastuzumab |
| Small molecules | | piperidines | N-methylpiperidin-4-yl acetate, N-methylpiperidin-4-yl propionate |
| Small molecules | Cholinesterase (inhibitor) | anticholinesterase | Galantamine; molecules in Mol. BioSyst., 2013, 9, 792-805 |
| Small molecules | c-Met (tyrosine-kinase receptor) | Tyrosine kinase inhibitor (TK) | AH113804 |

-continued

| Bioactive group type | Biological target | Bioactive group family | Examples of bioactive group |
|---|---|---|---|
| Small molecules | | Tyrosine kinase inhibitor (TKI) | Erlotinib, sorafenib, Imatinib, dasatinib, nilotinib, pazobanib, vandetanin, vemurafenib, crizotinib |
| mAb | cMet | Anti-cMet | DN30 |
| mAb | vegf | Anti-vegf antibodies | Bevacizumab WO2005/000900 |
| Monobodies (adnectin) | vegfr | Vegfr2 antagonist | pegdinetanib |
| hormon | | androgen receptor modulators | |
| mAb | egfr | anti-egfr | Cetuximab, panitumumab, L19-SIP, |
| monobody | egfr | anti-egfr | |
| protein | Annexin A2 | Annexin A2 ligands | |
| protein | Annexin V | Annexin ligand | Annexin V (The scientific World Journal, 2014, Kazuma Ogawa) |
| scFV | ED-B-fibronectin | anti-ED-B-fibronectin | |
| mAb | ED-B-fibronectin | anti-ED-B-fibronectin | L19-SIP |
| minibody | PSMA | Anti-PSMA | HuJ591 minibody |
| mAb | PSMA | Anti-PSMA | J591, WO2011/069019, 7E11 |
| diabodies | PSMA | Anti-PSMA | WO2011/069019 |
| Small molecule | psma | Psma ligand | 2-(3-{1-carboxy-5-[(6-[F]fluoro-pyridine-3-carbonyl)-amino]-pentyl}-ureido)-pentanedioic acid, 2-(3-{1-carboxy-5-[pyridine-3-carbonyl)-amino]-pentyl}-ureido)-pentanedioic acid |
| mAb | MCSP | antimelanoma antibodies | |
| Small molecule | folate receptor | Folate receptor ligand | Folate and folate derivatives |
| mAb | folate receptor alpha | Anti-folate receptor alpha | FARLETUZUMAB (MORAb-003) |
| Small molecule | Bones | Bone mineralisation | Phosphonates family |
| Small molecule | PD1 | PD1 receptor | PD1 ligand |
| mAb | PD1 | PD1 receptor | PD1 ligand (Onco target and therapy, M. Lagreca, 2014, p 1115) |
| mAb, Fab' | CEA | Anti-CEA | IMMU-4, arcitumomab, M5A, T84, 2A3, 2A3-mFc, 9A6 (Journal of Controlled Release, May 2012; 161(1): 18-24.); WO 2012/040824 |
| scFv | CEACAM1 | Anti-CEACAM1 | DIATHIS1 |
| mAb | endosialin | | ONTUXIZUMAB (MORAb-004) |
| chimeric IgG$_1$ antibody | mesothelin | Anti-mesothelin | AMATUXIMAB (MORAb-009) |
| mAb | GM3 | Anti-GM3 | MORAb-050 |
| mAB | GD3 | Anti-GD3 | |
| mAb | Tissue Factor | Anti-TF | MORAb-066 |
| Small molecule | Endothelin receptor | Endothelin receptor ligand (antagonist) | Atrasentan |
| Small molecule | Amyloid beta | Amyloid beta binding | AZD-2995; AZD-2184; AZD-4694, AZPET |
| mAb | LewisY carbohydrate antigen | Anti- Lewis Y carbohydrate antigen | B3 |
| oligonucleotide | CDK | antisense oligonucleotide CDK inhibitor | |
| mAb or fragments | tau | Human anti-tau antibodies) | WO2014/100600 |
| Ab | notch3 | Anti-notch3 antibodies | WO2014/100435 |
| Small molecule | Lenalidomide and analogs | | lenalidomide |
| mAb | CD38 | Anti-CD38 Antibodies | |
| mAb | CD138 | Anti-CD138 Antibodies | BB4, 9E7 |

-continued

| Bioactive group type | Biological target | Bioactive group family | Examples of bioactive group |
|---|---|---|---|
| hapten | | hapten | In-DTPA, peptide or heteropeptide containing the "Histidyl-succinimidyl-glycyl" sequence |
| Biotin | Biotin | Biotin | biotin |
| Multispecific and/or multivalents antibodies | | | defined and obtained as described in WO03/057829, WO2013/005194, WO2011/069104, WO2013/005194, WO2010/108127, WO2014/081954, WO2014/144280, CN103694354, US2014/213771, WO2011/131746, US2009/182127, WO2014/082179 |
| Multispecific complexes | | | such as described in WO2014/144600, WO2014/096015 |

"cycloalkyl" refers to a cyclic or polycyclic alkyl group, optionally branched, such as for cyclopropyle, cyclopentyle or cyclohexyle.

"cycloalkenyl" refers to a cyclic or polycyclic alkenyl group, optionally branched.

"cycloalkynyl" refers to a cyclic or polycyclic alkynyl group, optionally branched.

"heteroaryl" refers to 5 to 12 carbon-atom aromatic rings or ring systems containing 1 to 2 rings which are fused together or linked covalently, typically containing 5 to 6 atoms; at least one of which is aromatic in which one or more carbon atoms in one or more of these rings can be replaced by oxygen, nitrogen or sulfur atoms where the nitrogen and sulfur heteroatoms may optionally be oxidized and the nitrogen heteroatoms may optionally be quaternized. Such rings may be fused to an aryl, cycloalkyl, heteroaryl or heterocyclyl ring. Non-limiting examples of such heteroaryl, include: pyrrolyl, furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, imidazo[2,1-b][1,3]thiazolyl, thieno[3,2-b]furanyl, thieno[3,2-b]thiophenyl, thieno[2,3-d][1,3]thiazolyl, thieno[2,3-d]imidazolyl, tetrazolo[1,5-a]pyridinyl, indolyl, indolizinyl, isoindolyl, benzofuranyl, isobenzofuranyl, benzothiophenyl, isobenzothiophenyl, indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, thienopyridinyl, purinyl, imidazo[1,2-a]pyridinyl, 6-oxo-pyridazin-1 (6H)-yl, 2-oxopyridin-1 (2H)-yl, 6-oxo-pyrudazin-1(6H)-yl, 2-oxopyridin-1(2H)-yl, 1,3-benzodioxolyl, quinolinyl, isoquinolinyl, cinnolinyl, quinazolinyl, quinoxalinyl. The heteroaryl group can be substituted by one or more substituents chosen independently of one another, among a hydroxyl group; a linear, cyclic or branched alkyl group comprising 1, 2, 3, 4, 5 or 6 carbon atoms, in particular methyl, ethyl, propyl, butyl; an alkoxy group; a halogen atom, in particular bromine, chlorine and iodine; a nitro group; a cyano group; an azido group; an aldehyde group; a boronato group; a phenyl; $CF_3$; methylenedioxy; ethylenedioxy; $SO_2NRR'$, NRR', COOR wherein R and R' are each independently selected from the group consisting of H, alkyl, cycloalkyl, alkenyl, cycloalkenyl, alkynyl, cycloalkynyl and aryl.

"heterocyclyl" refers to non-aromatic, fully saturated or partially unsaturated cyclic groups (for example, 3 to 7 member monocyclic, 7 to 11 member bicyclic, or containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The rings of multi-ring heterocycles may be fused, bridged and/or joined through one or more spiro atoms. Non limiting exemplary heterocyclic groups include aziridinyl, oxiranyl, thiiranyl, piperidinyl, azetidinyl, 2-imidazolinyl, pyrazolidinyl imidazolidinyl, isoxazolinyl, oxazolidinyl, isoxazolidinyl, thiazolidinyl, isothiazolidinyl, piperidinyl, succinimidyl, 3H-indolyl, indolinyl, isoindolinyl, 2H-pyrrolyl, 1-pyrrolinyl, 2-pyrrolinyl, 3-pyrrolinyl, pyrrolidinyl, 4H-quinolizinyl, 2-oxopiperazinyl, piperazinyl, homopiperazinyl, 2-pyrazolinyl, 3-pyrazolinyl, tetrahydro-2H-pyranyl, 2H-pyranyl, 4H-pyranyl, 3,4-dihydro-2H-pyranyl, oxetanyl, thietanyl, 3-dioxolanyl, 1,4-dioxanyl, 2,5-dioximidazolidinyl, 2-oxopiperidinyl, 2-oxopyrrolodinyl, indolinyl, tetrahydropyranyl, tetrahydrofuranyl, tetrahydrothiophenyl, tetrahydroquinolinyl, tetrahydroisoquinolin-1-yl, tetrahydroisoquinolin-2-yl, tetrahydroisoquinolin-3-yl, tetrahydroisoquinolin-4-yl, thiomorpholin-4-yl, thiomorpholin-4-ylsulfoxide, thiomorpholin-4-ylsulfone, 1,3-dioxolanyl, 1,4-oxathianyl, 1,4-dithianyl, 1,3,5-trioxanyl, 1H-pyrrolizinyl, tetrahydro-1,1-dioxothiophenyl, N-formylpiperazinyl, and morpholin-4-yl.

"heteropeptide" refers to a peptide comprising at least one amino acid and at least one building block which is not an amino acid. The term "amino acid" includes both L- and D-isomers of the naturally occurring amino acids and non-naturally-occurring amino acids. Examples of naturally-occurring amino acids are glycine, alanine, valine, leucine, isoleucine, serine, threonine. Other amino acids include for example norleucine, norvaline, biphenyl alanine or substituted phenyl alanine. Non limited exemplary non-amino acid part of the heteropeptide include beta-glutamic acid, beat-alanine, amino benzoic acid, succinic acid, oxalic acid or ethylenediamine.

"linker" refers to a single covalent bond or a moiety comprising series of stable covalent bonds, the moiety often incorporating 1-40 plural valent atoms selected from the group consisting of C, N, O, S and P, that covalently attach a reactive function or bioactive group to the aryl or heteroaryl group of the ionic liquid supported organotin reagent (I) or of compounds (II) or (III) of the invention. The number of plural valent atoms in a linker may be, for example, 0, 1, 2, 3, 4, 5, 6, 7, 8, 9, 10, 20, 25, 30 or a larger number up to 40 or more. A linker may be linear or non-linear; some linkers have pendant side chains or pendant functional groups (or both). Examples of such pendant moieties are hydrophilicity modifiers, for example solubilising groups like, e.g. sulfo (—SO₃H or —SO₃⁻). In one embodiment, the "linker" is composed of any combination of single, double, triple or aromatic carbon-carbon bonds, carbon-nitrogen bonds, nitrogen-nitrogen bonds, carbon-oxygen bonds and carbon-sulfur bonds. Linkers may by way of example consist of a combination of moieties selected from alkyl, —C(O)NH—, —C(O)O—, —NH—, —S—, —O—, —C(O)—, —S(O)n- where n is 0, 1 or 2; —O—; 5- or 6-membered monocyclic rings and optional pendant functional groups, for example sulfo, hydroxy and carboxy.

In the case wherein the linker is bonded to a reactive group, the reactive group may be reacted with a substance reactive therewith, whereby the linker becomes bonded to a bioactive group. In this case, the linker typically contains a residue of the reactive group (such as for example the carbonyl group of an ester or a triazolo group resulting from a click reaction between an azide and an alkyne). By "triazolo group" it is referred to the following moiety:

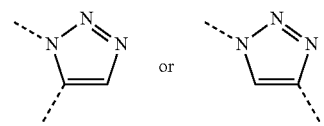

Other examples of residues of coupling residues resulting from coupling between reactive functions are the following:

| reactive function A | reactive function B | coupling residue | examples of coupling residue |
|---|---|---|---|
| carboxylic acid | amine, hydroxyl, sulfhydryl, hydrazine | amide, ester, thioester, hydrazide: | 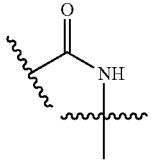 |
| activated ester | amine, hydroxyl, sulfhydryl, hydrazine | amide, ester, thioester, hydrazide | 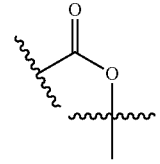 |
| aldehyde | amine, alkoxyamine, hydrazine, hydrazide | amine, oxime, hydrazone | 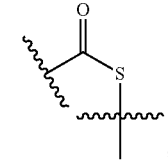 |

-continued
| reactive function A | reactive function B | coupling residue | examples of coupling residue |
|---|---|---|---|
| | | | 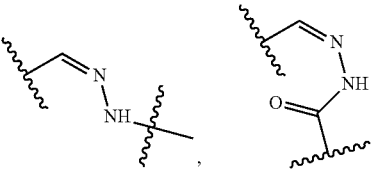 [SMILES: */C=N\N* ; */C=N\NC(*)=O] |
| ketone | amine, alkoxyamine, hydrazide, hydrazine | amine, oxime, hydrazone | 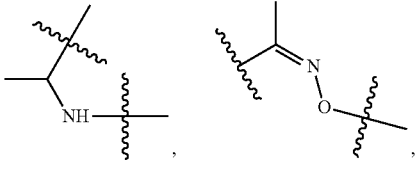 |
| thioester | azide | amide (through traceless Staudinger ligation) | 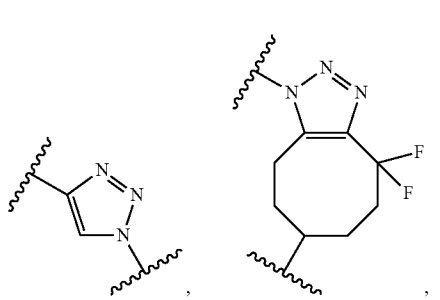 [SMILES: *c1cn(*)nn1 ; *C1CCc2c(nnn2*)C(F)(F)CC1 ; "," ; ","] |
| alkyne | azide, thiol | triazolyl thioether, | 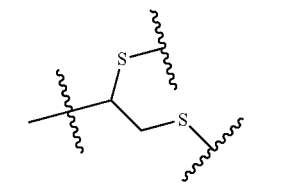 [SMILES: *SCC(*)S*] |
| alkene | thiol | thioether | |

-continued

| reactive function A | reactive function B | coupling residue | examples of coupling residue |
|---|---|---|---|
| azide | alkyne, phosphine, thioester | triazole, amide (through traceless Staudinger ligation) | 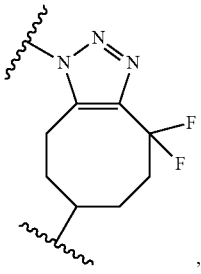, 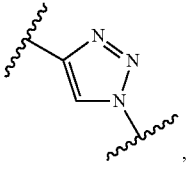, 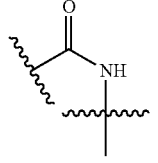 [SMILES: *NC(*)=O] |
| maleimide | sulfhydryl, diene | thioether, cyclic alkene | 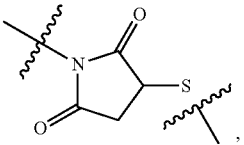, 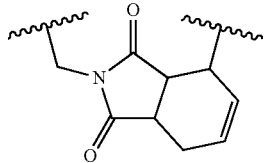 |
| diene | maleimide | cyclic alkene | 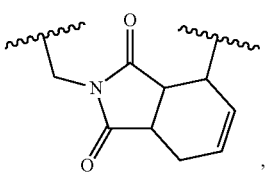, 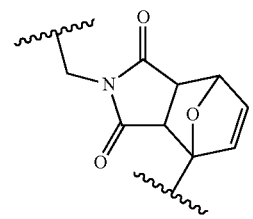 |
| hydroxyl | carboxylic acid, activated ester, tosylate ester | ester, ether | |
| thiol | alkene, alkyne, maleimide, carboxylic acid, activated ester, tosylate ester, vinyl sulfone | thioether, thioester | 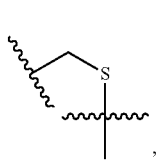, 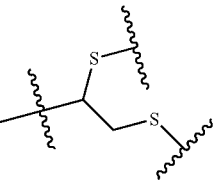, 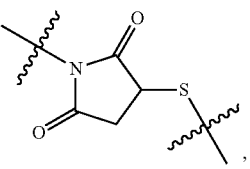, 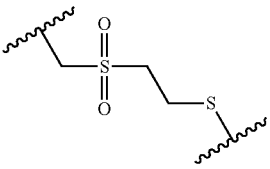, 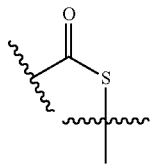 [SMILES: *SC(*)=O] |

-continued

| reactive function A | reactive function B | coupling residue | examples of coupling residue |
|---|---|---|---|
| amine | aldehyde, cetone, hydroxyl (oxydation), tosylate ester, carboxylic acid, activated ester, isothiocyanate, isocyanate, alkylphosphate, ester carbonate | amine, amide, phosphoramidate, thiourea, urea, carbamate | 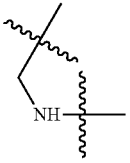, 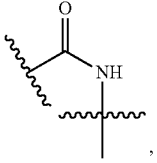, 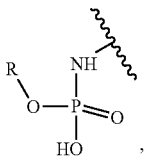, 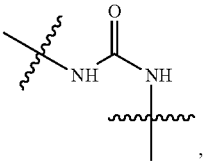, 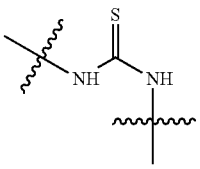, 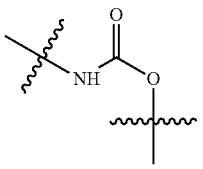 |
| phosphine | azide | amide | 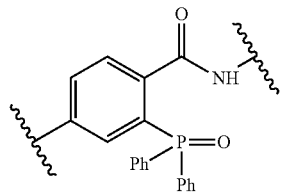 [SMILES: *NC(=O)c1ccc(*)cc1P(=O)(c1ccccc1)c1ccccc1] |
| isothiocyanate | amine | thiourea | 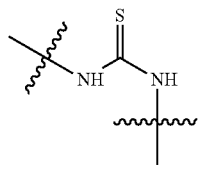 |
| isocyanate | amine | urea | 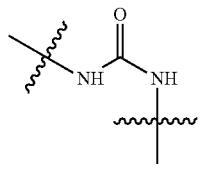 [SMILES: *NC(=O)N*] |
| alkoxyamine | aldehyde, ketone | oxime | 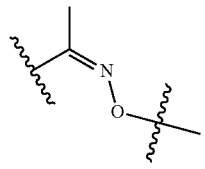 [SMILES: *O/N=C(\*)C] |
| hydrazide | aldehyde, ketone, | hydrazone | 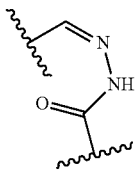 [SMILES: */C=N\NC(*)=O] |

| reactive function A | reactive function B | coupling residue | examples of coupling residue |
|---|---|---|---|
| hydrazine | aldehyde, ketone, carboxylic acid, ctivated ester | hydrazone, hydrazide | 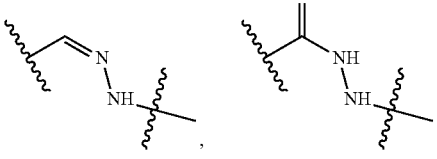 |
| phenol | carboxylic acid, aniline, PTAD derivatives | ester, substituted phenol, azo compounds | 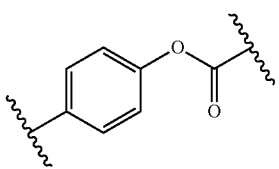 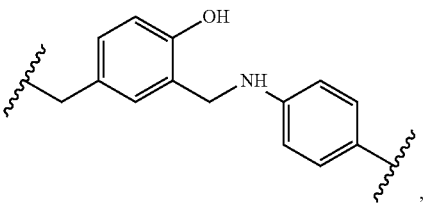 [SMILES: *Cc1ccc(O)c(CNc2ccc(*)cc2)c1] 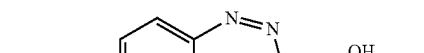 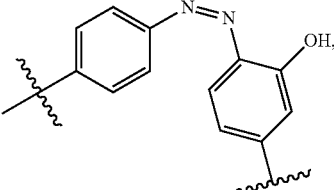 |
| 2-aminophenol | aniline | | 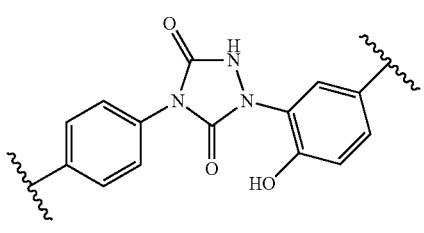 [SMILES: *c1ccc(-n2c(=O)[nH]n(-c3cc(*)ccc3O)c2=O)cc1] 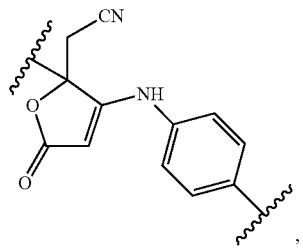 [SMILES: *c1ccc(NC2=CC(=O)OC2(*)CC#N)cc1] |

| reactive function A | reactive function B | coupling residue | examples of coupling residue |
|---|---|---|---|
| aniline | carboxylic acid, 2-aminophenol, phenol | anilide, substituted phenol, azo compounds, | 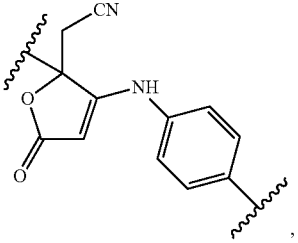 [SMILES: *c1ccc(NC2=CC(=O)OC2(*)CC#N)cc1] 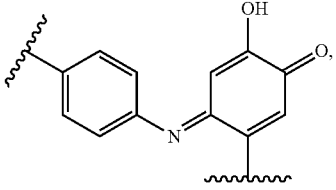 [SMILES: *C1=CC(=O)C(O)=C/C1=N\c1ccc(*)cc1] 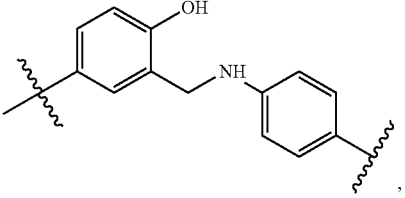 [SMILES: *c1ccc(NCc2cc(*)ccc2O)cc1] 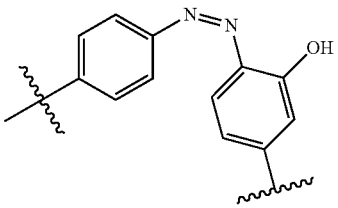 [SMILES: *c1ccc(/N=N\c2ccc(*)cc2O)cc1] |
| tosylate ester | amine, hydroxyle, sulfhydryle, | alkylated amine, thioether, ether | |
| vinyl sulfone | sulfhydryle | | 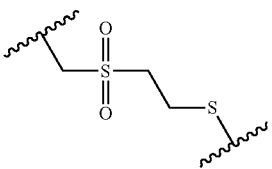 [SMILES: *CS(=O)(=O)CCS*] |
| carbonate ester | amine | carbamate | 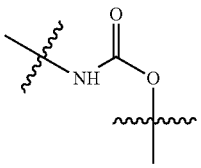 |
| PTAD derivatives | phenol | | 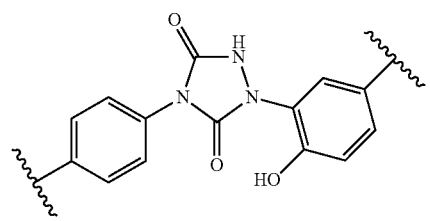 [SMILES: *c1ccc(-n2c(=O)[nH]n(-c3cc(*)ccc3O)c2=O)cc1] |

| reactive function A | reactive function B | coupling residue | examples of coupling residue |
|---|---|---|---|
| alkyl phosphate | amine | phosphoramidate | 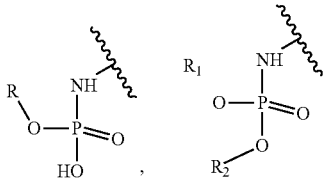 |

"neurotransmitter" refers to endogenous chemicals that transmit signals across a synapse from one neuron (brain cell) to another 'target' neuron. Examples of neurotransmitters are: amino acids such as for example glutamate, aspartate, D-serine, γ-aminobutyric acid (GABA) or glycine; monoamines such as for example dopamine (DA), norepinephrine (noradrenaline; NE, NA), epinephrine (adrenaline), histamine or serotonin (SER, 5-HT); trace amines such as for example phenethylamine, N-methylphenethylamine, tyramine, 3-iodothyronamine, octopamine or tryptamine; peptides such as for example somatostatin, substance P, cocaine and amphetamine regulated transcript or opioid peptides; gasotransmitters such as for example nitric oxide (NO), carbon monoxide (CO) or hydrogen sulfide (H2S); acetylcholine (ACh), adenosine, anandamide.

"Sympatomimetic drug" refers to compounds which mimic the effects of neurotransmitter substances of the sympathetic nervous system such as catecholamines, epinephrine (adrenaline), norepinephrine (noradrenaline), dopamine, etc. Examples of sympathomimetic drugs can be direct-acting drugs, such as α-adrenergic agonists, β-adrenergic agonists (such as for example salbutamol, phenylephrine, isoproterenol, dobutamine), and dopaminergic agonists (such as for example fenoldopam); or indirect-acting drugs, such as MAOIs, COMT inhibitors, release stimulants, and reuptake inhibitors that increase the levels of endogenous catecholamines, norepinephrine and dopamine transporter blockade (such as for example bamphetamines, including MDMA; ephedrine; cocaine).

"PEG chain" or "polyethylene glycol chain" refers to an oligomer or polymer of ethylene oxide, with a molecular mass below 20,000 g/mol.

"protected phosphine" refers to a phosphine group —PR$^1$R$^2$R$^3$, wherein R$^1$, R$^2$ and R$^3$ are selected from H, alkyl, cycloalkyl, heterocyclyl, aryl, heteroaryl, alkenyl, cycloalkenyl, alkynyl, cycloalkynyl or even a phosphorus atom (diphosphine) in which the lone pair (valence electron pair) of the phosphorus atom is in a dative bond, disabling the nucleophilicity of the phosphorus atom, and therefore its reactivity towards electrophilic functional group; the dative bond being cleavable in specific conditions. Examples of protected phosphines are phosphine-boranes.

"protected thiol" refers to a thiol group —SH in which the hydrogen is substituted by a protecting group selected for its ability to be cleavable in specific conditions (acidic conditions for example), disabling the nucleophilicity of the sulfur atom, and therefore its reactivity towards electrophilic functional groups or the formation of disulfide bond. Examples of protected thiols are thioacetate or disulfide such as for example 2-pyridyldithio group.

"reactive function" refers to a group capable of reacting with another chemical group to form a covalent bond, i.e. is covalently reactive under suitable reaction conditions, and generally represents a point of attachment for another substance. The reactive group is a moiety on the compounds of the present invention that is capable of chemically reacting with a functional group on a different compound to form a covalent linkage. Reactive groups generally include nucleophiles, electrophiles and photoactivable groups. In a preferred embodiment, "reactive function" refers to any chemical group which is reactive towards the chemical functions of a vector (i.e. bioactive group) and thus allows the formation of a stable chemical bond between the vector and the radiolabelled precursor. The formation of the stable bond between the vector and the reactive function of the radiolabelled precursor can occur in one step or in a multi-step synthesis. According to a first embodiment, the reactive group may be under deprotected form, and may thus directly be used to react with the reactive group of the vector. According to a second embodiment, the reactive group may be under protected form and should thus be deprotected before being reacted with the reactive group of the vector. According to one embodiment, "reactive function" may refer, but is not limited to protected or unprotected reactive functions selected from carboxylic acid, nitriles, esters (e.g but not limited to ethyl and methyl esters), activated ester (e.g. but not limited to, succinimidyl, sulfosuccinimidyl, tetrafluorophenyl, pentafluorophenyl, nitrophenyl esters), aldehyde, acetal, ketone, ketal, alkyne, azide, alkene, diene, maleimide, protected maleimide, alcohol (i.e. hydroxyl), ether, phenol, 2-aminophenol, thiol, thioester, thioether, thiosulfonate, primary amine, secondary amine, tertiary amine, alkoxyamine, aniline, amide, phosphine, alkyl phosphate, isocyanates, isothiocyanates, hydrazide, hydrazine, tosylate ester, vinyl sulfone, carbamate, carbonate ester, 4-phenyl-1,2,4-triazole-3,5-dione (PTAD), sulphide, azidoalkyl and azidoaryl.

Illustrative examples of such reactive functions are the following:

| Type of reactive function | examples of reactive function | |
|---|---|---|
| | unprotected form | protected form |
| carboxylic acid | —COOH | —CN, —C(O)O—CH₃, —C(O)O—(CH₂)ₙ—CH₃ wherein n represents an integer ranging from 0 to 10 |
| activated ester | NHS ester, pentafluorophenyl ester, tetrafluorophenyl ester, 4-nitrophenyl ester, 2-(ethyldisulfanyl)phenyl ester (see also the definition of activated esters above) | |
| aldehyde | —CHO | dimethyl acetal, cyclic/alkyl acetal |

-continued
| Type of reactive function | examples of reactive function | |
|---|---|---|
| | unprotected form | protected form |
| | | <br>wherein n represents an integer ranging from 0 to 10 |
| ketone | 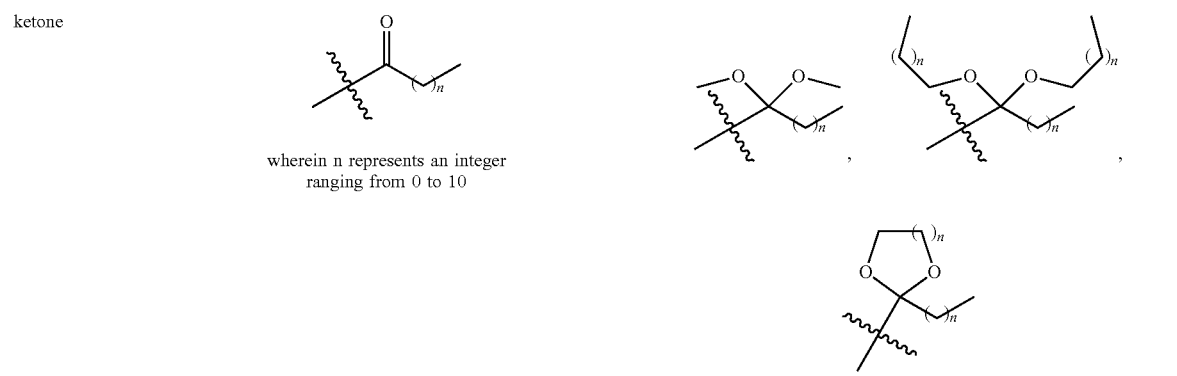<br>wherein n represents an integer ranging from 0 to 10 | |
| | | wherein n represents an integer ranging from 0 to 10 |
| thioester | 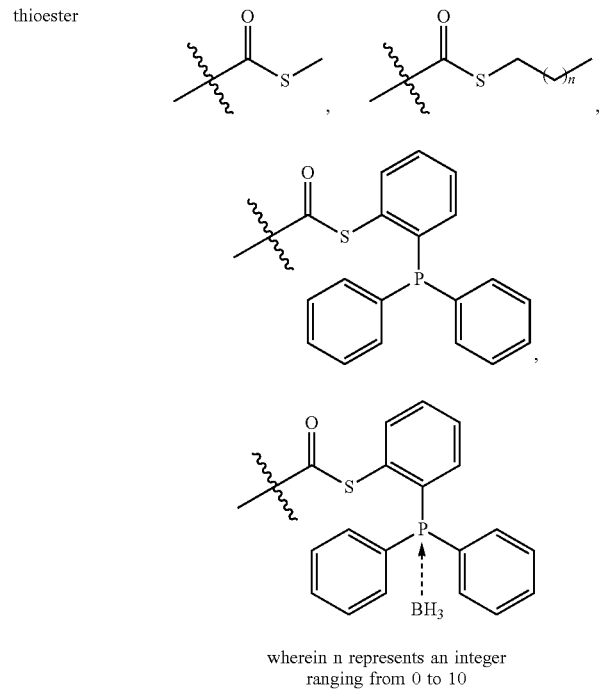<br>wherein n represents an integer ranging from 0 to 10 | |
| alkyne | | |

-continued
| Type of reactive function | examples of reactive function | |
|---|---|---|
| | unprotected form | protected form |
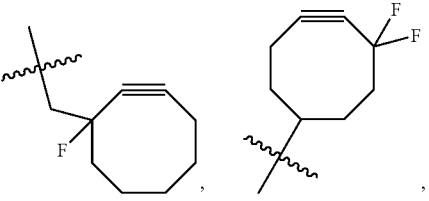 [SMILES: *CC1(F)C#CCCCCC1 ; *C1CCC#CC(F)(F)CC1]
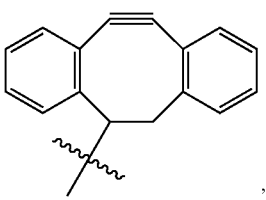 [SMILES: *C1Cc2ccccc2C#Cc2ccccc21]
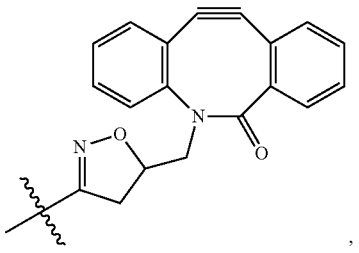 [SMILES: *C1=NOC(CN2C(=O)c3ccccc3C#Cc3ccccc32)C1]
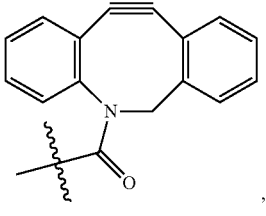 [SMILES: *C(=O)N1Cc2ccccc2C#Cc2ccccc21]
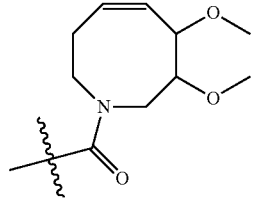
alkene
azide
—N₃

-continued

| Type of reactive function | examples of reactive function | |
|---|---|---|
| | unprotected form | protected form |
| maleimide | | |
| diene | | |
| hydroxyl | —OH | wherein n represents an integer ranging from 0 to 10 |
| thiol | —SH | thiosulfonates |
| amine | —NH₂, —NH, —NH  wherein n represents an integer ranging from 0 to 10 | —NHBoc, |

-continued

| Type of reactive function | examples of reactive function | |
|---|---|---|
| | unprotected form | protected form |
| phosphine | *structure with PPh₂ and methyl benzoate* | *structure with PPh₂→BH₃ and methyl benzoate* |
| isothiocyanate | –NCS, *phenyl-NCS* | |
| isocyanate | –NCO | *acyl azide (C(O)N₃)* |
| alkoxyamine | *–O–NH₂* | *–O–NHBoc* |
| hydrazide | *–C(O)–NH–NH₂* | *–C(O)–NH–NHBoc* |
| hydrazine | *–NH–NH₂* | *–NH–NHBoc* |
| phenol | *4-hydroxyphenyl* | |
| 2-aminophenol | *2-amino-4-substituted phenol* | |
| aniline | *4-aminophenyl* | |
| tosylate ester | *–CH₂–O–S(O)₂–C₆H₄–CH₃* | |

| Type of reactive function | examples of reactive function | |
|---|---|---|
| | unprotected form | protected form |
| vinyl sulfone | ![vinyl sulfone structure] | |
| carbonate ester | | ![carbonate ester structure] |
| PTAD derivatives | | ![PTAD derivative structure] |
| alkyl phosphate | ![alkyl phosphate structures] | ![protected alkyl phosphate structure] |

"radiohalogen" refers to a radioactive isotope of a halogen atom, preferably $^{123}$I, $^{125}$I, $^{131}$I, $^{124}$I, $^{211}$At, $^{76}$Br, $^{18}$F, more preferably $^{125}$I, $^{211}$At or $^{18}$F, more preferably $^{211}$At or $^{18}$F.

Y* represents a halogen atom, preferably a radiohalogen atom. According to a specific embodiment, Y* represents $^{125}$I. According to another specific embodiment, Y* represents $^{211}$At. According to another specific embodiment, Y* represents $^{18}$F.

Unless indicated otherwise, the nomenclature of substituents that are not explicitly defined herein are arrived at by naming the terminal portion of the functionality followed by the adjacent functionality toward the point of attachment. For example, the substituent "arylalkyl" refers to the group (aryl)-(alkyl)-.

DETAILED DESCRIPTION

Ionic Liquid Supported Organotin Reagent (I)

The present invention relates to an ionic liquid supported organotin reagent of formula (I)

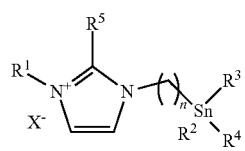

(I)

wherein:

X⁻ represents an anion, preferably X⁻ represents an anion selected from the group comprising halide, acetate, trifluoroacetate, triflate (Tf), NTf$_2$⁻, alkylsulfate, sulfonate, tetrafluoroborate (BF$_4$⁻), tetraarylborate, hexafluorophosphate (PF$_6$⁻), NO$_3$⁻, SbF$_6$⁻, prolinate, hydroxide, hydrogen sulfate, tetrachloroferrate, aluminum tetrachloride, perfluorobutylsulfonate, p-toluenesulfonate, formiate and dihydrogen phosphate; more preferably X⁻ represents BF$_4$⁻, PF$_6$⁻, Cl⁻, Br⁻, I⁻, NTf$_2$⁻, even more preferably X⁻ represents BF$_4$⁻, PF$_6$⁻ or Br⁻;

n represents an integer ranging from 3 to 10, preferably n represents 4, 5, 6, 7 or 8, more preferably n represents 6;

$R^1$ represents an alkyl group, a PEG chain, preferably $R^1$ represents methyl, ethyl, n-butyl;

$R^2$ and $R^3$ each independently represent an alkyl group, preferably $R^2$ and $R^3$ are both n-butyl;

$R^5$ represents H, alkyl or aryl, preferably H, methyl or phenyl;

$R^4$ represents:
  an aryl vector; or
  a group selected from aryl and heteroaryl substituted by one or more substituents -L-M wherein:
  L represents a single bound or a linker selected from aryl, heteroaryl, alkyl, cycloalkyl, alkenyl, cycloalkenyl, alkynyl, cycloalkynyl or a combination thereof;
    said groups being optionally substituted by at least one group selected from oxo, thioxo, hydroxyl, ether, carboxylic acid, ester, alkyl, cycloalkyl, alkenyl, cycloalkenyl, heterocyclyl, alkynyl, cycloalkynyl, amine, amide, guanidine, imino, nitro, nitrile, azide, sulfhydryl, sulfide, thioester, thioether, sulfite, sulfate, phosphine, phosphite, phosphate, halogen;
    said groups being optionally interrupted or terminated by —O—, —S—, —NR$^6$— wherein R$^6$ is H or alkyl, or a combination thereof; and
    optionally L additionally comprises a residue of a reactive group through which L is bounded to M;
  M represents:
    a reactive function selected from carboxylic acid, nitrile, ester, activated ester, aldehyde, acetal, ketone, ketal, alkyne, azide, alkene, diene, maleimide, protected maleimide, hydroxyl, ether, phenol, 2-aminophenol, thiol, thioester, thioether, thiosulfonate, primary amine, secondary amine, tertiary amine, alkoxyamine, aniline, amide, phosphine, alkyl phosphate, isocyanates, isothiocyanates, hydrazide, hydrazine, tosylate ester, vinyl sulfone, carbamate, carbonate ester, 4-phenyl-1,2,4-triazole-3,5-dione, sulphide, azidoalkyl and azidoaryl; or
    a bioactive group selected from amino acid, biogenic amine, peptide, heteropeptide, protein, antibody or fragment thereof, monobody, affibody, antibody construct such as a for example minibody or diabody, saccharide, polysaccharide, benzylguanine, biotin, avidin, nucleotide, oligonucleotide, microRNA, hapten, aptamer, ligand, enzyme, enzyme substrate, steroid, hormone, porphyrin, neurotransmitters, sympatomimetic drug, vitamin, phosphonate, nanocarrier such as for example nanocapsule, liposome, dendrimer, carbon nanotube and combinations thereof;
  said aryl or heteroaryl being optionally further substituted by one or more substituents selected from hydroxyl; linear, cyclic or branched alkyl comprising 1, 2, 3, 4, 5 or 6 carbon atoms; aryl; heteroaryl; heterocyclyl; arylheterocyclyl; alkoxy; halogen; nitro; cyano; azido; aldehyde; boronato; phenyl; $CF_3$; —$CH(OH)(CF_3)$; —$CH(OCH_2OCH_3)(CF_3)$; methylenedioxy; ethylenedioxy; $SO_2NRR'$, NRR', COOR, CONRR', NRCOR' wherein R and R' are each independently selected from the group consisting of H, alkyl, cycloalkyl, alkenyl, cycloalkenyl, alkynyl, cycloalkynyl and aryl.

According to one embodiment, compound (I) is such that:
  when n is equal to 6, $X^-$ is $I^-$, $R^1$ is methyl, $R^2$ and $R^3$ are both n-butyl and $R^5$ is H, then $R^4$ is not phenyl;
  when n is equal to 6, $X^-$ is $Br^-$, $R^1$ is ethyl, $R^2$ and $R^3$ are both n-butyl and $R^5$ is H, then $R^4$ is not phenyl, 4-methoxyphenyl, 4-fluorophenyl or thiophen-2-yl;
  when n is equal to 3, $X^-$ is $BF_4^-$, $R^1$ is methyl, $R^2$ and $R^3$ are both n-butyl and $R^5$ is H or methyl, then $R^4$ is not phenyl;
  when n is equal to 3, $X^-$ is $I^-$, $R^1$ is methyl, $R^2$ and $R^3$ are both n-butyl and $R^5$ is H or methyl or phenyl, then $R^4$ is not phenyl;
  when n is equal to 6, $X^-$ is $I^-$, $R^1$ is methyl, $R^2$ and $R^3$ are both n-butyl and $R^5$ is H, then $R^4$ is not phenyl.

According to one embodiment, when $R^4$ is an aryl vector, $R^4$ is:

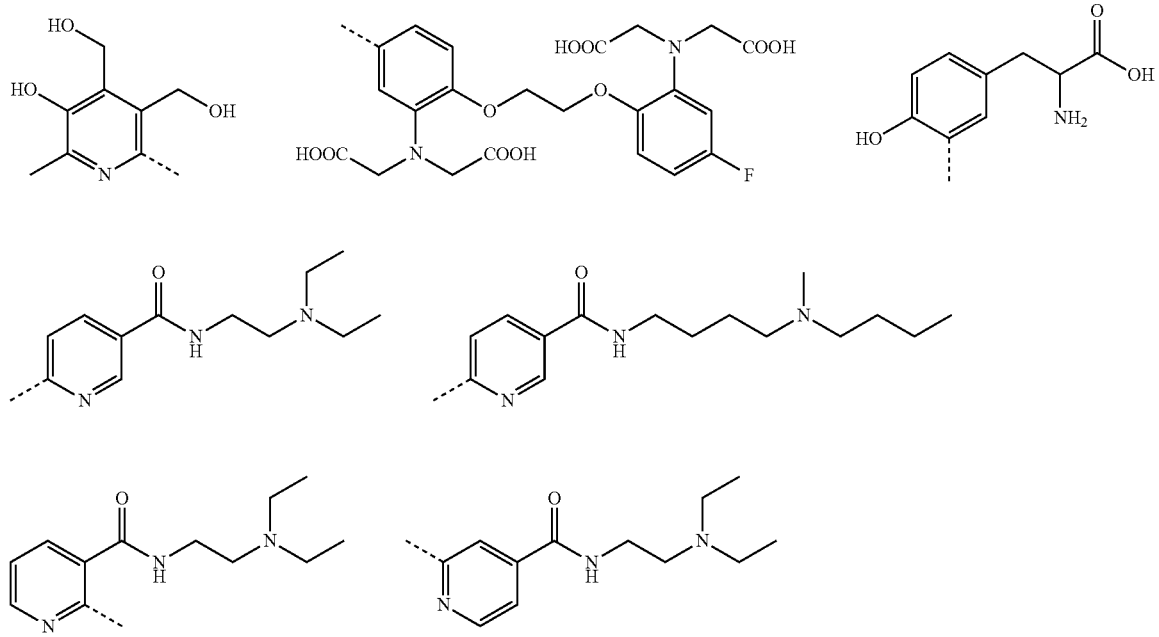

-continued
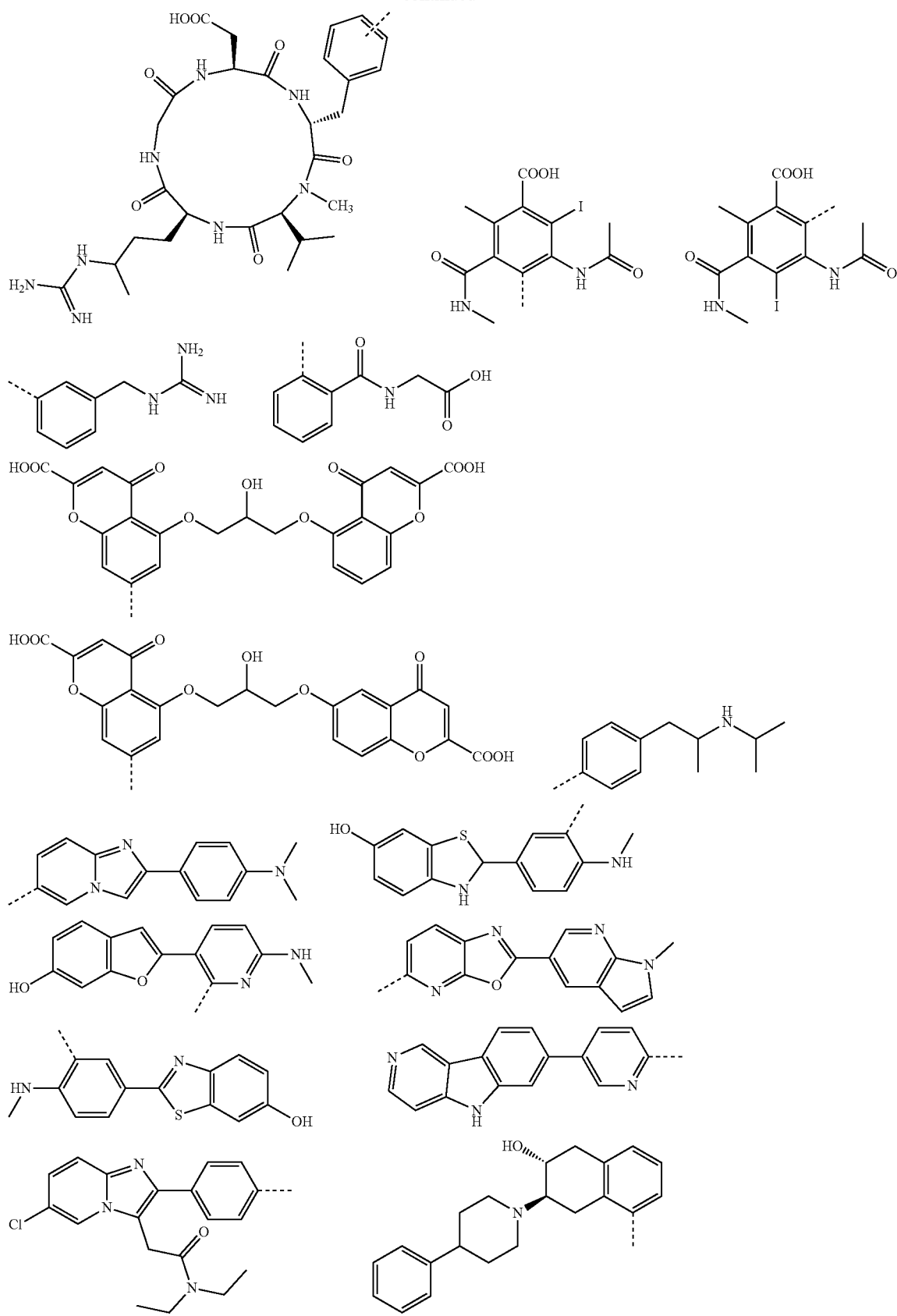

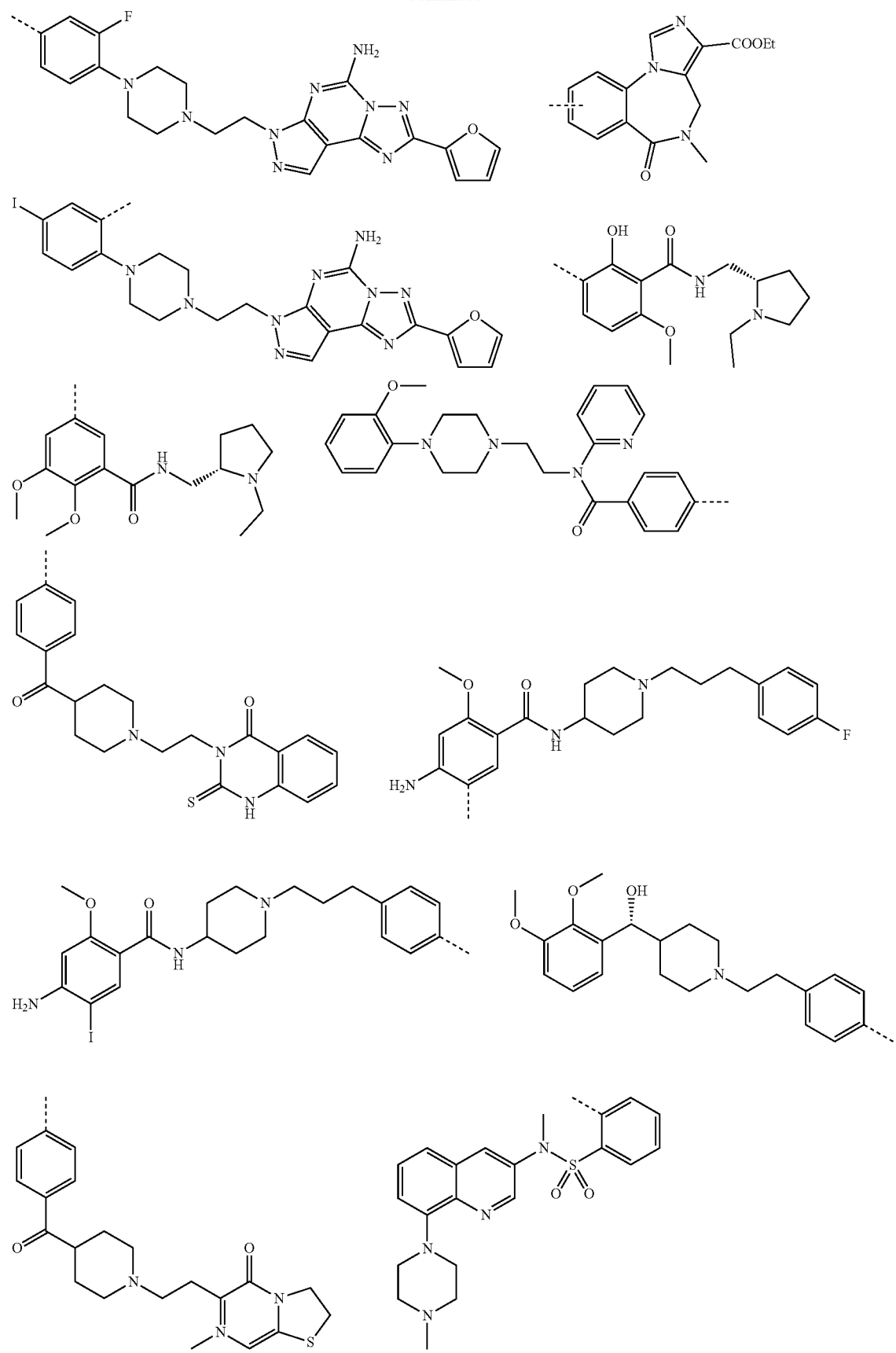

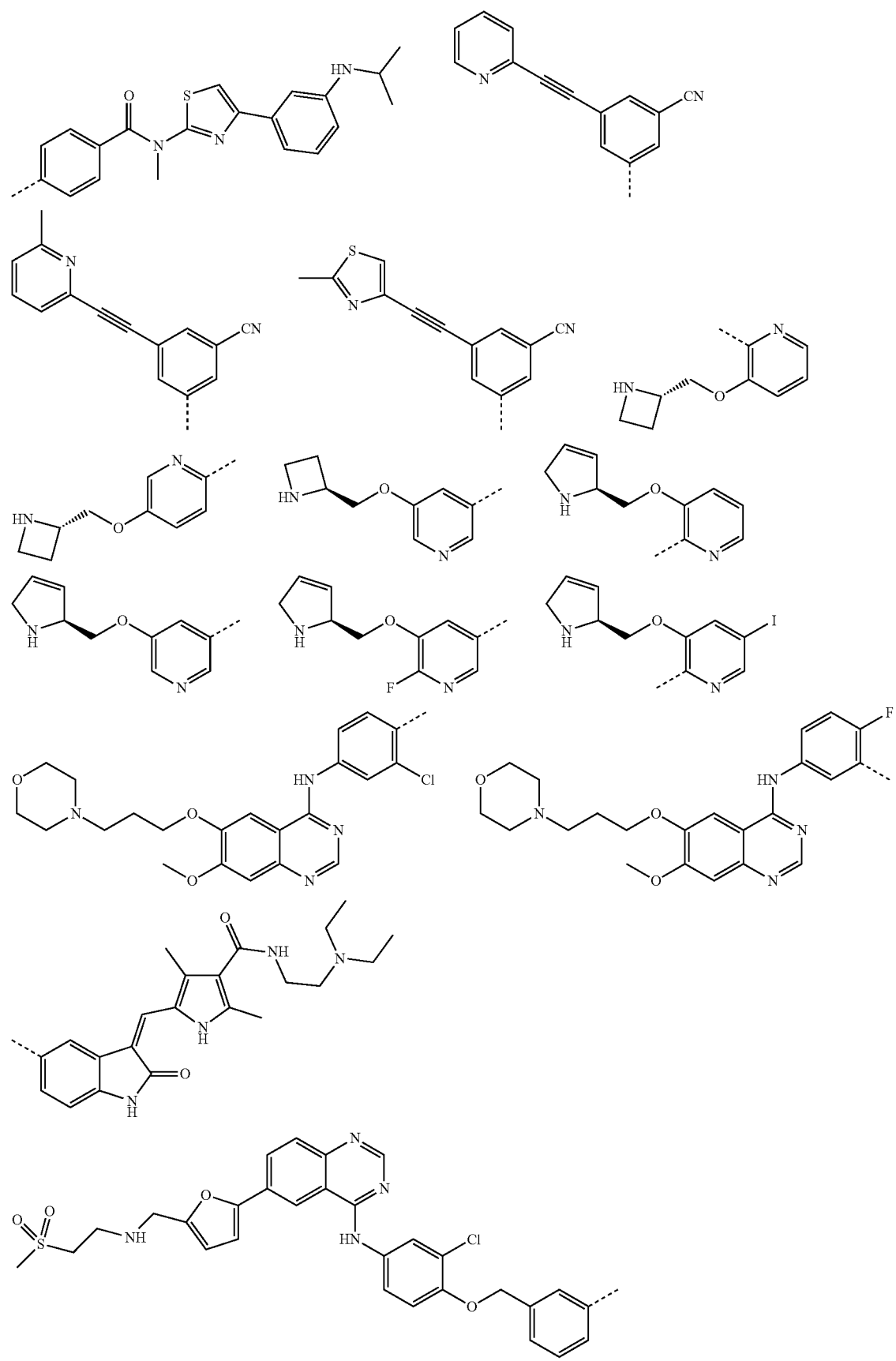

-continued
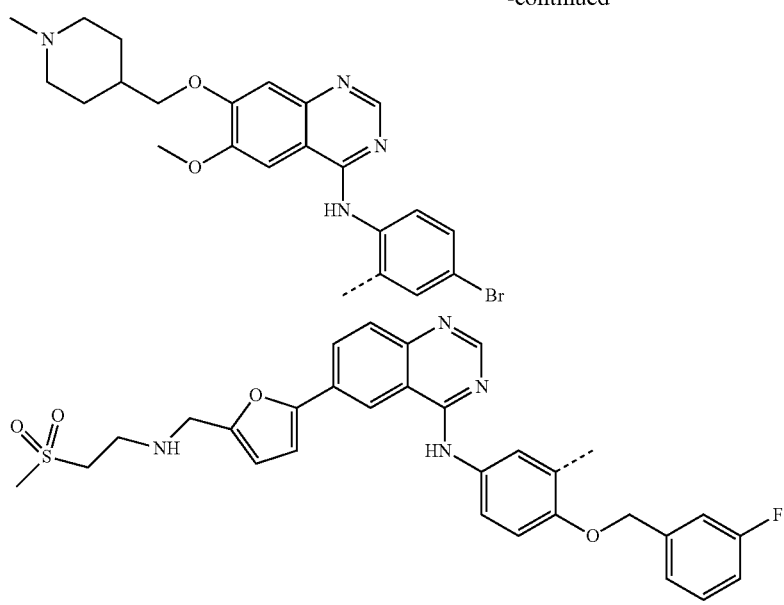
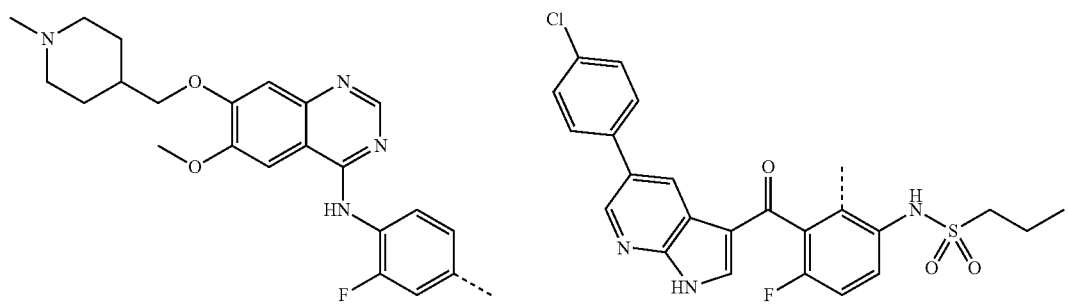
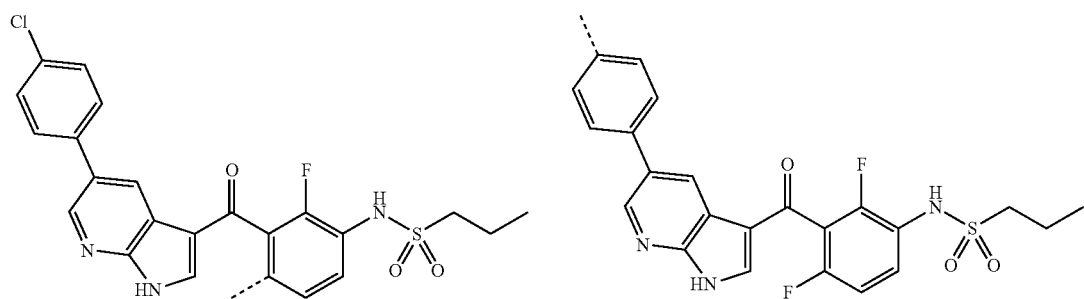
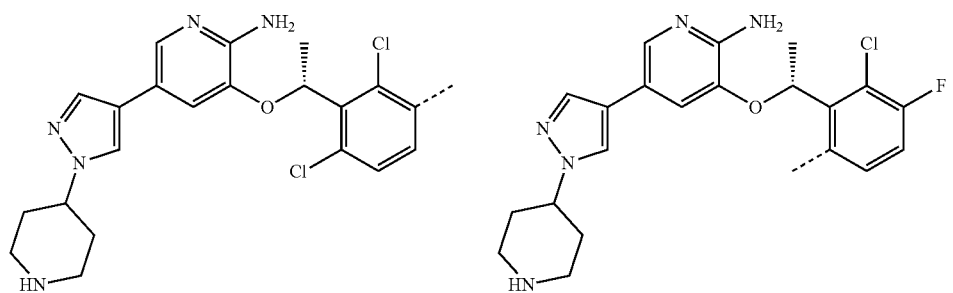

-continued

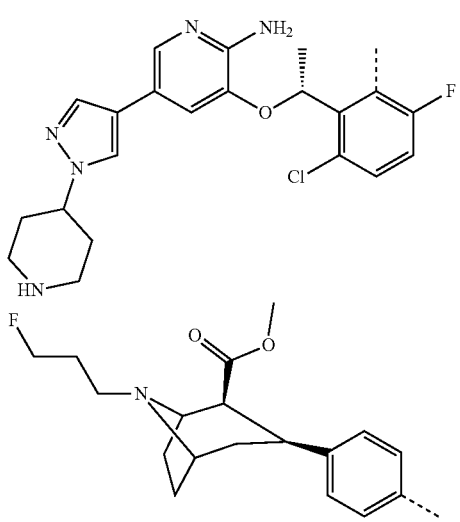
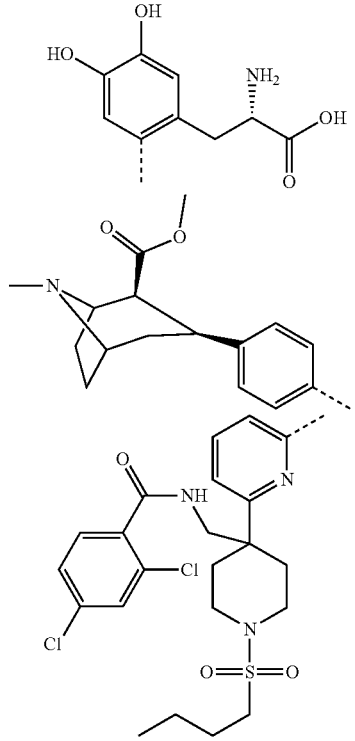
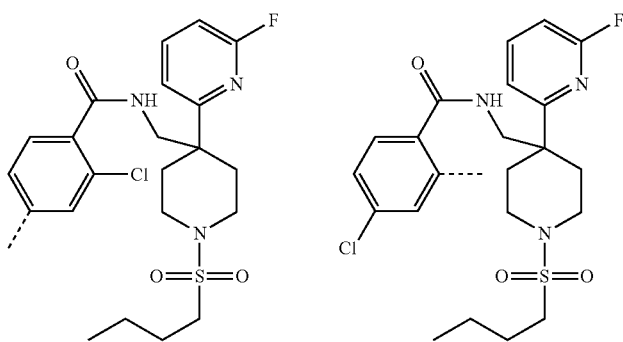

Above aryl vectors correspond to compounds which upon labeling by a radiohalogen atom lead to radiopharmaceuticals enabling nuclear imaging and/or therapy.

According to one embodiment, the ionic liquid supported organotin reagent of formula (I) is such that X⁻ represents an anion, preferably an anion selected from the group comprising halide, acetate, trifluoroacetate, triflate (Tf), alkylsulfate, sulfonate, tetrafluoroborate (BF₄⁻), tetraarylborate, hexafluorophosphate (PF₆⁻), NO₃⁻, SbF₆⁻ and derivatives thereof, more preferably BF₄⁻, PF₆⁻, Cl⁻, Br⁻, I⁻, NTf₂⁻, more preferably BF₄⁻, PF₆⁻ or Br⁻;

n represents an integer ranging from 3 to 10, preferably n is 4, 5, 6, 7 or 8, more preferably n is 6;

R¹ represents an alkyl group, a PEG chain, preferably methyl, ethyl, n-butyl;

R² and R³ each independently represent an alkyl group, preferably R² and R³ are both n-butyl;

R⁴ represents a group selected from aryl and heteroaryl, substituted by one or more substituents -L-M wherein:

L represents a linker selected from single bound or a group selected from aryl, alkyl, cycloalkyl, alkenyl, cycloalkenyl, alkynyl, cycloalkynyl;

said groups being optionally substituted by at least one group selected from oxo, thioxo, hydroxyl, ether, carboxylic acid, ester, alkyl, cycloalkyl, alkenyl, cycloalkenyl, heterocyclyl, alkynyl, cycloalkynyl, amine, amide, guanidine, nitro, nitrile, azide, sulfhydryl, sulfide, thioester, thioether, sulfite, sulfate, phosphine, phosphite, phosphate;

said groups being optionally interrupted or terminated by —O—, —S—, —NR⁶— wherein R⁶ is H or alkyl, or a combination thereof; and optionally additionally comprising a residue of a reactive group through which L is bounded to M;

M represents:
  a hydrogen atom;
  a reactive function selected from carboxylic acid, primary amine, secondary amine, tertiary amine, carbamate, amide, maleimide, ester alcohol, aldehyde, nitrile, isocyanate, isothiocyanate, phosphine, protected phosphine, thiol, protected thiol, azide, sulphide, azidoalkyl and azidoaryl;
  a bioactive group selected from amino acid, biogenic amine, peptide, affibody, protein, antibody or fragment thereof, antibody construct such as a for example minibody or, diabody, saccharide, polysaccharide, benzylguanine, biotine, dihydroxyphenylalanine, nucleotide, oligonucleotide, hapten, ligand, enzyme substrate, nanocarrier such as for example nanocapsule, liposome, dendrimer or carbon nanotube and derivatives and combinations thereof;
$R^5$ represents H, alkyl or aryl, preferably H, methyl or phenyl.

In one embodiment, the ionic liquid supported organotin reagent of the invention is of formula (Ia)

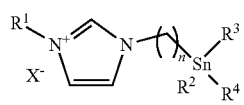

(Ia)

wherein $X^-$, n, $R^1$, $R^2$, $R^3$, $R^4$ are as defined above.

In one embodiment, the ionic liquid supported organotin reagent of the invention is of formula (I')

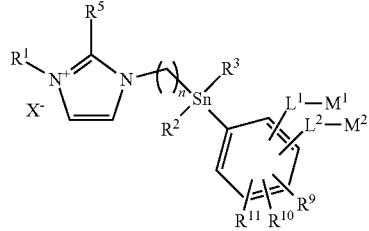

(I')

wherein
$X^-$, n, $R^1$, $R^2$, $R^3$ and $R^5$ are as defined above;
-$L^1$-$M^1$ and -$L^2$-$M^2$ represent each independently -L-M, wherein -L-M is as defined above; and
$R^9$, $R^{19}$ and $R^{11}$ represent each independently a group selected from hydroxyl; linear, cyclic or branched alkyl comprising 1, 2, 3, 4, 5 or 6 carbon atoms; aryl; heteroaryl; heterocyclyl; arylheterocyclyl; alkoxy; halogen; nitro; cyano; azido; aldehyde; boronato; phenyl; $CF_3$; —CH(OH)($CF_3$); —CH(O$CH_2$O$CH_3$)($CF_3$); methylenedioxy; ethylenedioxy; $SO_2$NRR', NRR', COOR, CONRR', NRCOR' wherein R and R' are each independently selected from the group consisting of H, alkyl, cycloalkyl, alkenyl, cycloalkenyl, alkynyl, cycloalkynyl and aryl.

In one embodiment, the ionic liquid supported organotin reagent of the invention is of formula (I' a)

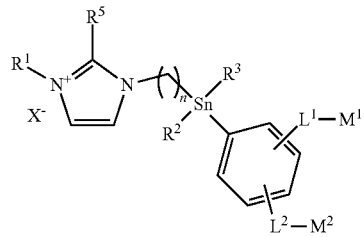

(I'a)

wherein $X^-$, n, $R^1$, $R^2$, $R^3$ and $R^5$ are as defined above, -$L^1$-$M^1$ and -$L^2$-$M^2$ represent each independently -L-M, wherein -L-M is as defined above.

In one embodiment, the ionic liquid supported organotin reagent of the invention is of formula (I'b)

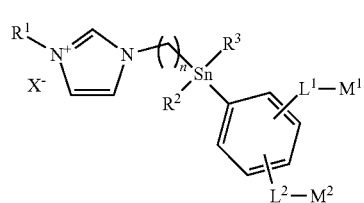

(I'b)

wherein $X^-$, n, $R^1$, $R^2$ and $R^3$ are as defined above, -$L^1$-$M^1$ and -$L^2$-$M^2$ represent each independently -L-M, wherein -L-M is as defined above.

In one embodiment, the ionic liquid supported organotin reagent of the invention is of formula (I' c)

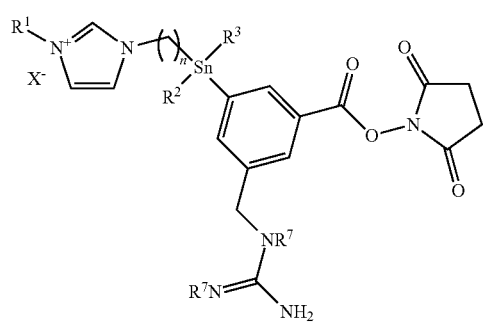

(I'c)

wherein $X^-$, n, $R^1$, $R^2$ and $R^3$ are as defined above, and $R^7$ represent Boc or H.

In one embodiment, the ionic liquid supported organotin reagent of the invention is of formula (I")

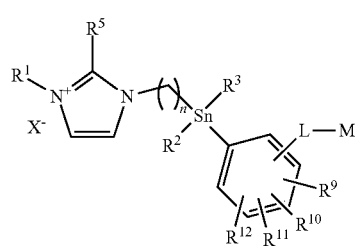

(I")

wherein
X⁻, n, R¹, R², R³, R⁵ and -L-M are as defined above, and R⁹, R¹⁰, R¹¹ and R¹² represent each independently a group selected from hydroxyl; linear, cyclic or branched alkyl comprising 1, 2, 3, 4, 5 or 6 carbon atoms; aryl; heteroaryl; heterocyclyl; arylheterocyclyl; alkoxy; halogen; nitro; cyano; azido; aldehyde; boronato; phenyl; CF₃; —CH(OH)(CF₃); —CH(OCH₂OCH₃)(CF₃); methylenedioxy; ethylenedioxy; SO₂NRR', NRR', COOR, CONRR', NRCOR' wherein R and R' are each independently selected from the group consisting of H, alkyl, cycloalkyl, alkenyl, cycloalkenyl, alkynyl, cycloalkynyl and aryl.

In one embodiment, the ionic liquid supported organotin reagent of the invention is of formula (I"a)

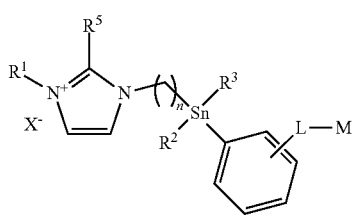

(I"a)

wherein X⁻, n, R¹, R², R³, R⁵ and -L-M are as defined above.

In one embodiment, the ionic liquid supported organotin reagent of the invention is of formula (I"b)

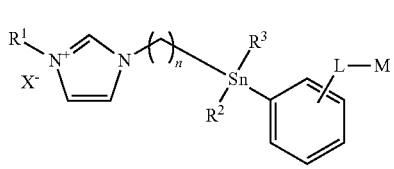

(I"b)

wherein X⁻, n, R¹, R², R³ and -L-M are as defined above.

In one embodiment, R⁴ is an aryl or heteroaryl group substituted by one or more substituents -L-M wherein M represents a reactive function A selected from carboxylic acid, primary amine, secondary amine, tertiary amine, carbamate, amide, maleimide, ester such as for example ethyl or methyl ester, activated ester such as for example succinimidyl, sulfosuccinimidyl, tetrafluorophenyl, pentafluorophenyl or nitrophenyl ester; alkyne, hydroxyl, aldehyde, nitrile, isocyanate, isothiocyanate, phosphine, protected phosphine, thiol, protected thiol, azide, sulphide, azidoalkyl and azidoaryl.

In one embodiment, R⁴ is an aryl or heteroaryl group substituted by one or more substituents -L-M wherein M represents a reactive function A selected from carboxylic acid, nitrile, ester, activated ester, aldehyde, acetal, ketone, ketal, alkyne, azide, alkene, diene, maleimide, protected maleimide, hydroxyl, ether, phenol, 2-aminophenol, thiol, thioester, thioether, thiosulfonate, primary amine, secondary amine, tertiary amine, alkoxyamine, aniline, amide, phosphine, alkyl phosphate, isocyanates, isothiocyanates, hydrazide, hydrazine, tosylate ester, vinyl sulfone, carbamate, carbonate ester, 4-phenyl-1,2,4-triazole-3,5-dione, sulphide, azidoalkyl and azidoaryl.

In a preferred embodiment, R⁴ is an aryl group substituted by one or more substituents -L-A, wherein A is as defined above. In another preferred embodiment, R⁴ is an aryl group substituted by one substituent -L-A, wherein A is as defined above.

In one embodiment, the ionic liquid supported organotin reagent of the invention is of formula (I''')

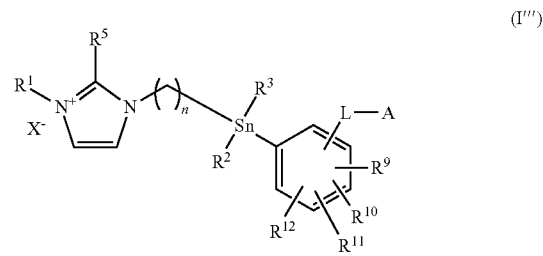

(I''')

wherein X⁻, n, R¹, R², R³, R⁵, -L-A, R⁹, R¹⁰, R¹¹ and R¹² are as defined above.

In one embodiment, the ionic liquid supported organotin reagent of the invention is of formula (I'''a)

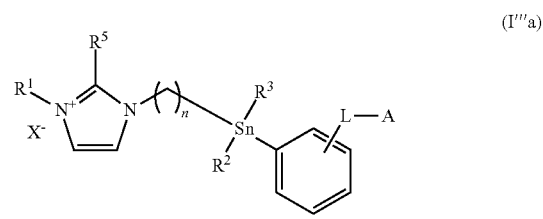

(I'''a)

wherein X⁻, n, R¹, R², R³, R⁵ and -L-A are as defined above.

In one embodiment, the ionic liquid supported organotin reagent of the invention is of formula (I'''b)

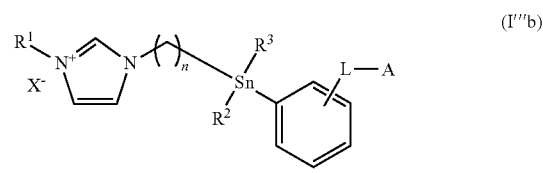

(I'''b)

wherein X⁻, n, R¹, R², R³ and -L-A are as defined above.

In one embodiment, the ionic liquid supported organotin reagent of the invention is of formula (I'''c)

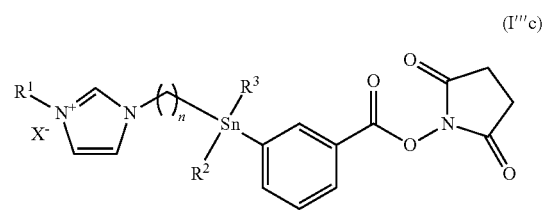

(I'''c)

wherein X⁻, n, R¹, R² and R³ are as defined above.

In one embodiment, the ionic liquid supported organotin reagent of the invention is of formula (I'''d)

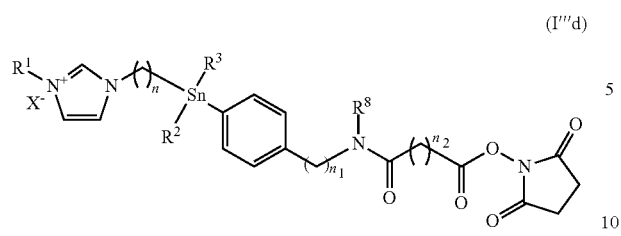

(I'''d)

wherein X⁻, n, R¹, R² and R³ are as defined above; R⁸ represents H or alkyl, preferably H or methyl; $n_1$ and $n_2$ represent each independently 1, 2, 3, or 4 preferably 2.

In one embodiment, the ionic liquid supported organotin reagent of the invention is of formula (I'''e)

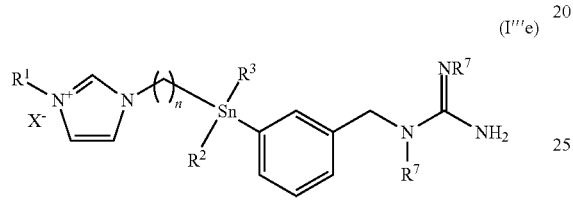

(I'''e)

wherein X⁻, n, R¹, R² and R³ are as defined above and R⁷ represent Boc or H.

In one embodiment, the ionic liquid supported organotin reagent of the invention is of formula (I'''f)

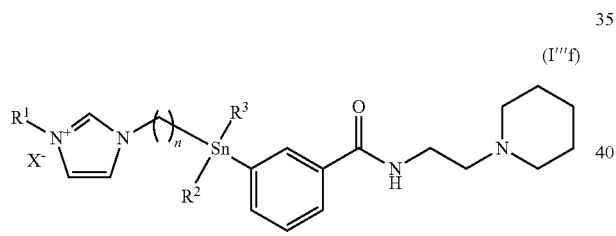

(I'''f)

wherein X⁻, n, R¹, R² and R³ are as defined above.

In a preferred embodiment n is equal to 6, R¹ is ethyl and R² and R³ are both n-butyl.

In an embodiment, the ionic liquid supported organotin reagent of the invention is one of the following compounds:

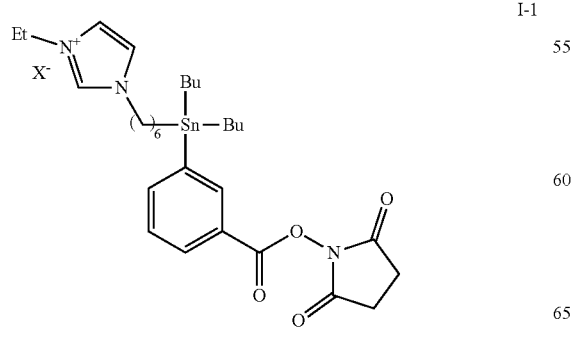

I-1

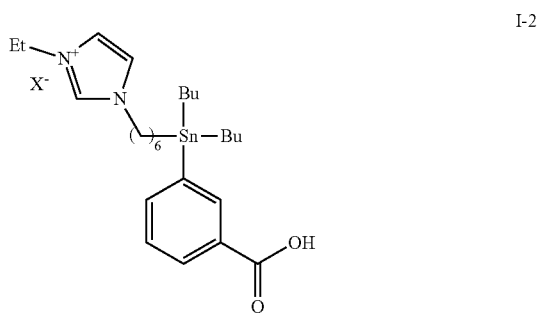

I-2

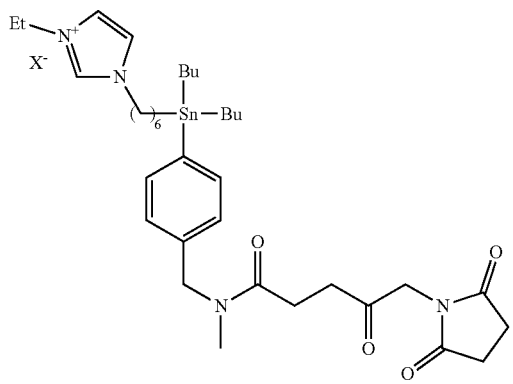

I-3

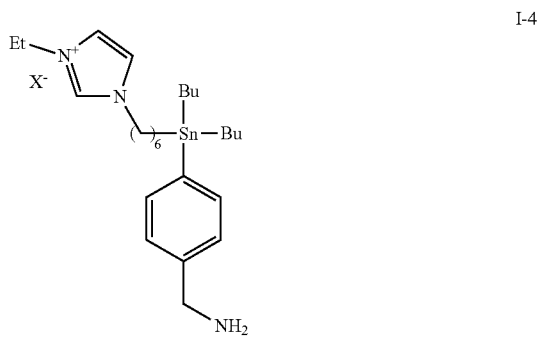

I-4

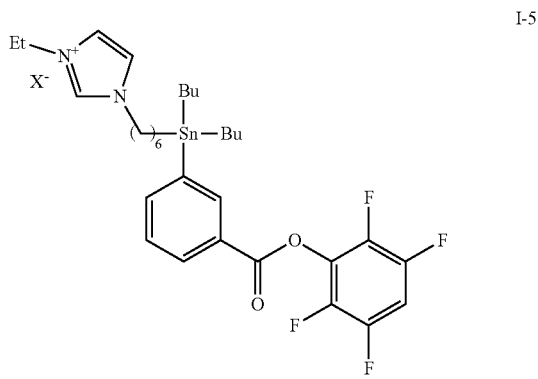

I-5

I-6
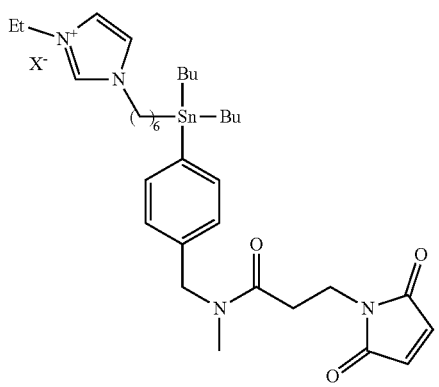

I-7
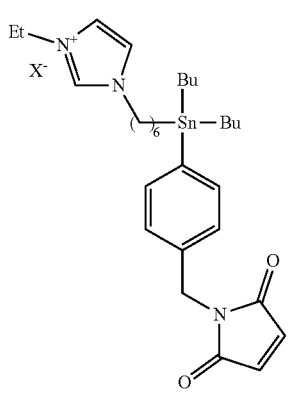

I-8
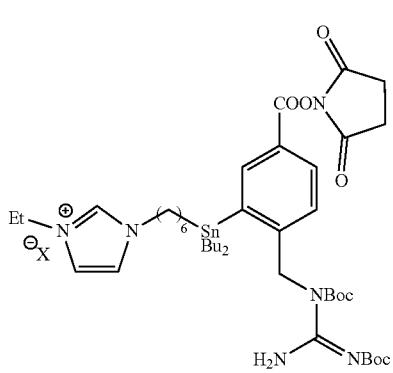

I-9
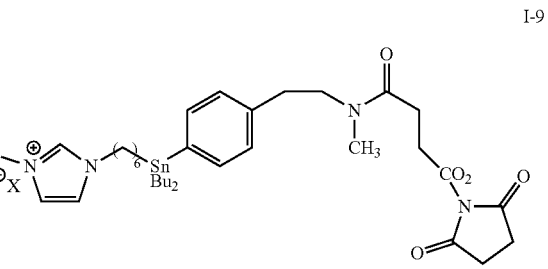

I-10
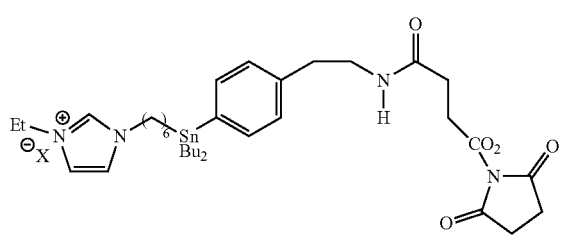

I-11
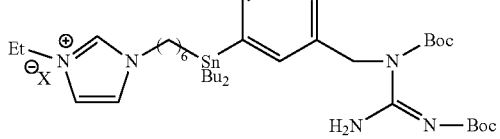

I-12
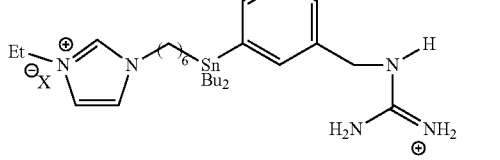

I-13
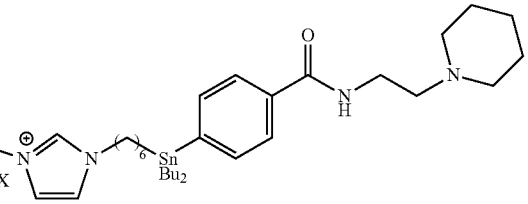

I-14
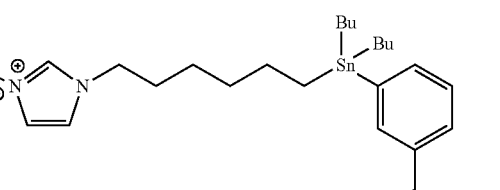

I-15
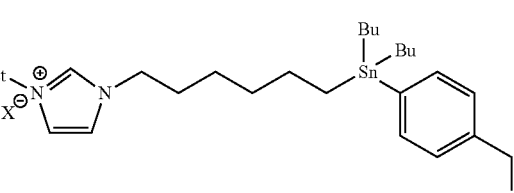

wherein $X^-$ represents $Br^-$, $BF_4^-$ or $PF_6^-$.

Process for Manufacturing the Ionic Liquid Supported Organotin Reagent (I)

The present invention further relates to a process for manufacturing an ionic liquid supported organotin agent (I) as defined above comprising:

1) reacting an activated mixture of zinc and $CoBr_2$ with a compound of formula (IV)

$$R^4\text{—Br} \qquad (IV)$$

wherein $R^4$ is as defined above;

in presence of dibromoethane, to afford the corresponding zinc derivative;

2) reacting the zinc derivative prepared in step 1) with ionic liquid (V)(Br$^-$),

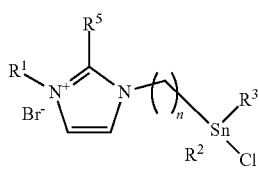

wherein n, $R^1$, $R^2$, $R^3$ and $R^5$ are as defined above;
to form compound of formula (I)(Br⁻)

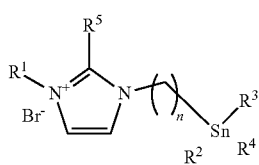

wherein n, $R^1$, $R^2$, $R^3$, $R^4$ and $R^5$ are as defined above;
3) optionally, a methatesis step to exchange Br⁻ to another counterion X⁻ as defined above, to afford compound of formula (I).

According to one embodiment, the process for manufacturing of the invention is for manufacturing an ionic liquid supported organotin agent (I) wherein:

X⁻ represents an anion, preferably an anion selected from the group comprising halide, acetate, trifluoroacetate, triflate (TO, alkylsulfate, sulfonate, tetrafluoroborate ($BF_4^-$), tetraarylborate, hexafluorophosphate ($PF_6^-$), $NO_3^-$, $SbF_6^-$ and derivatives thereof, more preferably $BF_4^-$, $PF_6^-$, Cl⁻, Br⁻, I⁻, $NTf_2^-$, more preferably $BF_4^-$, $PF_6^-$ or Br⁻;

n represents an integer ranging from 3 to 10, preferably n is 4, 5, 6, 7 or 8, more preferably n is 6;

$R^1$ represents an alkyl group, a PEG chain, preferably methyl, ethyl, n-butyl;

$R^2$ and $R^3$ each independently represent an alkyl group, preferably $R^2$ and $R^3$ are both n-butyl;

$R^4$ represents a group selected from aryl and heteroaryl substituted by one or more substituents -L-M wherein:

L represents a linker selected from single bound or a group selected from aryl, alkyl, cycloalkyl, alkenyl, cycloalkenyl, alkynyl, cycloalkynyl;

said groups being optionally substituted by at least one group selected from oxo, thioxo, hydroxyl, ether, carboxylic acid, ester, alkyl, cycloalkyl, alkenyl, cycloalkenyl, heterocyclyl, alkynyl, cycloalkynyl, amine, amide, guanidine, nitro, nitrile, azide, sulfhydryl, sulfide, thioester, thioether, sulfite, sulfate, phosphine, phosphite, phosphate;

said groups being optionally interrupted or terminated by —O—, —S—, —$NR^6$— wherein $R^6$ is H or alkyl, or a combination thereof; and optionally additionally comprising a residue of a reactive group through which L is bounded to M;

M represents:
a hydrogen atom;
a reactive function selected from carboxylic acid, primary amine, secondary amine, tertiary amine, carbamate, amide, maleimide, ester such as for example ethyl or methyl ester, activated ester; alkyne, alcohol, aldehyde, nitrile, isocyanate, isothiocyanate, phosphine, protected phosphine, thiol, protected thiol, azide, sulphide, azidoalkyl and azidoaryl;
a bioactive group selected from amino acid, biogenic amine, peptide, affibody, protein, antibody or fragment thereof, antibody construct such as a for example minibody or, diabody, saccharide, polysaccharide, benzylguanine, biotine, dihydroxyphenylalanine, nucleotide, oligonucleotide, hapten, ligand, enzyme substrate, nanocarrier such as for example nanocapsule, liposome, dendrimer or carbon nanotube and derivatives and combinations thereof;

$R^5$ represents H, alkyl or aryl, preferably H, methyl or phenyl; and comprises:

1) reacting an activated mixture of zinc and $CoBr_2$ with a compound of formula (IV)

$$R^4—Br \quad \text{(IV)}$$

wherein $R^4$ is as defined above;
to afford the corresponding zinc derivative;

2) reacting the zinc derivative prepared in step 1) with ionic liquid (V)(Br⁻),

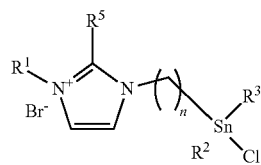

wherein n, $R^1$, $R^2$, $R^3$ and $R^5$ are as defined above;
to form compound of formula (I)(Br⁻)

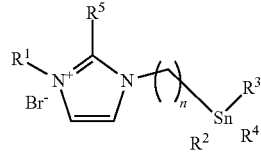

wherein n, $R^1$, $R^2$, $R^3$, $R^4$ and $R^5$ are as defined above;
3) optionally, a methatesis step to exchange Br⁻ to another counterion X⁻ as defined above, to afford compound of formula (I).

According to one embodiment, zinc used in the process of the invention is under the form of zinc dust. According to a specific embodiment, zinc dust has a particle size equal or lower than 50 μm, preferably equal or lower than 30 μm, more preferably equal or lower than 10 μm.

According to one embodiment, activation of zinc and $CoBr_2$ is performed by heating a mixture of zinc and $CoBr_2$ under vacuum at a temperature ranging from 150° C. to 250° C., preferably at about 200° C. Preferably activation is performed for a period of time ranging from 1 hour to 24 hours, preferably about 12 hours. Preferably, activation is performed under argon atmosphere.

According to one embodiment, formation of the zinc derivative (step 1) is performed in presence of dibromoethane, preferably in presence of 0.05 to 0.15 equivalents of dibromoethane. According to a preferred embodiment, step 1 is performed in acetonitrile.

According to one embodiment, the reaction between the zinc derivative and the ionic liquid of formula (V)(Br⁻) (step 2) is performed for a period of time ranging from 1 hour to 24 hours, preferably for 18 hours, at a temperature ranging from room temperature to 100° C., preferably at room temperature.

According to one embodiment, the reaction between the zinc derivative and the ionic liquid (V)(Br⁻) (step 2) is performed in an organic solvent, preferably the organic solvent is selected in the group comprising acetonitrile, THF, DMF. According to a preferred embodiment the reaction between the zinc derivative and the ionic liquid (V)(Br⁻) is performed in anhydrous THF and/or acetonitrile.

According to one embodiment, step 1 and/or step 2 are performed in acidic conditions, such as for example in presence of trifluoroacetic acid.

According to one embodiment, the formation of the zinc derivative (step 1) is performed using zinc dust, preferably activated zinc dust.

Radiolabeling Processes
1) Halodemetallation Reaction in Presence of Ionic Liquid Supported Organotin Reagent (I) of the Invention

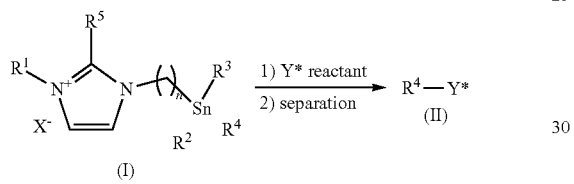

The ionic liquid supported organotin reagent (I) of the present invention may be used in a halodemetallation reaction in presence of an electrophilic reactant comprising the halogen atom, preferably a radioactive halogen atom, more preferably ²¹¹At, ¹²⁵I, ¹³¹I, ¹²⁴I, ¹²³I, ⁷⁶Br, ¹⁸F. The radioactive halogen may be used isotopically pure or as a carrier-added i.e. in a mixture with stable isotope(s).

According to one embodiment, the organotin reagent (I) of the invention is used for the synthesis of halogenated compounds, preferably for the synthesis of radiohalogenated compounds.

The invention thus relates to a labeling process for the manufacturing of a compound of formula (II):

R⁴—Y* wherein
Y* represents a halogen atom, preferably a radiohalogen atom;
R⁴ represents:
an aryl vector; or
a group selected from aryl and heteroaryl substituted by one or more substituents -L-M wherein:
L represents a single bond or a linker selected from aryl, heteroaryl, alkyl, cycloalkyl, alkenyl, cycloalkenyl, alkynyl, cycloalkynyl or a combination thereof;
said groups being optionally substituted by at least one group selected from oxo, thioxo, hydroxyl, ether, carboxylic acid, ester, alkyl, cycloalkyl, alkenyl, cycloalkenyl, heterocyclyl, alkynyl, cycloalkynyl, amine, amide, guanidine, imino, nitro, nitrile, azide, sulfhydryl, sulfide, thioester, thioether, sulfite, sulfate, phosphine, phosphite, phosphate, halogen;
said groups being optionally interrupted or terminated by —O—, —S—, —NR⁶— wherein R⁶ is H or alkyl, or a combination thereof; and
optionally L additionally comprises a residue of a reactive group through which L is bounded to M;
M represents:
a reactive function selected from carboxylic acid, nitrile, ester, activated ester, aldehyde, acetal, ketone, ketal, alkyne, azide, alkene, diene, maleimide, protected maleimide, hydroxyl, ether, phenol, 2-aminophenol, thiol, thioester, thioether, thiosulfonate, primary amine, secondary amine, tertiary amine, alkoxyamine, aniline, amide, phosphine, alkyl phosphate, isocyanates, isothiocyanates, hydrazide, hydrazine, tosylate ester, vinyl sulfone, carbamate, carbonate ester, 4-phenyl-1,2,4-triazole-3,5-dione, sulphide, azidoalkyl and azidoaryl; or
a bioactive group selected from amino acid, biogenic amine, peptide, heteropeptide, protein, antibody or fragment thereof, monobody, affibody, antibody construct such as a for example minibody or diabody, saccharide, polysaccharide, benzylguanine, biotin, avidin, nucleotide, oligonucleotide, microRNA, hapten, aptamer, ligand, enzyme, enzyme substrate, steroid, hormone, porphyrin, neurotransmitters, sympatomimetic drug, vitamin, phosphonate, nanocarrier such as for example nanocapsule, liposome, dendrimer, carbon nanotube and combinations thereof;
said aryl or heteroaryl being optionally further substituted by one or more substituents selected from hydroxyl; linear, cyclic or branched alkyl comprising 1, 2, 3, 4, 5 or 6 carbon atoms; aryl; heteroaryl; heterocyclyl; arylheterocyclyl; alkoxy; halogen; nitro; cyano; azido; aldehyde; boronato; phenyl; CF₃; —CH(OH)(CF₃); —CH(OCH₂OCH₃)(CF₃); methylenedioxy; ethylenedioxy; SO₂NRR', NRR', COOR, CONRR', NRCOR' wherein R and R' each independently selected from the group consisting of H, alkyl, cycloalkyl, alkenyl, cycloalkenyl, alkynyl, cycloalkynyl and aryl;
said process comprising performing a halodemetallation by reacting an electrophilic reactant comprising halogen Y*, with an ionic liquid supported organotin reagent (I) according to the invention.

According to one embodiment, the labeling process of the invention comprises reacting a halogen Y* with an ionic liquid supported organotin reagent (I)

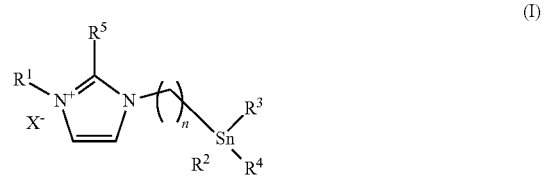

wherein:
X⁻ represents an anion, preferably an anion selected from the group comprising halide, acetate, trifluoroacetate, triflate (TI), alkylsulfate, sulfonate, tetrafluoroborate (BF₄⁻), tetraarylborate, hexafluorophosphate (PF₆⁻), NO₃⁻, SbF₆⁻ and derivatives thereof, more preferably BF₄⁻, PF₆⁻, Cl⁻, Br⁻, I⁻, NTf₂⁻, more preferably BF₄⁻, PF₆⁻ or Br⁻;

n represents an integer ranging from 3 to 10, preferably n is 4, 5, 6, 7 or 8, more preferably n is 6;

$R^1$ represents an alkyl group, a PEG chain, preferably methyl, ethyl, n-butyl;

$R^2$ and $R^3$ each independently represent an alkyl group, preferably $R^2$ and $R^3$ are both n-butyl;

$R^4$ represents a group selected from aryl and heteroaryl substituted by one or more substituents -L-M wherein:

L represents a linker selected from single bound or a group selected from aryl, alkyl, cycloalkyl, alkenyl, cycloalkenyl, alkynyl, cycloalkynyl;

said groups being optionally substituted by at least one group selected from oxo, thioxo, hydroxyl, ether, carboxylic acid, ester, alkyl, cycloalkyl, alkenyl, cycloalkenyl, heterocyclyl, alkynyl, cycloalkynyl, amine, amide, guanidine, nitro, nitrile, azide, sulfhydryl, sulfide, thioester, thioether, sulfite, sulfate, phosphine, phosphite, phosphate;

said groups being optionally interrupted or terminated by —O—, —S—, —$NR^6$— wherein $R^6$ is H or alkyl, or a combination thereof; and optionally additionally comprising a residue of a reactive group through which L is bounded to M;

M represents:

a hydrogen atom;

a reactive function selected from carboxylic acid, primary amine, secondary amine, tertiary amine, carbamate, amide, maleimide, ester such as for example ethyl or methyl ester, activated ester; alkyne, alcohol, aldehyde, nitrile, isocyanate, isothiocyanate, phosphine, protected phosphine, thiol, protected thiol, azide, sulphide, azidoalkyl and azidoaryl;

a bioactive group selected from amino acid, biogenic amine, peptide, affibody, protein, antibody or fragment thereof, antibody construct such as a for example minibody or, diabody, saccharide, polysaccharide, benzylguanine, biotine, dihydroxyphenylalanine, nucleotide, oligonucleotide, hapten, ligand, enzyme substrate, nanocarrier such as for example nanocapsule, liposome, dendrimer or carbon nanotube and derivatives and combinations thereof;

$R^5$ represents H, alkyl or aryl, preferably H, methyl or phenyl;

to form compound of formula (II) $R^4$—Y*, wherein $R^4$ is as described above.

In one embodiment, the halogen Y* is a radiohalogen, preferably Y* is a radiohalogen selected from the group comprising $^{125}I$, $^{123}I$, $^{131}I$, $^{124}I$, $^{211}At$, $^{76}Br$, $^{18}F$, more preferably Y* is $^{211}At$ or $^{18}F$.

In one embodiment, the halogen Y* is a radiohalogen, preferably Y* is a radiohalogen selected from the group comprising $^{125}I$, $^{131}I$, $^{124}I$, $^{211}At$, $^{18}F$, more preferably Y* is $^{211}At$.

In one embodiment, the ionic liquid supported organotin reagent used in the labeling process of the invention is of formula (I″)

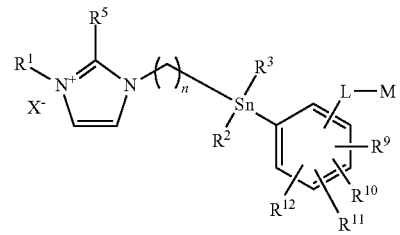

wherein $X^-$, n, $R^1$, $R^2$, $R^3$, $R^5$, -L-M, $R^9$, $R^{10}$, $R^{11}$ and $R^{12}$ are as defined above.

In one embodiment, the ionic liquid supported organotin reagent used in the labeling process of the invention is of formula (I″a)

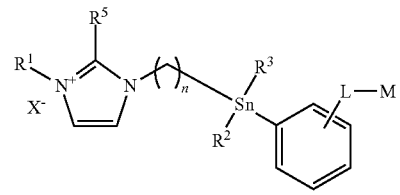

wherein $X^-$, n, $R^1$, $R^2$, $R^3$, $R^5$ and -L-M are as defined above.

In one embodiment, compound $R^4$—Y* is of formula (II″)

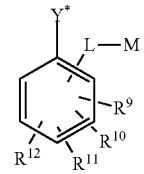

wherein Y*, -L-M, $R^9$, $R^{10}$, $R^{11}$ and $R^{12}$ are as defined above.

In one embodiment, compound $R^4$—Y* is of formula (II″a)

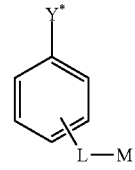

wherein Y* and -L-M are as defined above.

The invention thus relates to a process for the synthesis of a compound of formula (II″)

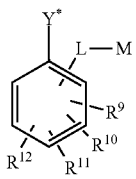

(II")

wherein Y*, -L-M, R⁹, R¹⁰, R¹¹ and R¹² are as defined above said process comprising performing a halodemetallation by reacting an electrophilic reactant comprising halogen Y*, with an ionic liquid supported organotin reagent (I") to form compound of formula (II").

According to one embodiment, the invention also relates to a process for the synthesis of a compound of formula (II"a)

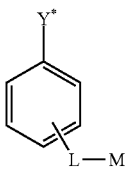

(II"a)

wherein:
Y* represents a halogen, preferably a radiohalogen;
L represents a linker selected from single bound or a group selected from aryl, alkyl, cycloalkyl, alkenyl, cycloalkenyl, alkynyl, cycloalkynyl;
said groups being optionally substituted by at least one group selected from oxo, thioxo, hydroxyl, ether, carboxylic acid, ester, alkyl, cycloalkyl, alkenyl, cycloalkenyl, heterocyclyl, alkynyl, cycloalkynyl, amine, amide, guanidine, nitro, nitrile, azide, sulfhydryl, sulfide, thioester, thioether, sulfite, sulfate, phosphine, phosphite, phosphate;
said groups being optionally interrupted or terminated by —O—, —S—, —NR⁶— wherein R⁶ is H or alkyl, or a combination thereof; and
optionally additionally comprising a residue of a reactive group through which L is bounded to M;
M represents:
a hydrogen atom;
a reactive function selected from carboxylic acid, primary amine, secondary amine, tertiary amine, carbamate, amide, maleimide, ester such as for example ethyl or methyl ester, activated ester; alkyne, alcohol, aldehyde, nitrile, isocyanate, isothiocyanate, phosphine, protected phosphine, thiol, protected thiol, azide, sulphide, azidoalkyl and azidoaryl;
a bioactive group selected from amino acid, biogenic amine, peptide, affibody, protein, antibody or fragment thereof, antibody construct such as a for example minibody or, diabody, saccharide, polysaccharide, benzylguanine, biotine, dihydroxyphenylalanine, nucleotide, oligonucleotide, hapten, ligand, enzyme substrate, nanocarrier such as for example nanocapsule, liposome, dendrimer or carbon nanotube and derivatives and combinations thereof.

comprising:
reacting a halogen Y* with compound as defined above, to form compound of formula (II"a).

According to a preferred embodiment, in compound (II), M represents a reactive function, and the process further comprises a subsequent step of reacting compound (II) with a vector selected from amino acid, biogenic amine, peptide, heteropeptide, protein, antibody or fragment thereof, monobody, affibody, antibody construct such as a for example minibody or diabody, saccharide, polysaccharide, benzylguanine, biotin, avidin, nucleotide, oligonucleotide, microRNA, hapten, aptamer, ligand, enzyme, enzyme substrate, steroid, hormone, porphyrin, neurotransmitters, sympatomimetic drug, vitamin, phosphonate, nanocarrier such as for example nanocapsule, liposome, dendrimer, carbon nanotube; said vector comprising at least one reactive function B; said reactive function B being able to react with the reactive function of compound (II), leading to the labeled vector (III).

According to a preferred embodiment, in compound (II), M represents a reactive function, and the process further comprises a subsequent step of reacting compound (II) with a vector selected from amino acid, biogenic amine, peptide, affibody, protein, antibody or fragment thereof, antibody construct such as a for example minibody or, diabody, saccharide, polysaccharide, benzylguanine, biotine, dihydroxyphenylalanine, nucleotide, oligonucleotide, hapten, ligand, enzyme substrate, nanocarrier such as for example nanocapsule, liposome, dendrimer or carbon nanotube and derivatives and combinations thereof; said vector comprising at least one reactive function B; said reactive function B being able to react with the reactive function of compound (II), leading to the labeled vector (III).

In one embodiment, compound R⁴—Y* is of formula (II''')

(II''')

wherein Y*, L, R⁹, R¹⁰, R¹¹ and R¹² are as defined above and A represents a reactive function selected from a reactive function selected from carboxylic acid, nitrile, ester, activated ester, aldehyde, acetal, ketone, ketal, alkyne, azide, alkene, diene, maleimide, protected maleimide, hydroxyl, ether, phenol, 2-aminophenol, thiol, thioester, thioether, thiosulfonate, primary amine, secondary amine, tertiary amine, alkoxyamine, aniline, amide, phosphine, alkyl phosphate, isocyanates, isothiocyanates, hydrazide, hydrazine, tosylate ester, vinyl sulfone, carbamate, carbonate ester, 4-phenyl-1,2,4-triazole-3,5-dione, sulphide, azidoalkyl and azidoaryl.

In one embodiment, compound R⁴—Y* is of formula (II'''a)

(II'''a)

wherein Y* and L are as defined above and A represents a reactive function selected from a reactive function selected from carboxylic acid, nitrile, ester, activated ester, aldehyde, acetal, ketone, ketal, alkyne, azide, alkene, diene, maleimide, protected maleimide, hydroxyl, ether, phenol, 2-aminophenol, thiol, thioester, thioether, thiosulfonate, primary amine, secondary amine, tertiary amine, alkoxyamine, aniline, amide, phosphine, alkyl phosphate, isocyanates, isothiocyanates, hydrazide, hydrazine, tosylate ester, vinyl sulfone, carbamate, carbonate ester, 4-phenyl-1,2,4-triazole-3,5-dione, sulphide, azidoalkyl and azidoaryl.

According to a specific embodiment, A represents a reactive function selected from carboxylic acid, primary amine, secondary amine, tertiary amine, carbamate, amide, maleimide, ester such as for example ethyl or methyl ester, activated ester such as for example succinimidyl, sulfosuccinimidyl, tetrafluorophenyl, pentafluorophenyl or nitrophenyl ester; alkyne, alcohol, aldehyde, nitrile, isocyanate, isothiocyanate, phosphine, protected phosphine, thiol, protected thiol, azide, sulphide, azidoalkyl and azidoaryl.

Electrophilic Reactant for Halodemetallation by Y*

The labeling process of the invention comprises performing a halodemetallation reaction by reacting an electrophilic reactant comprising halogen Y* with the ionic liquid of the invention.

In one embodiment, the electrophilic reactant involved in the halodemetallation reaction is generated in situ in the reaction medium from a "starting reactant" comprising halogen Y*.

According to one embodiment, in the electrophilic reactant used in the labeling process of the invention, Y* is a radiohalogen, preferably a radiohalogen selected from the group comprising $^{18}$F, $^{76}$Br, $^{125}$I, $^{131}$I, $^{124}$I, $^{123}$I, $^{211}$At, more preferably Y* is $^{211}$At. When Y* is a radiohalogen, the "starting reactant" and/or the "electrophilic reactant" is radioactive and may be produced by irradiation and further treatments such as liquid or solid phase extraction, distillation, thermal diffusion potentially combined to recovery in a solvent or recovery in a solvent then treatment to obtain a dry residue and/or other purification method.

In one embodiment, in the electrophilic reactant used in the labeling process of the invention, Y* is a radiohalogen, preferably $^{76}$Br, $^{125}$I, $^{131}$I, $^{124}$I, $^{211}$At and the labeling process of the invention need the help of a catalyst selected in, but not limited to, the group of onium salts.

According to one embodiment, when Y* is bromine, preferably $^{76}$Br, the electrophilic reactant may be Br$_2$, (i.e. Br$^+$Br$^-$ wherein half reacts).

According to another embodiment, when Y* is bromine, preferably $^{76}$Br, the electrophilic reactant may be a species comprising Br(+I), such as for example BrCl.

According to another embodiment, when Y* is bromine, preferably $^{76}$Br, the electrophilic reactant may be a species comprising Br(+I), such as for example BrCl, obtained by oxidation of a "starting reactant" which may be:
 a species comprising Br(−I), such as for example NH$_4$Br or HBr; or
 a species comprising Br(0), such as for example Br$_2$; or
 a mixture thereof.

According to one embodiment, the oxidation of the "starting reactant" is performed in presence of an oxidizing agent selected from N-chlorosuccinimide (NCS), N-iodosuccinimide, N-Bromosuccinimide, Chloramine-T, hydrogen peroxide, sodium hypochlorite, terbutylhydroperoxyde; in presence or not of a catalyst.

According to one embodiment, when Y* is Bromine, preferably $^{76}$Br, the labeling process of the invention may comprise a step of reduction after the substitution with tin supported by the ionic liquid of the invention. According to one embodiment, reduction may be performed in presence of a reducing agent selected from, but not limited to sodium metabisulfite, sodium sulfite, cysteine or dithiothreitol.

In one embodiment, in the electrophilic reactant used in the labeling process of the invention, Y* is a radiohalogen, preferably $^{76}$Br, and the labeling process of the invention is performed in presence of an oxidizing agent selected from N-chlorosuccinimide (NCS), N-iodosuccinimide, N-Bromosuccinimide, Chloramine-T, hydrogen peroxide, sodium hypochlorite, terbutylhydroperoxyde; in presence or not of a catalyst.

In one embodiment, in the electrophilic reactant used in the labeling process of the invention, Y* is a radiohalogen, preferably $^{76}$Br, and the labeling process of the invention is performed in presence or not of a catalyst.

According to one embodiment, when Y* is iodine, preferably $^{125}$I, $^{131}$I, $^{124}$I or $^{123}$I, the electrophilic reactant may be I$_2$, (i.e. I$^+$I$^-$ wherein half reacts).

According to another embodiment, when Y* is iodine, preferably $^{125}$I, $^{131}$I, $^{124}$I or $^{123}$I, the electrophilic reactant may be a species comprising I(+I), such as for example ICl, According to another embodiment, when Y* is iodine, preferably $^{125}$I, $^{131}$I, $^{124}$I or $^{123}$I, the electrophilic reactant may be a species comprising I(+I), such as for example ICl, obtained by oxidation of a "starting reactant" which may be:
 a species comprising I(−I), such as for example NaI; or
 a species comprising I(0), such as for example I$_2$; or
 a mixture thereof.

According to one embodiment, the oxidation of the "starting reactant" is performed in presence of an oxidizing agent selected from N-chlorosuccinimide (NCS), N-iodosuccinimide, N-Bromosuccinimide, Chloramine-T, hydrogen peroxide, sodium hypochlorite, terbutylhydroperoxyde; in presence or not of a catalyst.

According to one embodiment, when Y* is iodine, preferably $^{125}$I, $^{131}$I, $^{124}$I or $^{123}$I, the labeling process of the invention may comprise a step of reduction after the substitution with tin supported by the ionic liquid of the invention. According to one embodiment, reduction may be performed in presence of a reducing agent selected from, but not limited to sodium metabisulfite, sodium sulfite, cysteine or dithiothreitol.

In one embodiment, in the electrophilic reactant used in the labeling process of the invention, Y* is a radiohalogen, preferably $^{125}$I, and the labeling process of the invention is performed in presence of an oxidizing agent selected from N-chlorosuccinimide (NCS), N-iodosuccinimide, N-Bromosuccinimide, Chloramine-T, hydrogen peroxide, sodium hypochlorite, terbutylhydroperoxyde; in presence or not of a catalyst.

In one embodiment, in the electrophilic reactant used in the labeling process of the invention, Y* is a radiohalogen, preferably $^{125}$I, and the labeling process of the invention is performed in presence or not of a catalyst.

In one embodiment, Y* is a radiohalogen, preferably $^{125}$I, the labeling process of the invention may comprise a step of reduction after the substitution with tin supported by the ionic liquid of the invention. According to one embodiment, reduction may be performed in presence of a reducing agent selected from sodium metabisulfite, sodium sulfite, cysteine or dithiothreitol.

In one embodiment, in the electrophilic reactant used in the labeling process of the invention, Y* is a radiohalogen, preferably $^{131}$I, and the labeling process of the invention is performed in presence of an oxidizing agent selected from N-chlorosuccinimide (NCS), N-iodosuccinimide, N-Bromosuccinimide, Chloramine-T, hydrogen peroxide, sodium hypochlorite, terbutylhydroperoxyde; in presence or not of a catalyst.

In one embodiment, in the electrophilic reactant used in the labeling process of the invention, Y* is a radiohalogen, preferably $^{131}$I, and the labeling process of the invention is performed in presence or not of a catalyst.

In one embodiment, Y* is a radiohalogen, preferably $^{131}$I, the labeling process of the invention may comprise a step of reduction after the substitution with tin supported by the ionic liquid of the invention. According to one embodiment, reduction may be performed in presence of a reducing agent selected from sodium metabisulfite, sodium sulfite, cysteine or dithiothreitol.

In one embodiment, in the electrophilic reactant used in the labeling process of the invention, Y* is a radiohalogen, preferably $^{124}$I, and the labeling process of the invention is performed in presence of an oxidizing agent selected from N-chlorosuccinimide (NCS), N-iodosuccinimide, N-Bromosuccinimide, Chloramine-T, hydrogen peroxide, sodium hypochlorite, terbutylhydroperoxyde; in presence or not of a catalyst.

In one embodiment, in the electrophilic reactant used in the labeling process of the invention, Y* is a radiohalogen, preferably $^{124}$I and the labeling process of the invention is performed in presence or not of a catalyst.

In one embodiment, Y* is a radiohalogen, preferably $^{124}$I, the labeling process of the invention may comprise a step of reduction after the substitution with tin supported by the ionic liquid of the invention. According to one embodiment, reduction may be performed in presence of a reducing agent selected from sodium metabisulfite, sodium sulfite, cysteine or dithiothreitol.

In one embodiment, in the electrophilic reactant used in the labeling process of the invention, Y* is a radiohalogen, preferably $^{123}$I, and the labeling process of the invention is performed in presence of an oxidizing agent selected from N-chlorosuccinimide (NCS), N-iodosuccinimide, N-Bromosuccinimide, Chloramine-T, hydrogen peroxide, sodium hypochlorite, terbutylhydroperoxyde; in presence or not of a catalyst.

In one embodiment, in the electrophilic reactant used in the labeling process of the invention, Y* is a radiohalogen, preferably $^{123}$I, and the labeling process of the invention is performed in presence or not of a catalyst.

In one embodiment, Y* is a radiohalogen, preferably $^{123}$I, the labeling process of the invention may comprise a step of reduction after the substitution with tin supported by the ionic liquid of the invention. According to one embodiment, reduction may be performed in presence of a reducing agent selected from sodium metabisulfite, sodium sulfite, cysteine or dithiothreitol.

Relative to astatine, it should be noted that the form of the species comprising $^{211}$At is not well known in the art. It may be At$^-$, At(0) (but it is not determined if it is under the form of molecular At or At$_2$), At$^+$, AtO$^-$, AtO$^+$ or a complex formed by these species with solvent, or a mixture thereof. Compositions and proportions of such mixtures depend from experimental conditions used to produce $^{211}$At, such as for example the method of extraction, solvents, additives, contaminants present in the solvent, moisture content, radiolysis rate. These species are disclosed in Champion J et al, J Phys Chem A. 2013; 117(9):1983-90; A. Serov et al., Radiochimica Acta 2011, 99 (9), 593; C. Alliot et al., Radiochim. Acta 2009, 97, 161; O. R. Pozzi et al., J Nucl Med July 2007, 48, 1190; O. R. Pozzi et al., J Nucl Med 2005, 46, 1393; Visser, G. W., Radiochim. Acta 47, 97 (1989); Visser, G. W., Diemer, E. L.: Radiochim. Acta 1983, 33, 145; J. Champion et al., J. Phys. Chem. A 2009, 114, 576.

The formation of complexes between astatine species and solvent as described in Visser, G. W.: Radiochim. Acta 47, 97 (1989); Visser, G. W., Diemer, E. L.: Radiochim. Acta 1983, 33, 145; C. Alliot et al., Radiochim. Acta 2009, 97, 161.

According to one embodiment, when Y* is astatine, preferably $^{211}$At, A the electrophilic reactant may be At$_2$, (i.e. At$^+$At$^-$) wherein half reacts).

According to one embodiment, when Y* is astatine, preferably $^{211}$At, A the electrophilic reactant may be a species comprising At(+X), wherein X may be equal to 1 (At$^+$) or equal to 3 (AtO$^+$), such as for example AtCl, AtI, AtBr, AtNO$_3$, AtClO$_4$, AtSO$_4$Na, AtSO$_4$K, AtOH, AtOCl AtOBr, AtOI, or complexes formed by these species with solvent.

According to an embodiment, when Y* is astatine, preferably $^{211}$At, A the electrophilic reactant may be a species comprising At(+I), such as for example AtCl or AtI, obtained by oxidation of a "starting reactant" which may be:
  a species comprising At(−I), such as for example AtNa, AtK or complexes formed by these species with solvent; or
  a species comprising At(0), such as for example molecular At(0), At$_2$ or complexes formed by these species with solvent; or
  a mixture thereof.

According to another embodiment, when Y* is astatine, preferably $^{211}$At, the electrophilic reactant may be a species comprising At(+III) AtOCl AtOBr, AtOI, or complexes formed by these species with solvent.

Such electrophilic reactants may be obtained from "starting reactants" which may be:
  a species comprising At(−I), such as for example AtNa, AtK or complexes formed by these species with solvent; or
  a species comprising At(0), such as for example At(0), At$_2$ or complexes formed by these species with solvent; or
  a species comprising At(+I such as for example AtCl, AtI, AtBr, AtNO$_3$, AtClO$_4$, AtSO$_4$Na, AtSO$_4$K, AtCl$_2$Na, AtBr$_2$Na, AtI$_2$Na, AtONa, AtOK, AtOH, or complexes formed by these species with solvent; or
  a mixture thereof.

According to one embodiment, the oxidation of the "starting reactant" is performed in presence of an oxidizing agent selected from N-chlorosuccinimide (NCS), N-iodosuccinimide (NIS), N-Bromosuccinimide, Chloramine-T, hydrogen peroxide, sodium hypochlorite, terbutylhydroperoxyde; potassium dichromate in presence or not of a catalyst.

According to one embodiment, when Y* is astatine, preferably $^{211}$At, the labeling process of the invention may comprise a step of reduction after the substitution with tin supported by the ionic liquid of the invention. According to one embodiment, reduction may be performed in presence of a reducing agent selected from, but not limited to sodium metabisulfite, sodium sulfite, cysteine or dithiothreitol.

In one embodiment, in the electrophilic reactant used in the labeling process of the invention, Y* is a radiohalogen, preferably $^{211}$At, and the labeling process of the invention is performed in presence of an oxidizing agent selected from N-chlorosuccinimide (NCS), N-iodosuccinimide, N-Bromosuccinimide, Chloramine-T, hydrogen peroxide, sodium hypochlorite, terbutylhydroperoxyde; potassium dichromate in presence or not of a catalyst.

In one embodiment, in the electrophilic reactant used in the labeling process of the invention, Y* is a radiohalogen, preferably $^{211}$At, and the labeling process of the invention is performed in presence or not of a catalyst.

According to one embodiment, when Y* is fluorine, preferably $^{18}$F, the electrophilic reactant may be a species comprising F(+I), such as for example FOAc or F18-selectfluor and its derivatives.

Such electrophilic reactants may be obtained from a "starting reactant" which may be:
  a species comprising F(−I), such as for example KF; or
  a species comprising F(0), such as for example $F_2$; or
  a mixture thereof.

In one embodiment, in the electrophilic reactant used in the labeling process of the invention, Y* is a radiohalogen, preferably $^{18}$F and the labeling process of the invention need the help of a catalyst selected in, but not limited to, the group of copper, nickel, palladium and silver complexes.

In one embodiment, in the electrophilic reactant used in the labeling process of the invention, Y* is a radiohalogen, preferably $^{18}$F, and the labeling process of the invention is performed with or without catalyst and any chemical species including [$^{18}$F]F(+I) in their structure such species are described in, but not limited to, Nyffeler, et al., Angew. Chem. Int. Ed., 2005, 44, 192-212; Yingda et al., JACS, 2013, 135(12), 4648-4651; Stenhagen et al., Chem. Comm., 2013, 49(14), 1386; Eskola et al., Eur. J. Nucl. Med. Mol. Im., 2012, 39, (5), 800-810; Furuya et al., JACS, 2009, 131(5), 1662-1663; Eskola et al., Nucl. Med. Biol., 2004, 31(1), 103-110; Fischer et al., Forschungszentrum Rossendorf e.V., [Bericht], 1997, 200, 174-176; Namavari et al., Appl. Rad. Isotopes, 1993, 44(3), 527-536; Tius et al., Synth. Comm., 1992, 22(10), 1461-1471; Bryce, Martin et al., Bulletin de la Société Chimique de France, 1986, 939-932; Adam et al., J. Fluorine Chem., 1984, 25 (3), 329-337; U.S. Pat. No. 5,510,522; WO 2010059943; WO 2001027122; DE 19928911.

In one embodiment, in the electrophilic reactant used in the labeling process of the invention, Y* is a radiohalogen, preferably $^{18}$F, and the labeling process of the invention is performed with [$^{18}$F]$F_2$; with or without catalyst.

In one embodiment, in the electrophilic reactant used in the labeling process of the invention, Y* is a radiohalogen, preferably $^{18}$F, and the labeling process of the invention is performed with [$^{18}$F]F$^-$ in the presence of an oxidizing agent selected in, but not limited to, the group of hypervalent iodine species, with or without catalyst such as described in Geary et al., Chem. Comm., 2013, 49, 9263-9265; Lee et al., JACS., 2012, 134, 17456-17458; Lee et al., Science 2011, 334, 639-642.

In one embodiment, in the electrophilic reactant comprising halogen Y* used in the labeling process of the invention, Y* is a radiohalogen, preferably $^{18}$F, and the labeling process of the invention is performed with [$^{18}$F]$F_2$ in presence of, but not limited to, acetate, perchlorate, triflate salts, Selectfluor salts and their derivatives; with or without catalyst. Selectfluor refers to 1-Chloromethyl-4-fluoro-1,4-diazoniabicyclo[2.2.2]octane bis(tetrafluoroborate).

In another embodiment, the labeling process of the invention is performed without adding an oxidizing agent and in presence of a catalyst. In an alternative embodiment, the labeling process of the invention is performed without adding an oxidizing agent and in the absence of catalyst.

In another embodiment, a reducing agent is added at the end of the reaction. The reducing step is performed in the presence of, but not limited to, sodium sulfite, sodium metabisulfite, cysteine or dithiothreitol. In another embodiment, the labeling process is performed without using a reducing agent.

According to one embodiment, compound (II) obtained by the labeling process of the invention is easily separated from the reaction medium by filtration on a silica cartridge, preferably on normal phase silica cartridge.

According to another embodiment, compound (II) obtained by the labeling process of the invention is easily separated from the reaction medium by filtration on a silica cartridge, preferably on C18 grafted silica cartridge.

According to one embodiment, compound (II) obtained by the labeling process of the invention is easily separated from the reaction medium by liquid/liquid extraction and recovered in the aqueous phase.

According to one embodiment, compound (II) obtained by the labeling process of the invention is easily separated from the reaction medium by liquid/liquid extraction and recovered in the organic phase.

In one embodiment, the labeling process of the invention comprises the following steps:
  adding the ionic liquid supported organotin reagent (I) of the invention solubilized in a solvent;
  adding an oxidizing agent solubilized in a solvent; and
  adding the Y* reactant solubilized in a solvent.

In another embodiment, the labeling process of the invention comprises the following steps:
  adding the ionic liquid supported organotin reagent (I) of the invention solubilized in a solvent; and
  adding the Y* reactant solubilized in a solvent.

In an embodiment, the solvent used in the labeling process of the invention is selected from methanol, ethanol, acetonitrile, diisopropyl ether, diethyl ether, dimethylformamide, dimethylsulfoxide, ethyl acetate, dichloromethane, dichloroethane, chloroform, aqueous solutions, acetic acid, a ionic liquid or a mixture of these solvents. In an embodiment, the solvent used in the labeling process of the invention is selected from methanol, acetonitrile, diisopropyl ether, dichloromethane, chloroform, aqueous solutions, acetic acid or a mixture of these solvents.

In another embodiment, the labeling process of the invention comprises adding the ionic liquid supported organotin reagent (I) of the invention solubilized in a solvent and an oxidizing agent solubilized in a solvent to the Y* reactant (dry residue).

In another embodiment, the labeling process of the invention comprises adding the ionic liquid supported organotin reagent (I) of the invention solubilized in a solvent to the Y* reactant (dry residue).

In a preferred embodiment, the labeling process of the invention comprises reacting an electrophilic reactant comprising $^{211}$At, with an ionic liquid supported organotin reagent (I'''c)

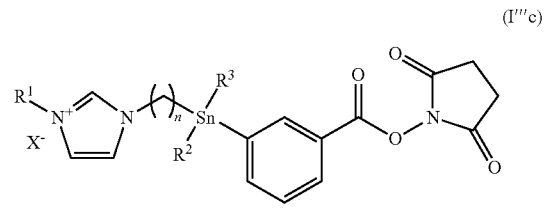

(I'''c)

wherein X$^-$, n, R$^1$, R$^2$ and R$^3$ are as defined above;

to form radiolabeled succinimidyl astatobenzoate (SAB) of formula [²¹¹At]-II-1

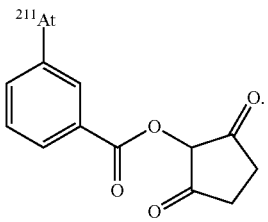

In a specific embodiment, the labeling process of the invention comprises the following steps:
adding a starting reactant comprising astatine-211 solubilized in methanol;
adding N-chlorosuccinimide (NCS) solubilized in Methanol/Acetic Acid (95:5); and
adding the ionic liquid supported organotin reagent (I) of the invention solubilized in Methanol/Acetic Acid (95:5).

In this embodiment, the starting reactant comprising astatine-211 is oxidized by NCS to form the electrophilic reactant comprising astatine-211.

In a specific embodiment, the labeling process of the invention comprises the following steps:
adding the ionic liquid supported organotin reagent (I) of the invention solubilized in Methanol/Acetic Acid (95:5); and
adding the electrophilic reactant comprising astatine-211 solubilized in methanol.

According to one embodiment the labeling reaction is performed at a temperature ranging from 15° C. to 100° C., preferably at room temperature, for a period of time ranging from 1 to 90 minutes, preferably for 30 minutes.

In a preferred embodiment, the labeling process of the invention comprises reacting an electrophilic reactant comprising ¹²⁵I with an ionic liquid supported organotin reagent (I'''c)

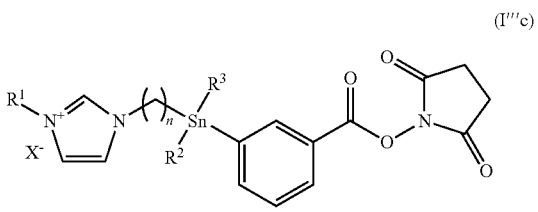

wherein X⁻, n, R¹, R² and R³ are as defined above;
to form radiolabeled succinimidyl iodobenzoate (SIB) of formula [¹²⁵I]-II-1

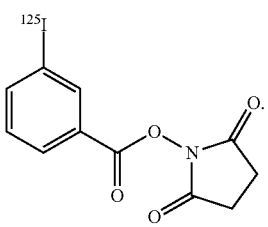 [SMILES: O=C(ON1C(=O)CCC1=O)c1cccc([125I])c1]

In a specific embodiment, the labeling process of the invention comprises the following steps:
adding a starting reactant comprising Iodine-125 solubilized in aqueous sodium hydroxide (pH 7 to 13);
adding N-chlorosuccinimide NCS solubilized in Methanol/Acetic Acid (95:5); and
adding the ionic liquid supported organotin reagent (I) of the invention solubilized in Methanol/Acetic Acid (95:5).

In this embodiment, the starting reactant comprising iodine-125 is oxidized by NCS to form the electrophilic reactant comprising iodine-125.

In another particular embodiment, the labeling process of the invention comprises the following steps:
adding the ionic liquid supported organotin reagent (I) of the invention solubilized in Methanol/Acetic Acid (95:5); and
adding the electrophilic reactant comprising Iodine-125 solubilized in aqueous sodium hydroxide (pH 7 to 13).

2) Labeling of a vector to form a radiopharmaceutical

When compounds of formula (II) (R⁴—Y*) obtained by the labeling process of the invention comprise a radiohalogen and at least one functional group having targeting properties, they are directly considered as radiopharmaceuticals. This is especially the case when R⁴ is substituted by -L-M wherein M is a bioactive group.

When compounds of formula (II) (R⁴—Y*) obtained by the labeling process of the invention comprise a radiohalogen and at least one reactive function, they may be considered as radiolabeled precursors and they may be used as reactant to label a vector to form a radiopharmaceutical (III) as schematically represented below:

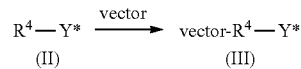

According to a specific embodiment, the ionic liquid reagent is of formula (I'''a), leading to compound (II'''a) comprising a reactive function, enabling the coupling with a vector (i.e. bioactive group), through the reaction with a reactive function B of said vector:

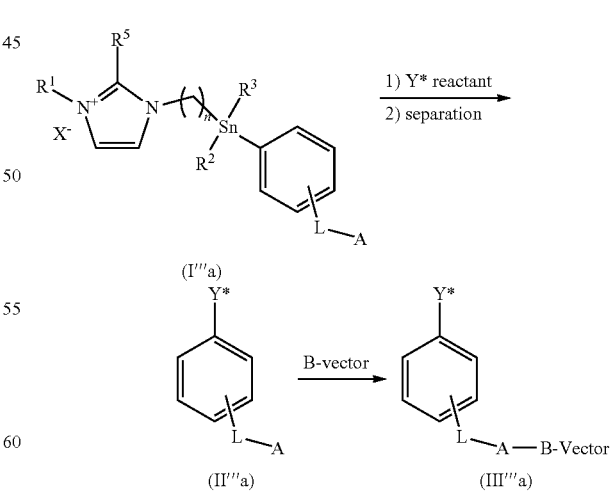

wherein A and B represent reactive functions
According to one embodiment, in radiopharmaceutical (III'''a), -A-B— represents the residue of coupling between reactive function A and reactive function B.

In one embodiment, the present invention relates to the radiolabelling of a compound of formula (I) to form a compound of formula (II) bearing one reactive function and coupling the resulting compound to a vector to form a radiopharmaceutical (III).

In another embodiment, the present invention relates to the radiolabelling of a compound of formula (I) to form a compound of formula (II) bearing one protected reactive function and, after deprotection of said reactive function, coupling the resulting compound to a vector to form a radiopharmaceutical (III).

In another embodiment, the present invention relates to the radiolabelling of a compound of formula (I) to form a compound of formula (II) bearing one reactive function and, after activation of said reactive function, coupling the resulting compound to a vector to form a radiopharmaceutical (III).

Coupling of compound (II) to the vector may be performed methods well known by one skilled in the art, and are for example described in: Wong et al., CRC press 2011 (NY), 604; Benoiton et al. WORKBENCH EDITION; Basle et al., Chemistry & Biology (2010), Volume 17, Issue 3, 213-227; Sletten et al., Angew. Chem. Int. Ed. (2009), 48, 6974-6998; Liu et al. Advanced Drug Delivery Reviews (2008), 60 (12), 1347-1370; Wu et al. Nat Biotechnol 2005, 23:1137-1146; Fritzberg et al., Pharmaceutical Research (1988), 5 (6), 325-334.

Automated Device

The present invention further relates to a device for implementing the labeling process of the invention comprising at least one automaton of synthesis comprising at least:
  controlling means;
  a vacuum system;
  one reaction vessel;
  a purification cartridge;
  at least one line connected at one end to the reaction vessel and at the other end to a storage vessel, said storage vessel comprising ionic liquid organotin reagent (I) of the invention;
  at least one line connected at one end to the reaction vessel and at the other end to a storage vessel, said storage vessel containing an electrophilic reactant comprising halogen Y*, or directly connected at the other end to an arrival of an electrophilic reactant comprising halogen Y* or a precursor thereof (distillation apparatus or production line);
  optionally at least one line connected at one end to the reaction vessel and at the other end to a storage vessel, said storage vessel comprising an oxidizing agent;
  at least one line connected at one end to the reaction vessel and at the other end to the top of the purification cartridge;
  at least one output line connected at one end to the bottom end of the purification cartridge, the other end enabling to recover compound (II) of the invention;
  optionally a line connected to an inert gas arrival.

According to one embodiment, the device for implementing the labeling process of the invention further optionally comprises a heater and/or an inert gas arrival.

In one embodiment, the device for implementing the labeling process of the invention further optionally comprises a second automaton including at least:
  controlling means;
  a vacuum system;
  one reaction vessel;
  a purification cartridge;
  at least one input line connected at one end to the output line of the first automaton and at the other end to the reaction vessel to introduce compound (II) of the invention in the second automaton;
  at least one line connected at one end to the reaction vessel and at the other end to a storage vessel, said storage vessel comprising the vector;
  at least one line connected at one end to the reaction vessel and at the other end to a storage vessel, said storage vessel comprising an aqueous solvent;
  at least one line connected at one end to the reaction vessel and at the other end to the top of the purification cartridge;
  at least one line connected at one end to the bottom end of the purification cartridge, the other end enabling to recover compound (III) of the invention;
  optionally a line connected to an inert gas arrival.

According to one embodiment, the second automaton further optionally comprises a heater and/or an inert gas arrival.

A device comprising two automatons according to the invention is represented in The FIGURE.

In an embodiment, lines and connections are compatible with the use of organic solvent, preferably ethyl acetate, heptane, hexane, cyclohexane, acetone, methanol, acetonitrile, diisopropyl ether, dichloromethane, chloroform, acetic acid, or a mixture thereof.

Kit of Parts

The present invention further relates to a kit comprising an ionic liquid supported organotin reagent (I) of the invention.

According to one embodiment, the kit of the invention comprises an ionic liquid supported organotin reagent (I) of the invention and an oxidizing agent. In one embodiment, the oxidizing agent is selected from the group comprising N-chlorosucciminide (NCS), N-iodosuccinimide, N-Bromosuccinimide, Chloramine-T, hydrogen peroxide, sodium hypochlorite, terbutylhydroperoxyde, potassium dichromate more preferably N-chlorosuccinimide.

According to one embodiment, the kit of the invention comprises an ionic liquid supported organotin reagent (I) of the invention and an oxidizing agent. In one embodiment, the oxidizing agent is selected from the group comprising N-chlorosucciminide (NCS), N-iodosuccinimide, N-Bromosuccinimide, Chloramine-T, hydrogen peroxide, sodium hypochlorite, terbutylhydroperoxyde, more preferably N-chlorosuccinimide.

According to one embodiment, the kit of the invention further comprises a selectfluor, acetate or triflate salt, more preferably selectfluor salt.

According to one embodiment, the kit of the invention further comprises a metallic catalyst.

According to one embodiment, the kit of the invention further comprises a selectfluor, acetate or triflate salt and a metallic catalyst.

According to one embodiment, the kit of the invention further comprises a reducing agent. In one embodiment, the reducing agent is selected from sodium sulfite, sodium metabisulfite, cysteine and dithiothreitol.

BRIEF DESCRIPTION OF THE DRAWINGS

The FIGURE is a scheme representing a synthesis device comprising two automatons to implement the labeling process of the invention.

EXAMPLES

The present invention is further illustrated by the following examples.

Material

Commercially available reagents and solvents were purified and dried, when necessary, by standard methods prior to use. 1H (300 MHz), 13C (75 MHz) NMR spectra were recorded on a Bruker Avance 300 spectrometer or on a Bruker Avance 400 spectrometer. The compounds studied were measured in CDCl3 and 1H and 13C chemical shifts, reported in ppm, were referred to the central signal of the solvent. 13C NMR spectra were recorded with complete proton decoupling. The 119Sn NMR spectra were recorded on a Bruker Avance 400 spectrometer (149 MHZ) and chemical shifts were referred to external tetramethylstannane. High resolution mass spectra measurements were recorded on Waters-Micromass GCT Premier spectrometers. Analytical thin layer chromatography was performed on pre-coated silica gel 60-F254 plates.

I. Synthesis of Ionic Liquid

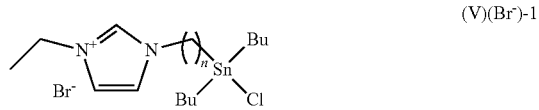

(V)(Br⁻)-1

The synthesis of the ionic liquid (V)(Br⁻)-1 is described in Louaisil et al. Eur. J. Org. Chem. 2011, 143-149.

II. Synthesis of Ionic Liquid Supported Organotin Reagents (I)

General Method

A dried Schlenk tube is flushed with argon and charged with zinc dust (Aldrich Zinc dust <10 μm, 1.36 g, 20.8 mmol, 5 eq) and cobalt(II) bromide (0.095 g, 0.416 mmol, 0.1 eq). The mixture is activated under vacuum at 200° C. during 12 h. Acetonitrile (3 mL) is added to the cooled mixture under argon atmosphere then 1,2-dibromoethane (0.10 mL) is added and the resulting solution is stirred for additional 15 minutes (gas evolution and an increase of temperature are observed). Then arylbromide (6.36 mmol, 6.3 eq) is introduced to the mixture which is stirred at room temperature for 12 h. The resulting solution of arylzinc reagent is introduced dropwise to the ionic liquid (V)(Br⁻)-1 (529 mg, 1.0 mmol, 1 eq) in solution in THF (6 mL). After 18 h of stirring 10 at room temperature, the resulting mixture is filtered through a short pad of silica gel then extracted with CH2Cl2 (3×100 mL). The combined organic layers are dried over MgSO4 and concentrated under reduced pressure. The crude product is purified by silica gel chromatography.

1-(6-(dibutyl(3-(ethoxycarbonyl)phenyl)stannyl)hexyl)-3-ethyl-1H-imidazol-3-ium bromide I-14 (Br⁻)

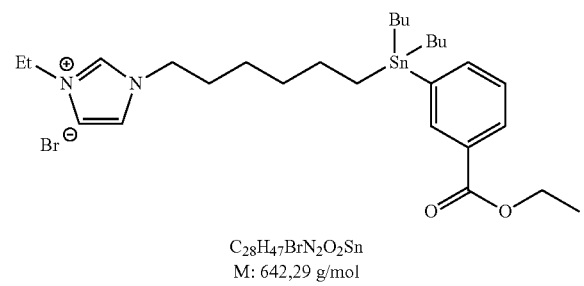

C28H47BrN2O2Sn
M: 642,29 g/mol

Compound I-14(Br⁻) was obtained using general method described above, using ethyl 3-bromobenzoate as arylbromide.

Alternatively, the following conditions were also used. A dried 50 mL Schlenk tube was flushed with argon and charged with zinc dust (1.36 g, 20.8 mmol, 5 eq) and cobalt(II) bromide (0.095 g, 0.419 mmol, 0.1 eq). The mixture was activated under vacuum at 150° C. during 4 h. Acetonitrile (5 mL) was added to the cooled mixture then trifluoroacetic acid (0.15 mL) and 1,2-dibromoethane (0.1 mL) were added and the resulting solution stirred for additional 15 minutes (an increase of temperature was observed). Then ethyl 3-bromobenzoate (1.46 g, 6.36 mmol, 6.3 eq) was introduced to the mixture which was stirred at room temperature for 12 h. The resulting solution of arylzinc reagent was introduced dropwise to the ionic liquid (V)(Br⁻)-1 (529 mg, 1.0 mmol, 1 eq) in solution in THF (6 mL). After 18 h of stirring at room temperature, the resulting mixture was filtered through a short pad of silica gel then extracted with CH2Cl2 (3×100 mL). The combined organic layers were dried over MgSO4 and concentrated under reduced pressure. The crude product was purified by silica gel chromatography (CH2Cl2 to CH2Cl2/MeOH 90:10) to afford compound I-14(Br⁻) as viscous yellow oil (450 mg, 70%).

$^1$H NMR (CDCl3): δ 10.17 (s, 1H), 8.14 (bs, 1H), 7.92 (d, J=7.8 Hz, 1H), 7.62 (d, J=7.2 Hz, 1H), 7.39 (dd, J=7.5 Hz, J=7.5 Hz, 1H), 7.30 (bs, 1H), 7.23 (bs, 1H), 4.48-4.33 (m, 4H), 4.32 (t, 2H, J=7.2 Hz), 1.89-1.78 (m, 2H), 1.61-1.47 (m, 9H), 1.42-1.24 (m, 11H), 1.13-1.00 (m, 6H), 0.87 (t, J=7.2 Hz, 6H). $^{13}$C NMR 75 MHz (CDCl3) δ (ppm): 166.8, 141.9, 140.6, 136.9, 135.9, 129.4, 128.8, 127.5, 122.0, 121.8, 60.6, 49.8, 45.1, 33.4, 30.0, 28.7, 27.0, 26.3, 25.5, 15.5, 14.4, 13.4, 9.4, 9.3. HRMS (FAB) calcd. for C28H47N2O2Sn, 563.2654 [M-Br]⁺; found 563.2675.

1-(6-(dibutyl(3-(ethoxycarbonyl)phenyl)stannyl)hexyl)-3-ethyl-1H-imidazol-3-ium tetrafluoroborate I-14(BF4⁻)

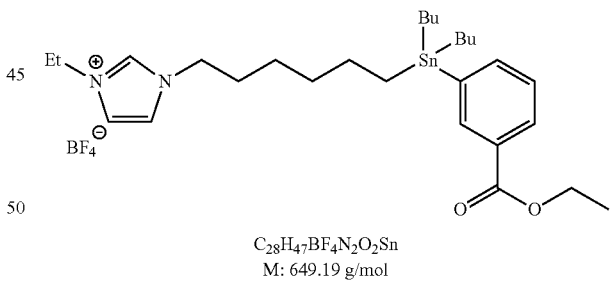

C28H47BF4N2O2Sn
M: 649.19 g/mol

Compound I-14(Br⁻) (50 mg, 0.078 mmol, 1 eq) was dissolved in acetone (4 ml) and stirred with NaBF4 (17 mg, 0.155 mmol, 2 eq) at room temperature for 24 h to exchange the anion. The reaction mixture was filtered off to remove precipitated NaBr and excess of NaBF4 and the acetone was evaporated under reduced pressure. The crude product was purified by silica gel chromatography (CH2Cl2 to CH2Cl2/MeOH 95:05 to 90:10 to) to afford compound I-14(BF4⁻) as viscous yellow oil (42 mg, 83%).

$^1$H NMR (CDCl3): δ 9.26 (s, 1H), 8.14 (bs, 1H), 7.98 (d, J=7.8 Hz, 1H), 7.66 (d, J=7.2 Hz, 1H), 7.42 (dd, J=7.2 Hz, J=7.2 Hz, 1H), 7.35 (bs, 1H), 7.28 (bs, 1H), 4.44-4.30 (m, 4H), 4.21 (t, J=7.4 Hz, 2H), 1.93-1.80 (m, 2H), 1.75-1.65

(m, 2H), 1.63-1.49 (m, 7H), 1.45-1.28 (m, 13H), 1.15-1.03 (m, 4H), 0.91 (t, J=7.2 Hz, 6H). $^{13}$C NMR 75 MHz (CDCl$_3$) δ (ppm): 167.3, 142.3, 141.0, 137.3, 136.3, 129.7, 129.2, 127.8, 121.9, 121.6, 60.9, 50.2, 45.4, 33.6, 30.1, 29.1, 27.4, 26.6, 25.7, 15.3, 14.4, 13.7, 9.6 (2C). HRMS (FAB) calcd. for C$_{28}$H$_{47}$N$_2$O$_2$Sn, 563.2654 [M-BF$_4$]$^+$; found 563.2655.

1-(6-(dibutyl(3-(ethoxycarbonyl)phenyl)stannyl)hexyl)-3-ethyl-1H-imidazol-3-ium hexafluorophosphate I-14(PF$_6^-$)

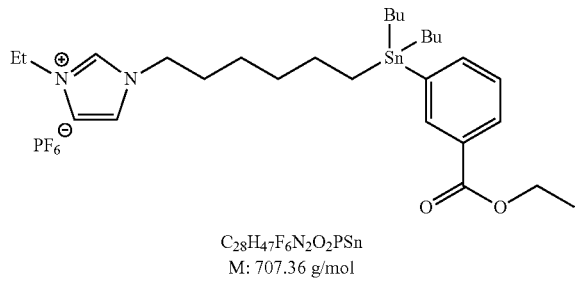

C$_{28}$H$_{47}$F$_6$N$_2$O$_2$PSn
M: 707.36 g/mol

Compound I-14(Br$^-$) (150 mg, 0.233 mmol, 1 eq) was dissolved in acetone (4 ml) and stirred with NaPF$_6$ (78 mg, 0.464 mmol, 2 eq) at room temperature for 24 h to exchange the anion. The reaction mixture was filtered and the acetone was evaporated under reduced pressure. The crude product was purified by silica gel chromatography (CH$_2$Cl$_2$ to CH$_2$Cl$_2$/MeOH 90:10) to afford compound I-14(PF$_6^-$) as viscous yellow oil (156 mg, 94%).

$^1$H NMR (CDCl$_3$): δ 9.51 (bs, 1H), 8.15 (s, 1H), 7.98 (d, J=7.8 Hz, 1H), 7.68 (d, J=7.2 Hz, 1H), 7.42 (dd, J=7.2 Hz, J=7.2 Hz, 1H), 7.26 (bs, 1H), 7.22 (bs, 1H), 4.51-4.31 (m, 6H), 1.95-1.77 (m, 4H), 1.62-1.50 (m, 8H), 1.45-1.28 (m, 12H), 1.14-1.06 (m, 4H), 0.91 (t, J=7.2 Hz, 6H). $^{13}$C NMR 75 MHz (CDCl$_3$) δ (ppm): 167.3, 142.3, 141.0, 137.3, 136.5, 129.7, 129.1, 127.9, 121.8, 121.4, 61.0, 50.4, 45.6, 33.7, 30.2, 29.1, 27.4, 26.6, 25.8, 15.6, 14.4, 13.8, 9.7, 9.6. HRMS (FAB) calcd. for C$_{28}$H$_{47}$N$_2$O$_2$Sn, 563.2654 [M-PF$_6$]$^+$; found 563.2655.

1-(6-(dibutyl(3-carboxyphenyl)stannyl)hexyl)-3-ethyl-1H-imidazol-3-ium bromide I-2(Br$^-$)

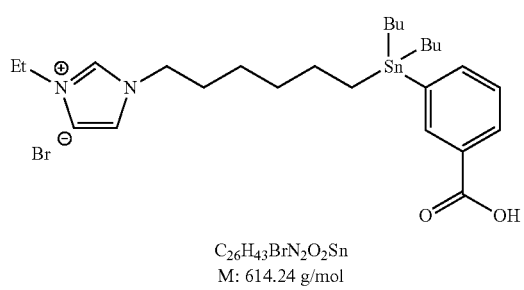

C$_{26}$H$_{43}$BrN$_2$O$_2$Sn
M: 614.24 g/mol

To a solution of 600 mg of compound I-14(Br$^-$) (0.934 mmol, 1 eq) in ethanol (5 mL) were added 0.97 mL of an aqueous solution of NaOH (15% w/w). The resulting mixture was stirred for 20 min at room temperature, then refluxed 2 h and the ethanol was removed under reduced pressure. The residue was acidified with 3 mL of HCl 1M, and then extracted with CH$_2$Cl$_2$ (3×30 mL). The combined organic layers were dried over MgSO$_4$ and concentrated under reduced pressure. The crude product I-2(Br$^-$) was used without purification in the next step (520 mg, 90%).

HRMS (FAB) calcd. for C$_{26}$H$_{43}$N$_2$O$_2$Sn, 535.2341 [M-Br]$^+$; found 535.2336.

1-(6-(dibutyl(3-a(2,5-dioxopyrrolidin-1-yl)oxy)carbonyl)phenyl)stannyl)hexyl)-3-ethyl-1H-imidazol-3-ium bromide I-1(Br$^-$)

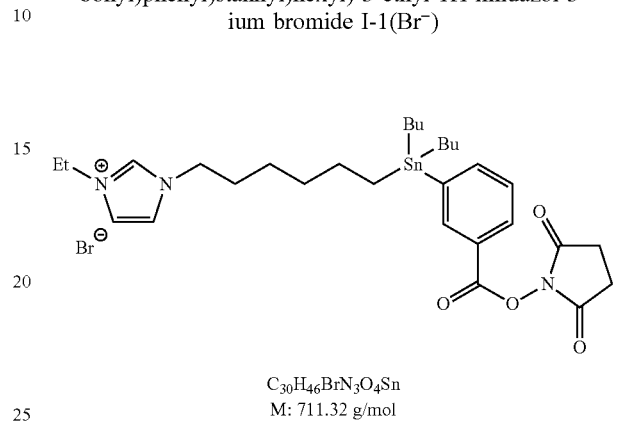

C$_{30}$H$_{46}$BrN$_3$O$_4$Sn
M: 711.32 g/mol

A mixture of compound I-14(Br$^-$) (510 mg, 0.83 mmol, 1 eq), N-hydroxysuccinimide (105 mg, 0.913 mol, 1.1 eq.) and DCC (188 mg, 0.913 mol, 1.1 eq) in dry THF (10 mL) was stirred for 12 h at room temperature under argon. The reaction mixture was filtered and the residue was concentrated under reduced pressure. The corresponding product I-1(Br$^-$) was purified by silica gel chromatography (CH$_2$Cl$_2$ to CH$_2$Cl$_2$/MeOH 98:02 to 90:10) to afford yellow oil (371 mg, 63%).

$^1$H NMR (CDCl$_3$): δ 9.83 (s, 1H), 8.20 (bs, 1H), 8.05 (d, J=8.2 Hz, 1H), 7.78 (d, J=7.5 Hz, 1H), 7.49 (t, J=7.5 Hz, J=7.5 Hz, 1H), 7.36 (bs, 1H), 7.22 (bs, 1H), 4.48-4.26 (m, 4H), 2.96 (s, 4H), 1.75-1.62 (m, 2H), 1.58-1.44 (m, 7H), 1.38-1.23 (m, 12H), 1.13-1.04 (m, 4H), 0.93 (t, J=7.2 Hz, 3H), 0.91 (t, J=7.2 Hz, 3H). $^{13}$C NMR 75 MHz (CDCl$_3$) δ (ppm): 169.7, 162.5, 143.5, 143.1, 138.0, 136.6, 130.1, 128.3, 124.4, 122.2, 121.8, 50.1, 45.4, 33.6, 29.0, 28.2, 27.3, 26.9, 25.9, 20.4, 15.7, 13.8, 13.7, 9.7, 9.6. HRMS (FAB) calcd. for C$_{30}$H$_{46}$N$_3$O$_4$Sn, 632.2505 [M-Br]$^+$; found 632.2522.

1-(6-(dibutyl(3-(((2,5-dioxopyrrolidin-1-yl)oxy)carbonyl)phenyl)stannyl)hexyl)-3-ethyl-1H-imidazol-3-ium hexafluorophosphate I-1(PF$_6^-$)

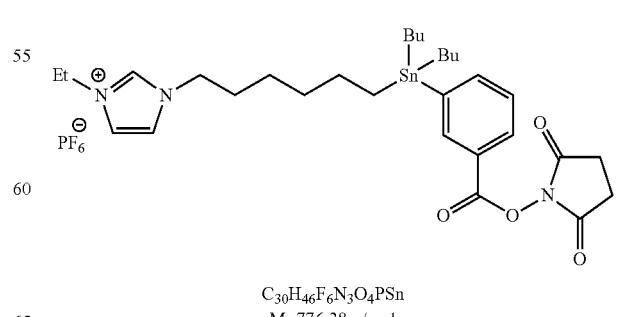

C$_{30}$H$_{46}$F$_6$N$_3$O$_4$PSn
M: 776.38 g/mol

Compound I-1(Br⁻) (110 mg, 0.154 mmol, 1 eq) was dissolved in acetone (4 ml) and stirred with NaPF₆ (52 mg, 0.308 mmol, 2 eq) at room temperature for 24 h to exchange the anion. The reaction mixture was filtered and the acetone was evaporated under reduced pressure. The crude product was purified by silica gel chromatography (CH₂Cl₂ to CH₂Cl₂/MeOH 90:10) to afford compound I-1(PF₆) as viscous yellow oil (81 mg, 67%).

$^1$H NMR (CDCl₃): δ 8.59 (bs, 1H), 8.18 (bs, 1H), 8.03 (dm, J=7.8 Hz, 1H), 7.77 (dm, J=7.2 Hz, 1H), 7.47 (dd, J=7.2 Hz, J=7.2 Hz, 1H), 7.27 (bs, 1H), 7.17 (bs, 1H), 4.26 (q, J=7.5 Hz, 2H), 4.11 (t, J=7.5 Hz, 2H), 2.97 (s, 4H), 1.82-1.46 (m, 10H), 1.43-1.28 (m, 11H), 1.17-1.07 (m, 4H), 0.91 (t, J=7.5 Hz, 6H). HRMS (FAB) calcd. for C₃₀H₄₆N₃O₄Sn, 632.2505 [M-PF₆]⁺; found 632.2484.

1-(6-((4-(aminomethyl)phenyl)dibutylstannyl)hexyl)-3-ethyl-1H-imidazol-3-ium bromide I-4(Br⁻)

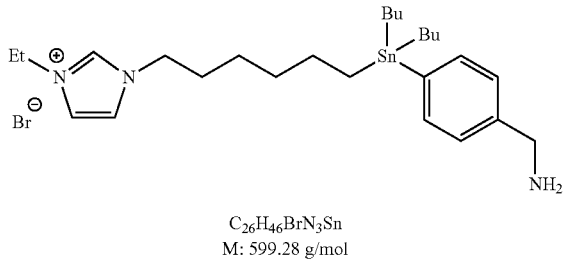

C₂₆H₄₆BrN₃Sn
M: 599.28 g/mol

Compound I-4(Br⁻) was obtained using general method described above, using 4-bromophenyl)methanamine as arylbromide.

Alternatively, compound I-4(Br⁻) was obtained according to the procedure of the synthesis of compound I-14(Br⁻) and starting from (4-bromophenyl)methanamine (513 mg, 2.76 mmol, 4.9 eq) and ionic liquid (V)(Br⁻)-1 (300 mg, 0.568 mmol, 1 eq) in dry THF (4 mL). The crude product was filtered and solvent was removed under reduced pressure. The residue was extracted with Et₂O to remove the excess then CH₂Cl₂ to afford crude compound I-4(Br⁻) as viscous yellow oil (490 mg).

$^1$H NMR (CDCl₃): δ 9.89 (s, 1H), 8.26-8.04 (m, 2H), 7.63-7.56 (m, 2H), 7.44-7.30 (m, 2H), 7.2 (bs, 1H), 7.19 (bs, 1H), 4.41 (q, J=7.5 Hz, 2H), 4.32 (t, J=7.2 Hz, 2H), 4.25-4.12 (m, 2H), 1.92-1.75 (m, 2H), 1.62-1.39 (m, 8H), 1.37-1.20 (m, 10H), 0.88 (t, J=7.2 Hz, 6H), 0.83-0.71 (m, 5H). MALDI calcd. for C₃₂H₅₄N₃Sn, 520.27 [M-Br]⁺; found 520.50.

1-(6-(dibutyl(4-((methylamino)methyl)phenyl)stannyl)hexyl)-3-ethyl-1H-imidazol-3-ium bromide I-15 (Br⁻)

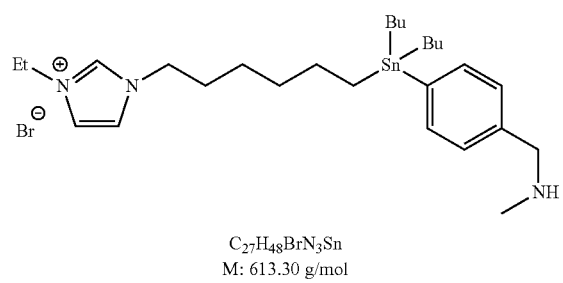

C₂₇H₄₈BrN₃Sn
M: 613.30 g/mol

Compound I-15(Br⁻) was obtained using general method described above, using 1-(4-bromophenyl)-N-methylmethanamine as arylbromide.

Alternatively, compound I-15(Br⁻) was obtained According to the procedure of the synthesis of compound I-14(Br⁻) and starting from 1-(4-bromophenyl)-N-methylmethanamine (350 mg, 1.75 mmol, 3.1 eq) and ionic liquid (V)(Br⁻)-1 (300 mg, 0.568 mmol, 1 eq). in dry THF (4 mL). The crude product was filtered and solvent was removed under reduced pressure. The residue was extracted with Et₂O to remove the excess then CH₂Cl₂ to afford compound I-15 (Br⁻) as viscous yellow oil (350 mg, 92%).

$^1$H NMR (CDCl₃): δ 9.62 (s, 1H), 7.48-7.42 (m, 2H), 7.39-7.33 (m, 2H), 7.24-7.20 (m, 2H), 4.42 (q, J=7.2 Hz, 2H), 4.21 (t, J=7.2 Hz, 2H), 4.05-3.87 (m, 2H), 2.52 (s, 3H), 1.83-1.70 (m, 2H), 1.61-1.47 (m, 8H), 1.38-1.22 (m, 10H), 1.07-0.96 (m, 5H), 0.87 (t, J=7.2 Hz, 6H). $^{13}$C NMR 75 MHz (CDCl₃) δ (ppm): 136.7, 136.4, 131.6, 130.2, 128.9, 121.8, 121.5, 54.7, 50.2, 45.5, 34.7, 33.1, 30.1, 29.0, 27.3, 26.4, 25.7, 15.5, 13.7, 9.6, 9.5. HRMS (FAB) calcd. for C₂₇H₄₈N₃Sn, 534.2865 [M-Br]⁺; found 534.2846.

1-(6-(dibutyl(4-((methylamino)methyl)phenyl)stannyl)hexyl)-3-ethyl-1H-imidazol-3-ium hexafluorophosphate I-15(PF₆⁻)

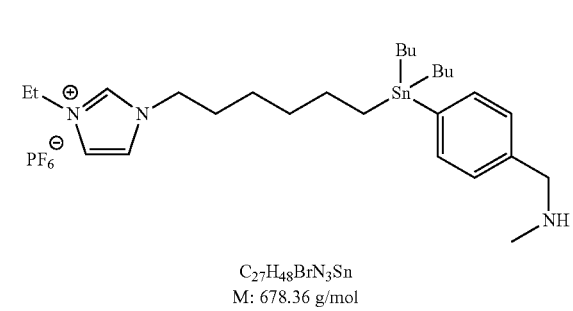

C₂₇H₄₈BrN₃Sn
M: 678.36 g/mol

Compound I-15(Br⁻) (320 mg, 0.522 mmol, 1 eq) was dissolved in acetone (5 ml) and stirred with NaPF₆ (175 mg, 1.04 mmol, 2 eq) at room temperature for 24 h to exchange the anion. The reaction mixture was filtered; the acetone was evaporated under reduced pressure. The residue was extracted with CH₂Cl₂ to afford crude compound I-15(PF₆⁻) as viscous yellow oil (325 mg).

HRMS (FAB) calcd. for C₂₇H₄₈N₃Sn, 534.2865 [M-PF₆]⁺; found 534.2874.

III. Halodemetallation Reaction

125-Iodide

Synthesis of ethyl 3-[I-125]iodobenzoate[$^{125}$I]-II-2

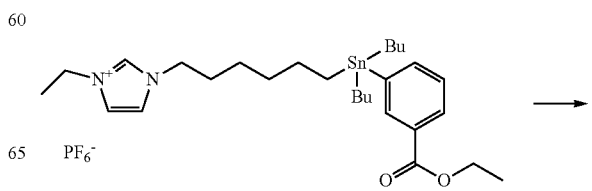

-continued

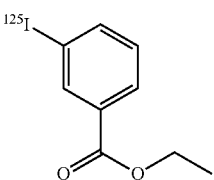

To NaI (1 μl, 26 nmol. including 1.2 pmol (100 kBq) of [I-125]NaI) in NaOH 0.048 M was added NCS (8.7 μl, 130 nmol.) in MeOH/AcOH (95/5). The solution was stirred 30 s at 21° C. I-14(PF$_6^-$) (20 μl, 130 nmol) in MeOH/AcOH (95/5) was then added. After 5 minutes stirring, the radioiodinated ethyl iodobenzoate[$^{125}$I]-II-2 was obtained (93% radiochemical yield (RCY)). The solution was evaporated to dryness and the crude product was recovered in 400 μl of Diethyl ether. After filtration using a silica gel cartridge and Diethyl ether as eluant, the product [$^{125}$I]-II-2 was obtained with a good radiochemical purity.

Synthesis of succinimidyl 3-[I-125]iodobenzoate[$^{125}$I]-II-1

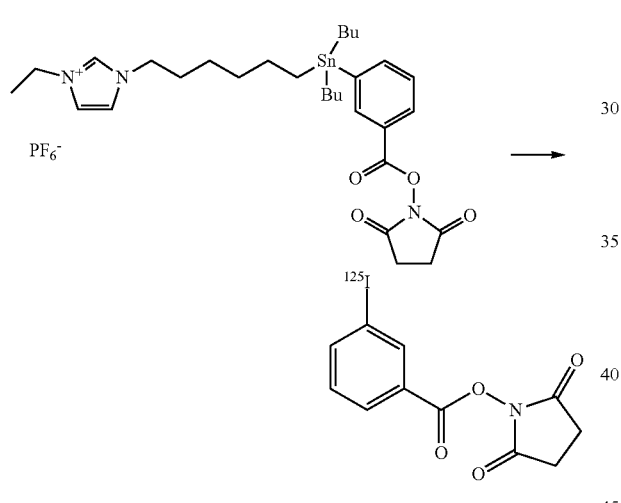

To NaI (1 μl, 46.2 pmol (3.5 MBq) of [I-125]NaI) in NaOH 0.048 M was added NCS (8 μl, 130 nmol.) in MeOH/AcOH (95/5). The solution was stirred 30 s at 21° C. I-1(PF$_6^-$) (20 μl, 26 nmol) in MeOH/AcOH (95/5) was then added. After 30 minutes stirring, the radioiodinated succinimidyl iodobenzoate was obtained (67% radiochemical yield (RCY)). The solution was evaporated to dryness and the crude product was recovered in 400 μl of Diethyl ether. After filtration using a silica gel cartridge and Diethyl ether as eluant, the product was obtained with a good radiochemical purity. Volatiles were evaporated under argon and the purified [$^{125}$I]-II-1 (commonly named SIB) was obtained as a dry residue ready for the coupling to the vector.

Synthesis of Di-HSGL-BSA-SIB

Bovine serum albumin (40 μl,) modified with about 50 Di-HSGL residues per BSA (1.5 mg/ml of BSA in Borate buffer pH 8.6 300 mM) was added to the dry SIB previously obtained ([$^{125}$I]-II-1). The solution was stirred 30 min at 21° C. The radiolabelled BSA was obtained in 54% yield. The radiolabelled BSA was purified on NAP-5 cartridge in a very good radiochemical purity (>90%). and the immunoreactivity of the Di-HSGL residues for IgG 679 was controlled (80%).

211-Astatine

Synthesis of ethyl 3-[At-211]astatobenzoate[$^{211}$At]-II-2

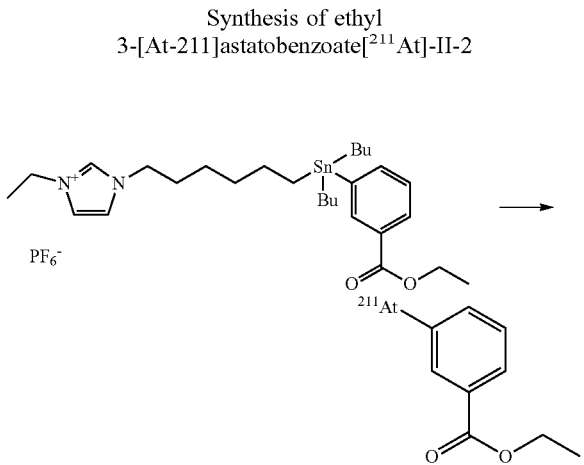

To astatine (50 μl, 1.5 MBq) in methanol was added NCS (2 μl, 30 nmol.) in MeOH/AcOH (95/5). The solution was stirred 30 s at 21° C. I-14(PF$_6^-$) (20 μl, 130 nmol) in MeOH/AcOH (95/5) was added. After 30 minutes stirring, 2 μl of an aqueous solution of sodium metabisulfite (20 mg/ml) was added. The ethyl astatobenzoate[211 At]-II-2 was obtained (87% RCY). The solution was evaporated to dryness and the crude product recovered in 400 μl of diethyl ether. After filtration using a silica gel cartridge and diethyl ether as eluant, the product [$^{211}$At]-II-2 was obtained with a good radiochemical purity.

Synthesis of succinimidyl 3-[At-211]astatobenzoate[$^{211}$At]-II-1

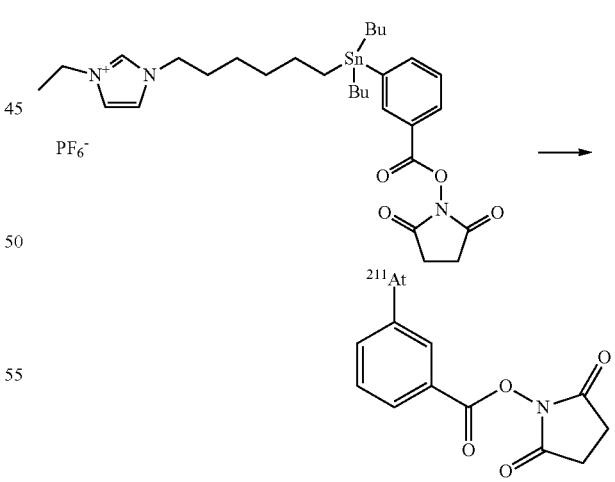

To astatine (50 μl, 4.2 MBq) in methanol was added to NCS (2 μl, 6 nmol.) in MeOH/AcOH (95/5). The solution was stirred 30 s at 21° C. I-1(PF$_6^-$) (20 μl, 650 nmol) in MeOH/AcOH (95/5) was then added. After 30 minutes stirring, 2 μl of an aqueous solution of sodium metabisulfite (20 mg/ml) was added. The succinimidyl m-astatobenzoate [$^{211}$At]-II-1 was obtained (78% RCY). The solution was evaporated to dryness and recovered in 400 μl of diethyl ether. After filtration using a silica gel cartridge and as eluant, the product [²¹¹At]-II-1 (commonly named SAB) was obtained with a good radiochemical purity. Volatiles were evaporated under argon and the purified SAB was obtained as a dry residue ready for the coupling to the vector.

Synthesis of 9E7-SAB

The mAb 9E7 (50 μl, 3.35 mg/ml of 9E7 in Borate buffer pH 8.6 300 mM) was added to the dry SAB previously obtained [²¹¹At]-II-1. The solution was stirred 30 min at 21° C. The radiolabelled 9E7 was obtained in 76% yield. The radiolabelled 9E7 was purified on NAP-5 cartridge and was obtained in a very good radiochemical purity (>90%).

The invention claimed is:

1. A compound of formula (I)

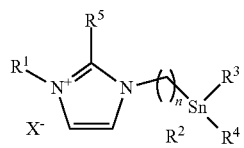

(I)

wherein:

X⁻ represents an anion;

n represents an integer ranging from 3 to 10;

R¹ represents an alkyl group or a PEG chain;

R² and R³ each independently represent an alkyl group;

R⁵ represents H, alkyl or aryl;

R⁴ represents:
  an aryl vector; or
  a group selected from aryl and heteroaryl, substituted by one or more substituents -L-M wherein:

L represents a single bound or a linker selected from aryl, heteroaryl, alkyl, cycloalkyl, alkenyl, cycloalkenyl, alkynyl, cycloalkynyl or a combination thereof;

said groups being optionally substituted by at least one group selected from oxo, thioxo, hydroxyl, ether, carboxylic acid, ester, alkyl, cycloalkyl, alkenyl, cycloalkenyl, heterocyclyl, alkynyl, cycloalkynyl, amine, amide, guanidine, imino, nitro, nitrile, azide, sulfhydryl, sulfide, thioester, thioether, sulfite, sulfate, phosphine, phosphite and phosphate, halogen;

said groups being optionally interrupted or terminated by —O—, —S—, —NR⁶— wherein R⁶ is H or alkyl, or a combination thereof; and optionally L additionally comprises a residue of a reactive group through which L is bounded to M;

M represents:

a reactive function selected from carboxylic acid, nitrile, ester, activated ester, aldehyde, acetal, ketone, ketal, alkyne, azide, alkene, diene, maleimide, protected maleimide, hydroxyl, phenol, 2-aminophenol, thiol, thioester, thioether, thiosulfonate, primary amine, secondary amine, tertiary amine, alkoxyamine, aniline, amide, phosphine, alkyl phosphate, isocyanates, isothiocyanates, hydrazide, hydrazine, tosylate ester, vinyl sulfone, carbamate, carbonate ester, 4-phenyl-1,2,4-triazole-3,5-dione, sulphide, azidoalkyl and azidoaryl; or a bioactive group selected from amino acid, biogenic amine, peptide, heteropeptide, protein, antibody or fragment thereof, monobody, affibody, antibody construct, saccharide, polysaccharide, benzylguanine, biotin, avidin, nucleotide, oligonucleotide, microRNA, hapten, aptamer, ligand, enzyme, enzyme substrate, steroid, hormone, porphyrin, neurotransmitters, sympatomimetic drug, vitamin, phosphonate, nanocarrier, liposome, dendrimer, carbon nanotube and combinations thereof;

said aryl or heteroaryl being optionally further substituted by one or more substituents selected from hydroxyl; linear, cyclic or branched alkyl comprising 1, 2, 3, 4, 5 or 6 carbon atoms; aryl; heteroaryl; heterocyclyl; arylheterocyclyl; alkoxy; halogen; nitro; cyano; azido; aldehyde; boronato; phenyl; CF₃; —CH(OH) (CF₃); —CH(OCH₂OCH₃) (CF₃); methylenedioxy; ethylenedioxy; SO₂NRR', NRR', COOR, CONRR', NRCOR' wherein R and R' are each independently selected from the group consisting of H, alkyl, cycloalkyl, alkenyl, cycloalkenyl, alkynyl, cycloalkynyl and aryl;

wherein the aryl vector is selected from the group consisting of:

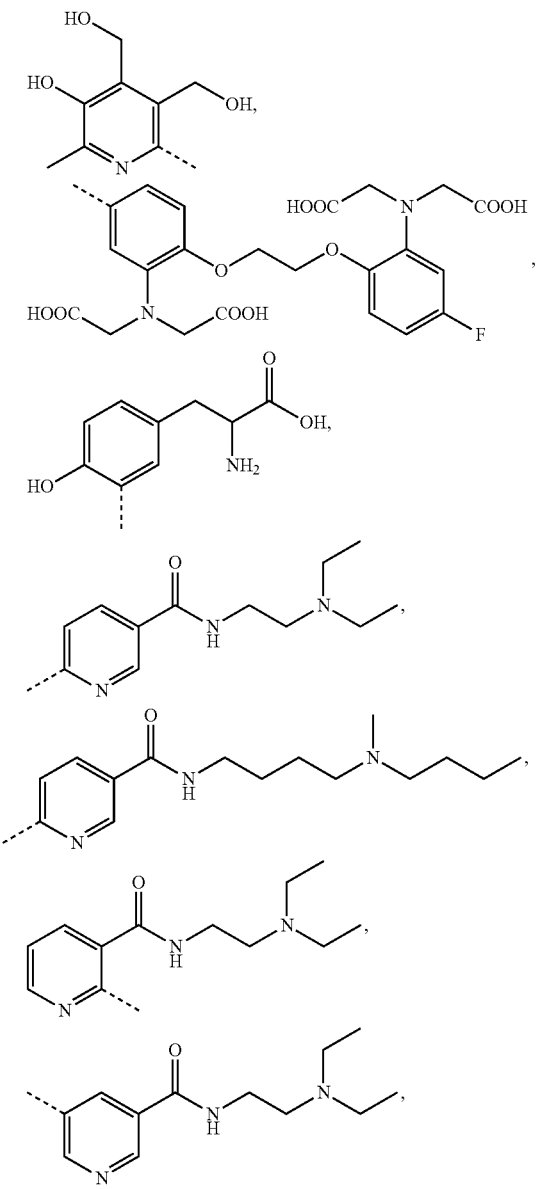

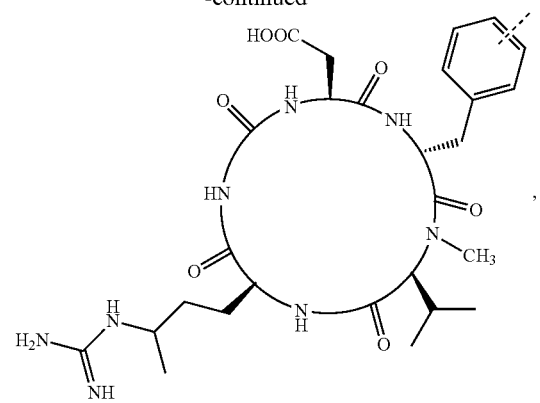
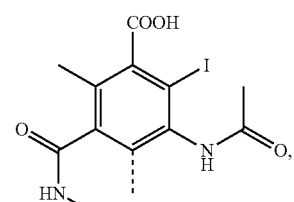
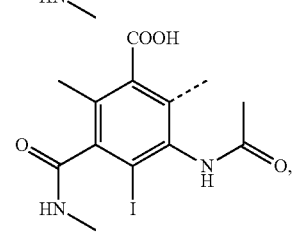
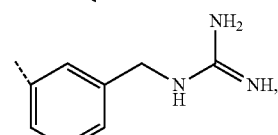
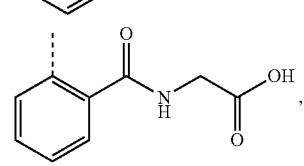
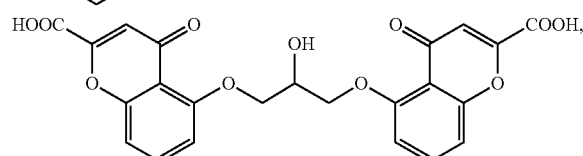
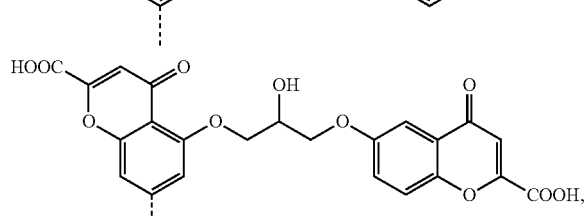
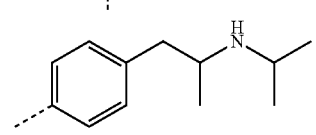
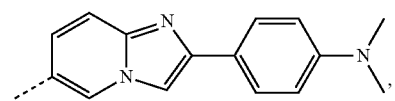
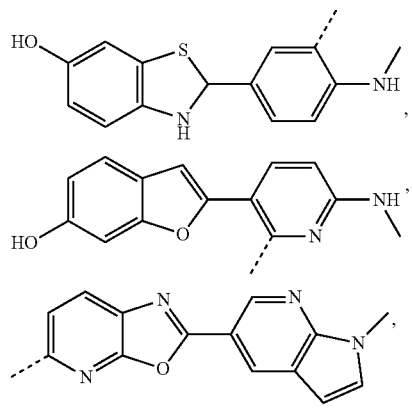

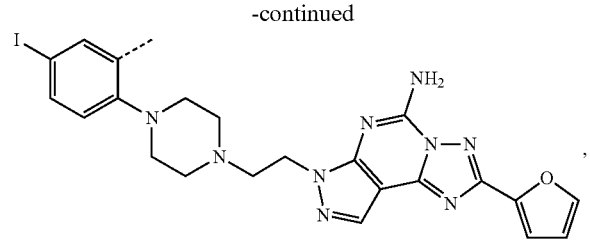
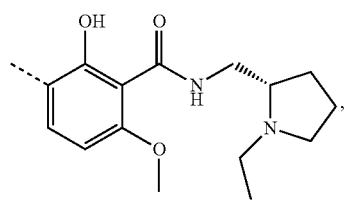
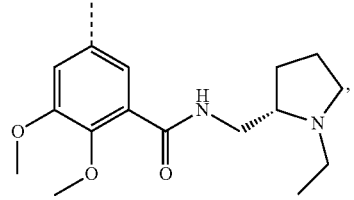
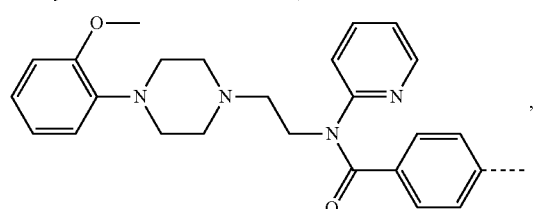
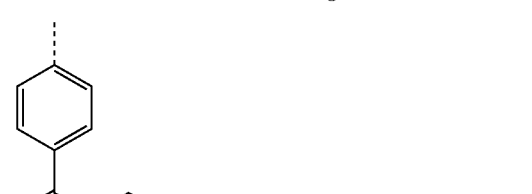
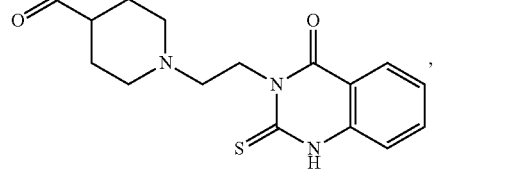
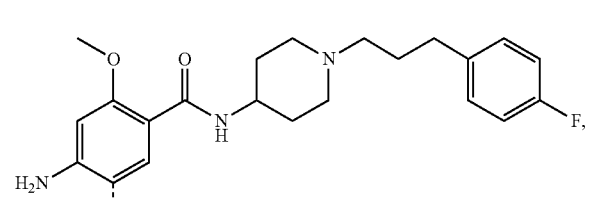
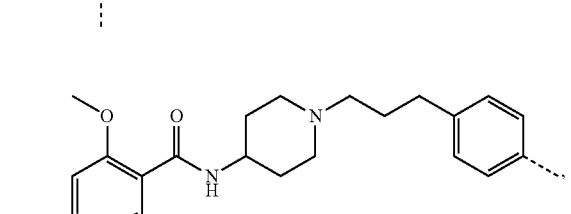
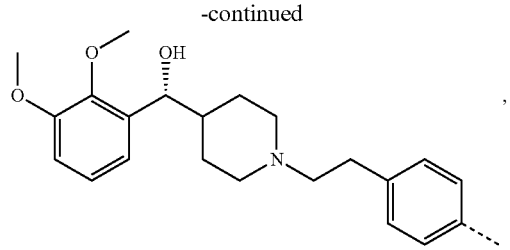
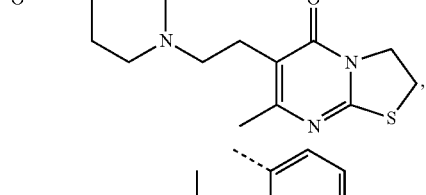
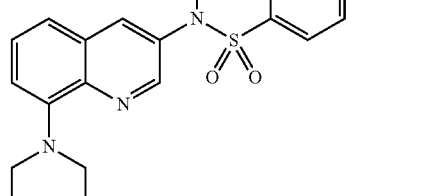
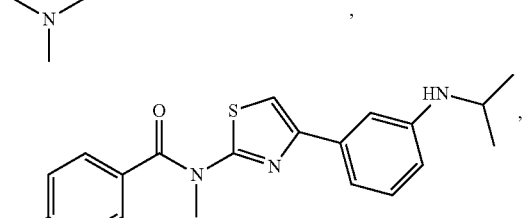
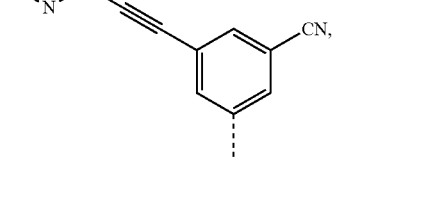
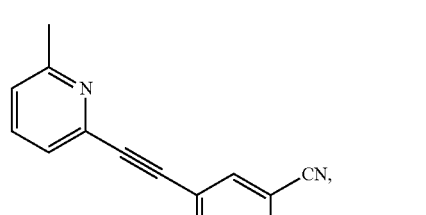
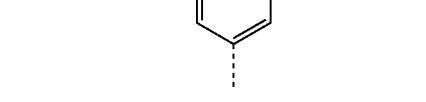

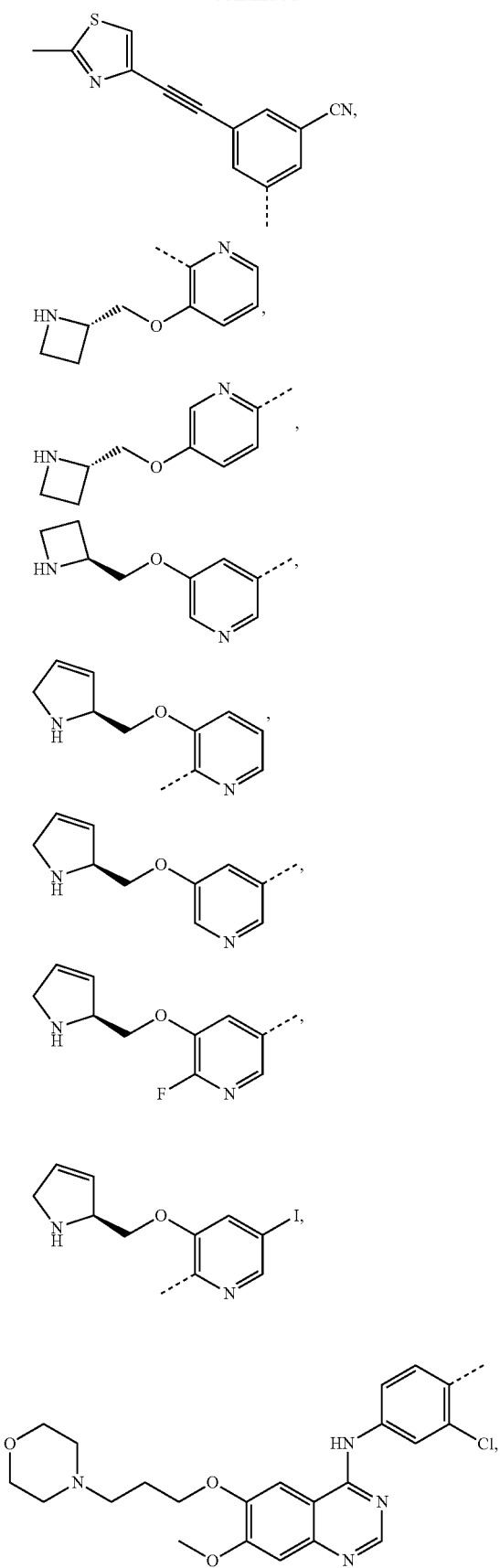
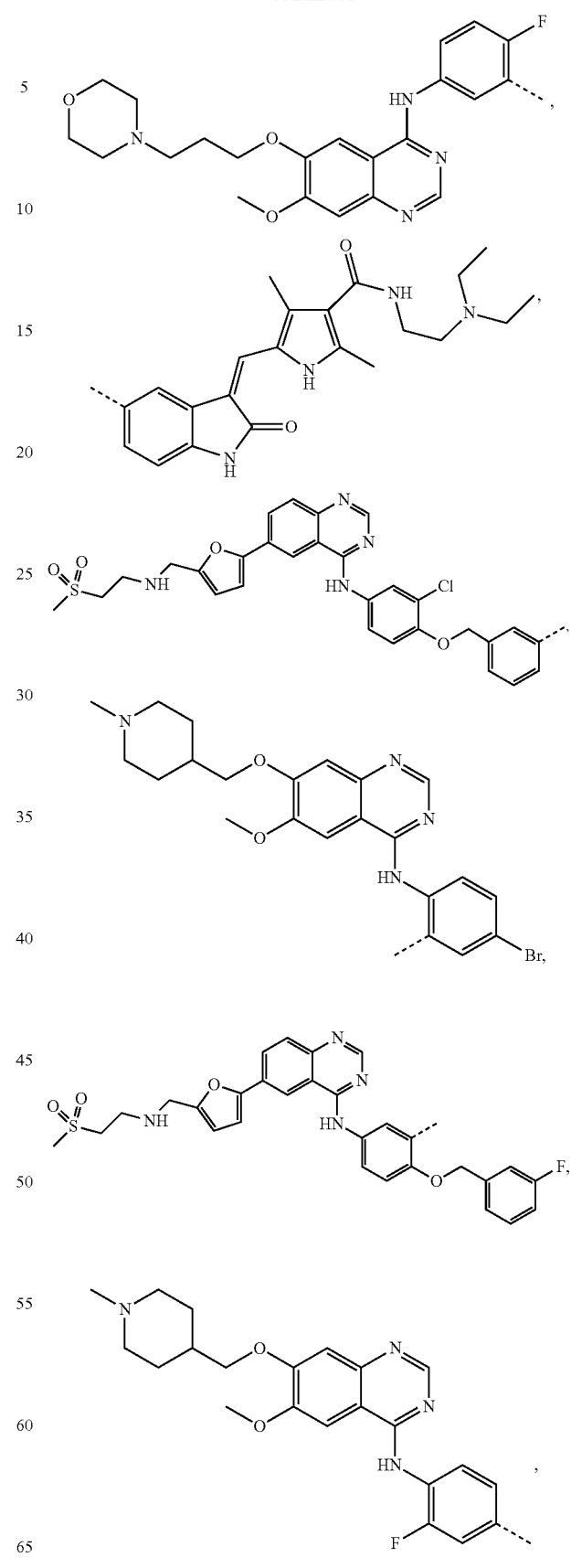

99
-continued
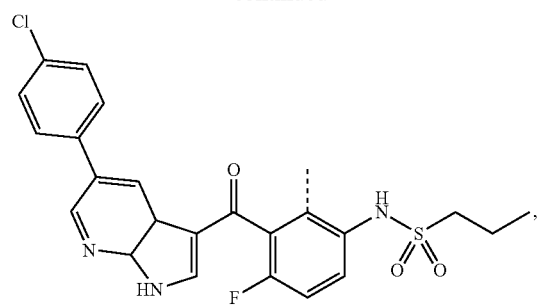
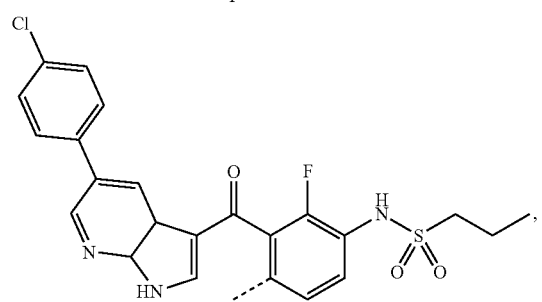
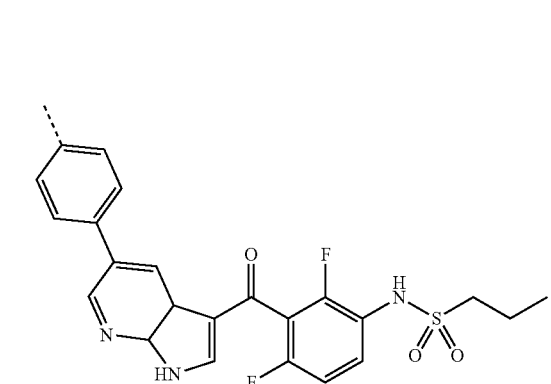
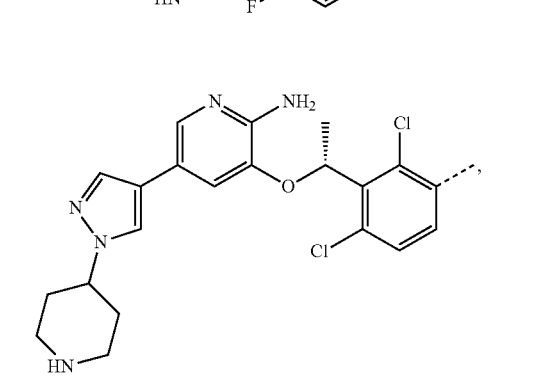
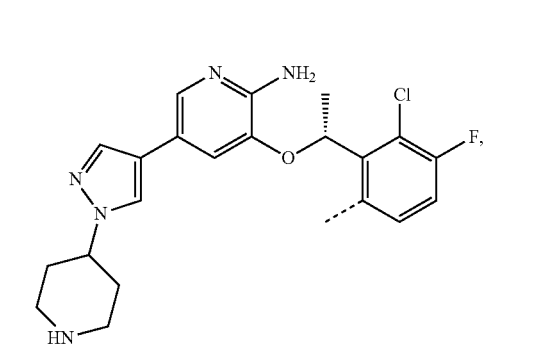
100
-continued
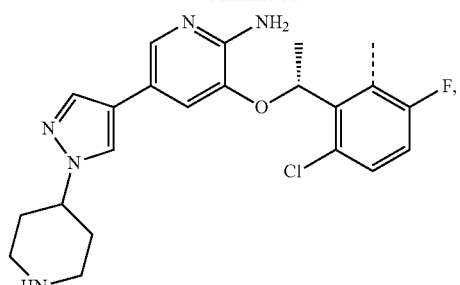
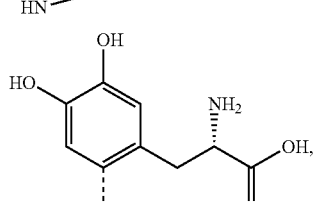
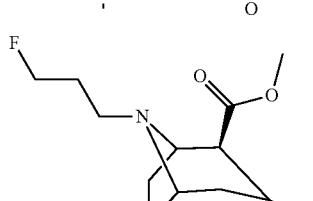
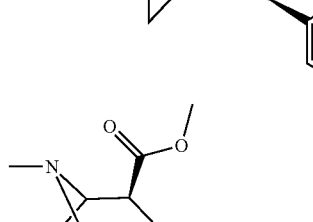
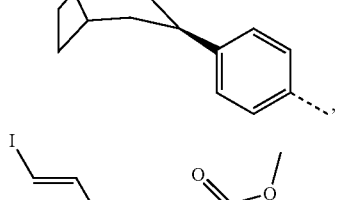
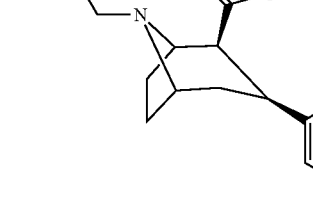
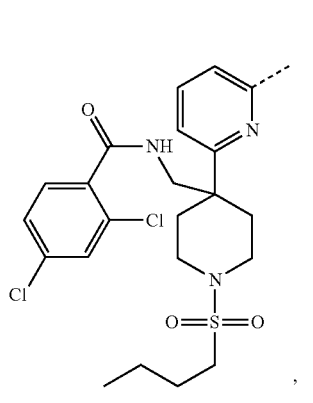

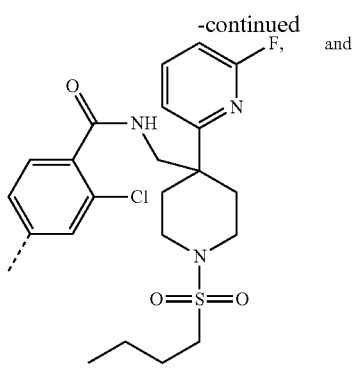

F, and

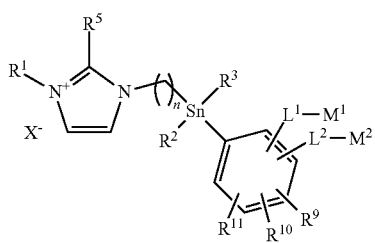

2. The compound according to claim 1, of formula (I')

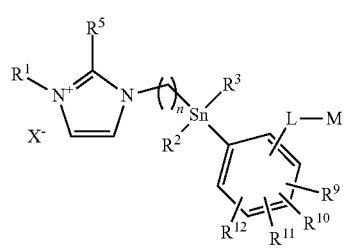

(I')

wherein

X⁻, n, $R^1$, $R^2$, $R^3$ and $R^5$ are as previously defined,

-$L^1$-$M^1$ and -$L^2$-$M^2$ represent each independently -L-M, wherein -L-M is previously defined; and $R^9$, $R^{10}$ and $R^{11}$ represent each independently a group selected from hydroxyl; linear, cyclic or branched alkyl comprising 1, 2, 3, 4, 5 or 6 carbon atoms; aryl; heteroaryl; heterocyclyl; arylheterocyclyl; alkoxy; halogen; nitro; cyano; azido; aldehyde; boronato; phenyl; $CF_3$; —CH(OH) ($CF_3$); —CH($OCH_2OCH_3$) ($CF_3$); methylenedioxy; ethylenedioxy; $SO_2NRR'$, NRR', COOR, CONRR', NRCOR' wherein R and R' are each independently selected from the group consisting of H, alkyl, cycloalkyl, alkenyl, cycloalkenyl, alkynyl, cycloalkynyl and aryl.

3. The compound according to claim 1, of formula (I")

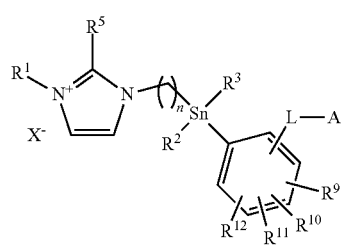

(I")

wherein

X⁻, n, $R^1$, $R^2$, $R^3$, $R^5$ and -L-M are as previously defined; and $R^9$, $R^{10}$, $R^{11}$ and $R^{12}$ represent each independently a group selected from hydroxyl; linear, cyclic or branched alkyl comprising 1, 2, 3, 4, 5 or 6 carbon atoms; aryl; heteroaryl; heterocyclyl; arylheterocyclyl; alkoxy; halogen; nitro; cyano; azido; aldehyde; boronato; phenyl; $CF_3$; —CH(OH) ($CF_3$); —CH($OCH_2OCH_3$) ($CF_3$); methylenedioxy; ethylenedioxy; $SO_2NRR'$, NRR', COOR, CONRR', NRCOR' wherein R and R' are each independently selected from the group consisting of H, alkyl, cycloalkyl, alkenyl, cycloalkenyl, alkynyl, cycloalkynyl and aryl.

4. The compound according to claim 1, of formula (I''')

(I''')

wherein

X⁻, n, $R^1$, $R^2$, $R^3$ $R^5$ and L are as previously defined;

$R^9$, $R^{10}$, $R^{11}$ and $R^{12}$ represent each independently a group selected from hydroxyl; linear, cyclic or branched alkyl comprising 1, 2, 3, 4, 5 or 6 carbon atoms; aryl; heteroaryl; heterocyclyl; arylheterocyclyl; alkoxy; halogen; nitro; cyano; azido; aldehyde; boronato; phenyl; $CF_3$; —CH(OH) ($CF_3$); —CH($OCH_2OCH_3$) ($CF_3$); methylenedioxy; ethylenedioxy; $SO_2NRR'$, NRR', COOR, CONRR', NRCOR' wherein R and R' are each independently selected from the group consisting of H, alkyl, cycloalkyl, alkenyl, cycloalkenyl, alkynyl, cycloalkynyl and aryl; and A represents a reactive function selected from carboxylic acid, nitrile, ester, activated ester, aldehyde, acetal, ketone, ketal, alkyne, azide, alkene, diene, maleimide, protected maleimide, hydroxyl, phenol, 2-aminophenol, thiol, thioester, thioether, thiosulfonate, primary amine, secondary amine, tertiary amine, alkoxyamine, aniline, amide, phosphine, alkyl phosphate, isocyanates, isothiocyanates, hydrazide, hydrazine, tosylate ester, vinyl sulfone, carbamate, carbonate ester, 4-phenyl-1,2,4-triazole-3,5-dione, sulphide, azidoalkyl and azidoaryl.

5. A process for manufacturing a compound of formula (I) according to claim 1, comprising:
1) reacting an activated mixture of zinc and CoBr2 with a compound of formula (IV)

$$R^4—Br \quad (IV)$$

wherein $R^4$ is as previously defined;
in presence of dibromoethane,
to afford the corresponding zinc derivative;
2) reacting the zinc derivative prepared in step 1) with ionic liquid (V) (Br$^-$),

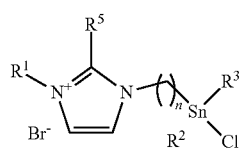

(V)(Br$^-$)

wherein n, $R^1$, $R^2$, $R^3$ and $R^5$ are as previously defined;

to form compound of formula (I) (Br$^-$)

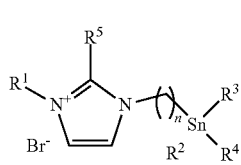

(I)(Br$^-$)

wherein n, $R^1$, $R^3$, $R^4$ and $R^5$ are as previously defined;
3) optionally, a methatesis step to exchange Br$^-$ to another counterion X$^-$ as previously defined, to afford compound of formula (I).

6. A process for the synthesis of a compound of formula (II)

$$R^4—Br^* \quad (IV)$$

wherein
Y* represents a halogen; and
$R^4$ represents:
an aryl vector selected from the group consisting of:

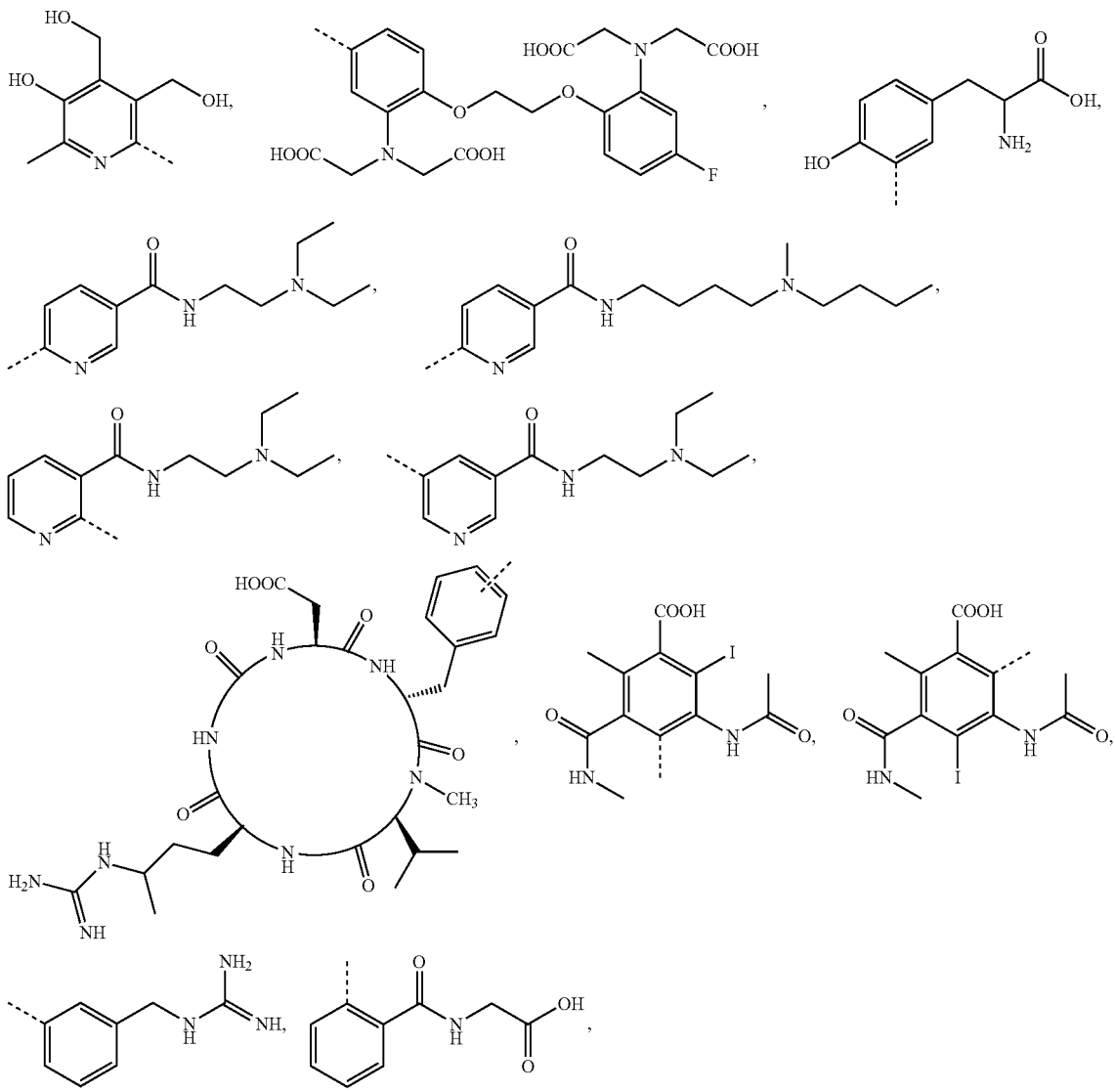

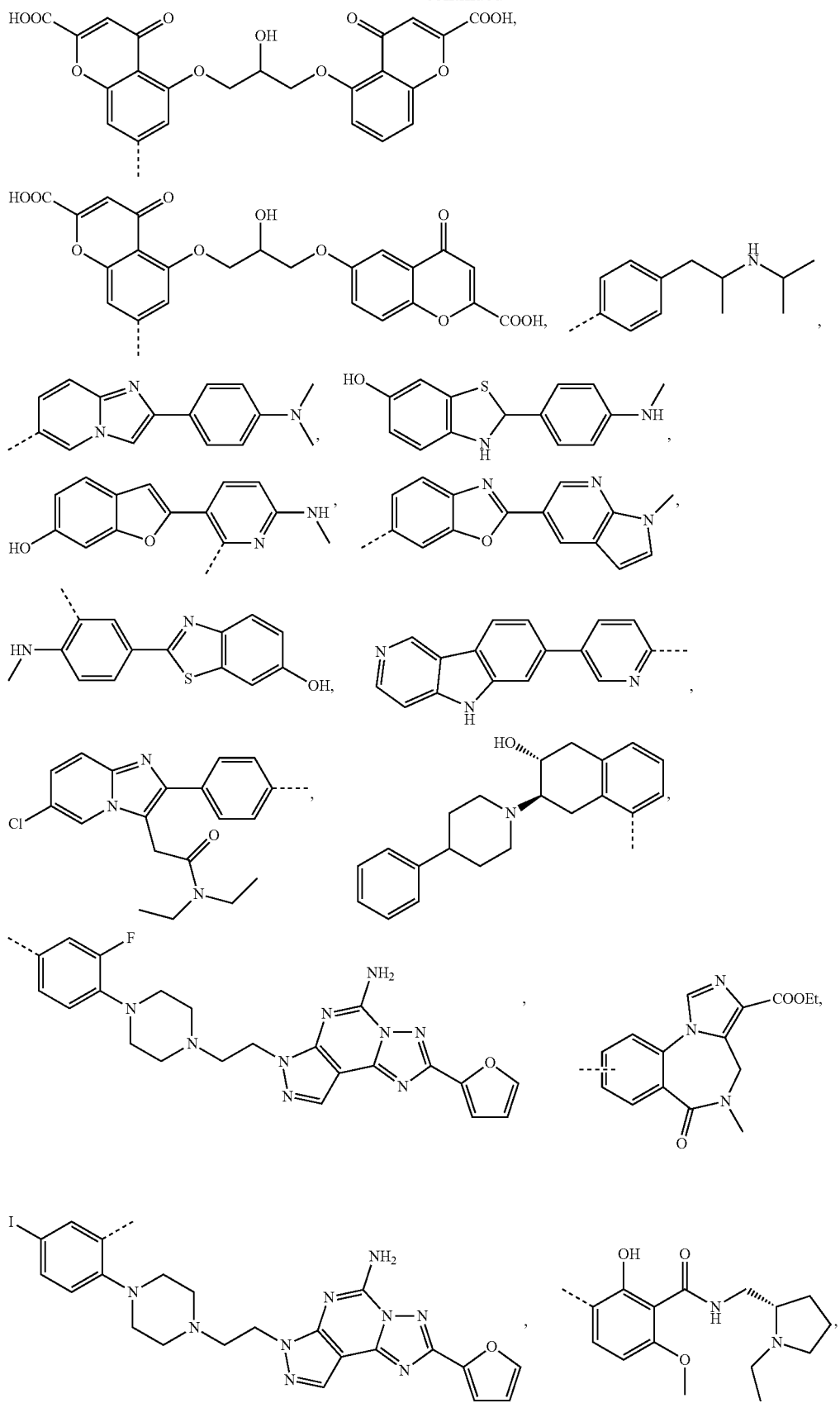

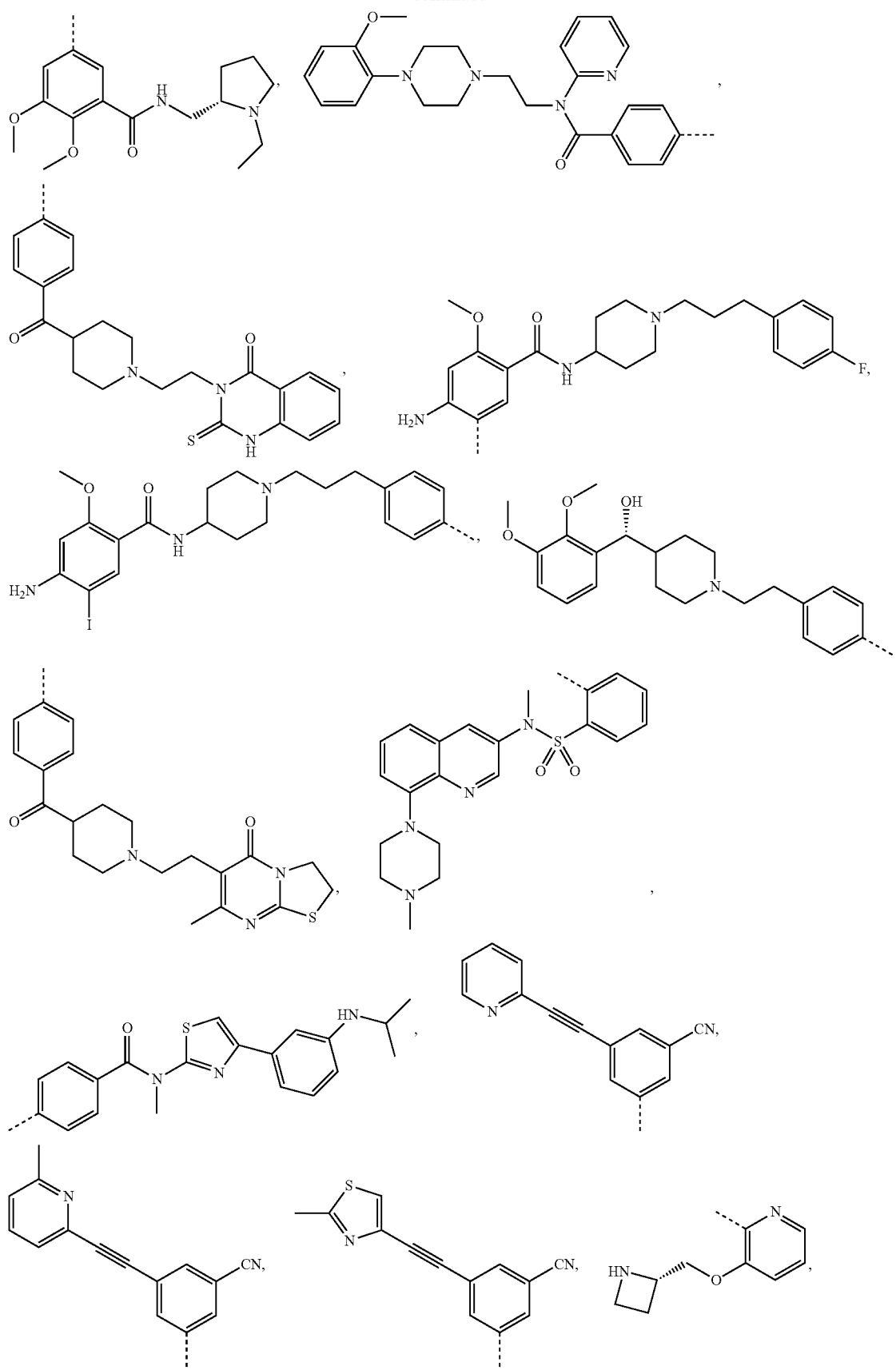

-continued
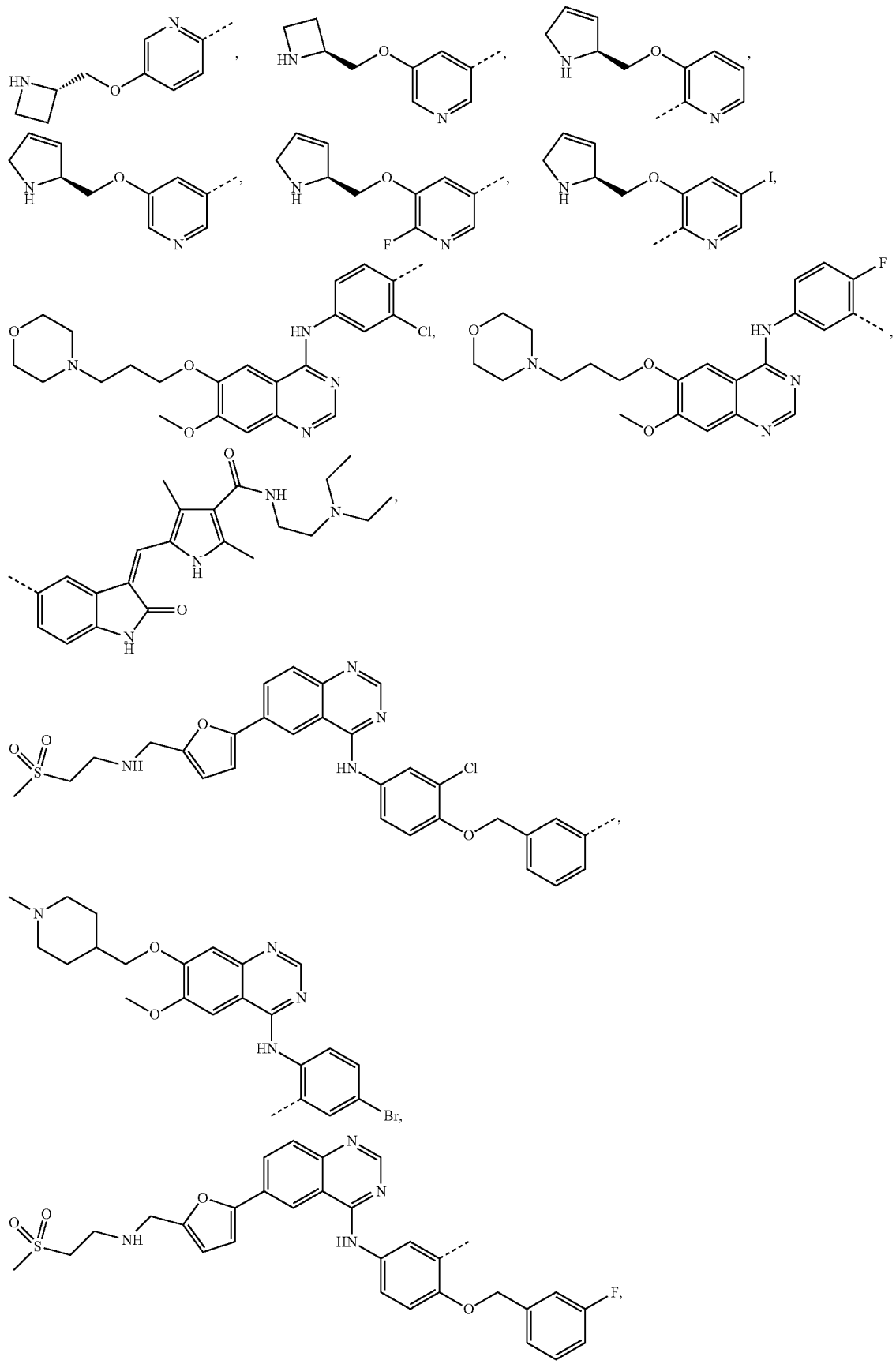

111
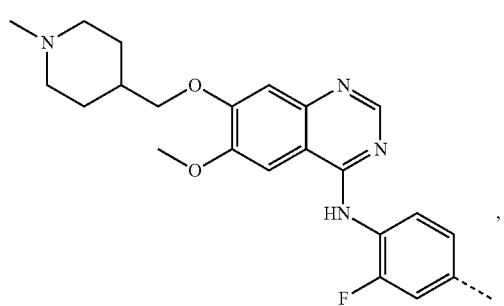
,
112
-continued
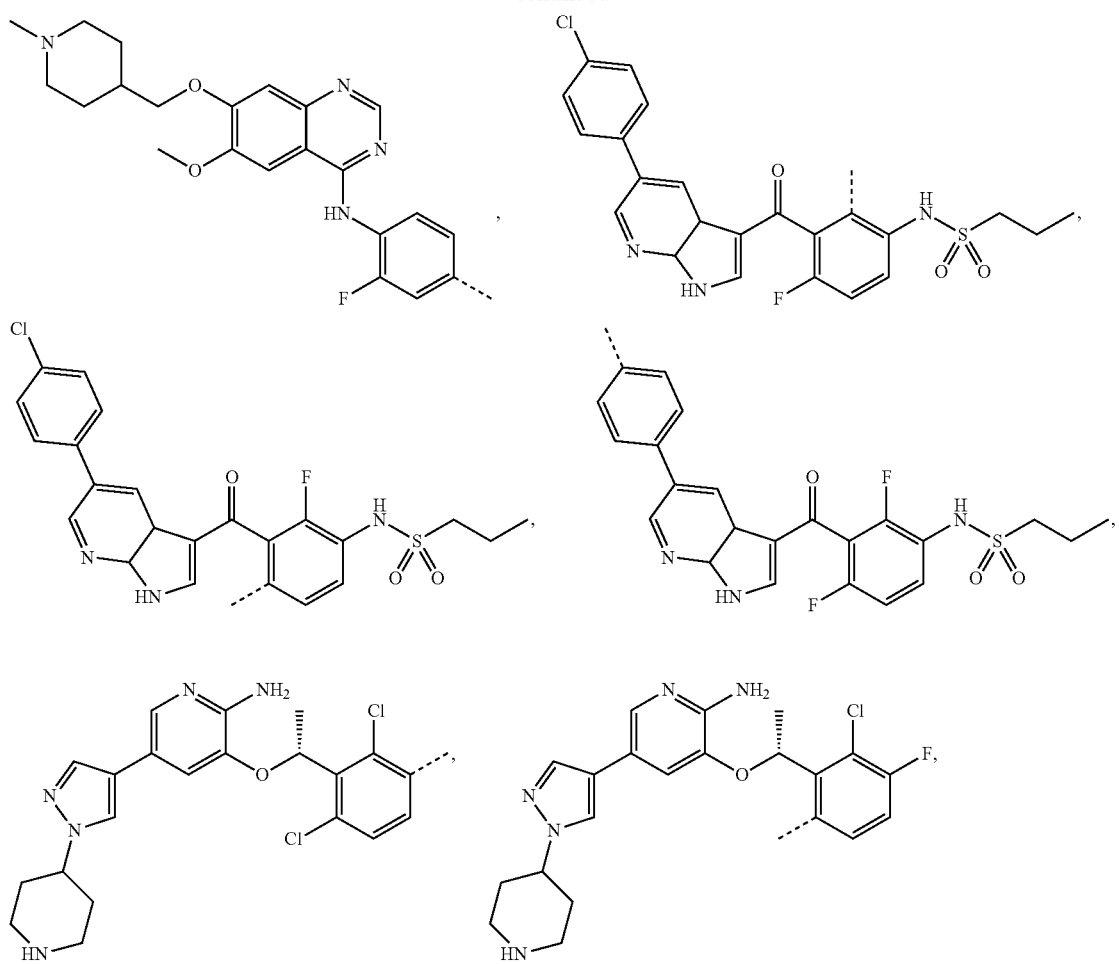

-continued

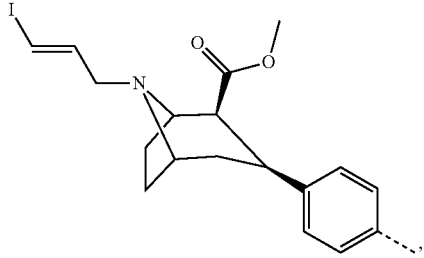 , 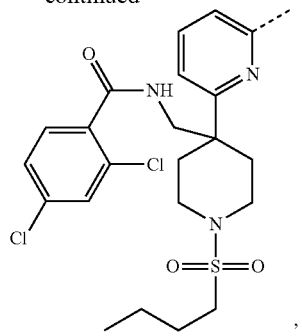 ,

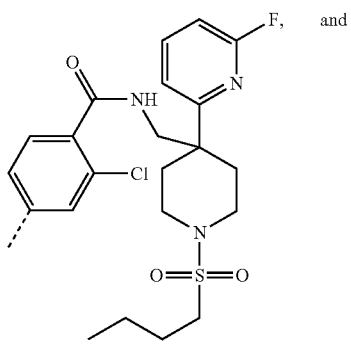 and 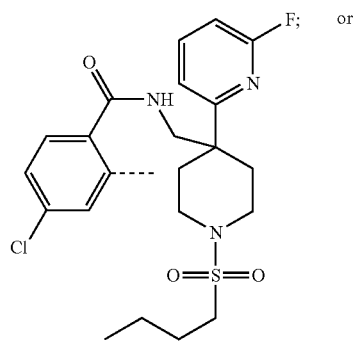 or a group selected from aryl and heteroaryl, substituted by one or more substituents -L-M wherein:
L represents a single bound or a linker selected from aryl, heteroaryl, alkyl, cycloalkyl, alkenyl, cycloalkenyl, alkynyl, cycloalkynyl or a combination thereof;
said groups being optionally substituted by at least one group selected from oxo, thioxo, hydroxyl, ether, carboxylic acid, ester, alkyl, cycloalkyl, alkenyl, cycloalkenyl, heterocyclyl, alkynyl, cycloalkynyl, amine, amide, guanidine, imino, nitro, nitrile, azide, sulfhydryl, sulfide, thioester, thioether, sulfite, sulfate, phosphine, phosphite, phosphate, halogen;
said groups being optionally interrupted or terminated by —O—, —S—, —NR$^6$— wherein R$^6$ is H or alkyl, or a combination thereof; and
optionally L additionally comprises a residue of a reactive group through which L is bounded to M;
M represents:
a reactive function selected from carboxylic acid, nitrile, ester, activated ester, aldehyde, acetal, ketone, ketal, alkyne, azide, alkene, diene, maleimide, protected maleimide, hydroxyl, phenol, 2-aminophenol, thiol, thioester, thioether, thiosulfonate, primary amine, secondary amine, tertiary amine, alkoxyamine, aniline, amide, phosphine, alkyl phosphate, isocyanates, isothiocyanates, hydrazide, hydrazine, tosylate ester, vinyl sulfone, carbamate, carbonate ester, 4-phenyl-1,2,4-triazole-3,5-dione, sulphide, azidoalkyl and azidoaryl; or
a bioactive group selected from amino acid, biogenic amine, peptide, heteropeptide, protein, antibody or fragment thereof, monobody, affibody, antibody construct, saccharide, polysaccharide, benzylguanine, biotin, avidin, nucleotide, oligonucleotide, microRNA, hapten, aptamer, ligand, enzyme, enzyme substrate, steroid, hormone, porphyrin, neurotransmitters, sympatomimetic drug, vitamin, phosphonate, nanocarrier, liposome, dendrimer, carbon nanotube and combinations thereof;
said aryl or heteroaryl being optionally further substituted by one or more substituents selected from hydroxyl; linear, cyclic or branched alkyl comprising 1, 2, 3, 4, 5 or 6 carbon atoms; aryl; heteroaryl; heterocyclyl; arylheterocyclyl; alkoxy; halogen; nitro; cyano; azido; aldehyde; boronato; phenyl; CF$_3$; —CH(OH) (CF$_3$); —CH(OCH$_2$OCH$_3$) (CF$_3$); methylenedioxy; ethylenedioxy; SO$_2$NRR', NRR', COOR, CONRR', NRCOR' wherein R and R' are each independently selected from the group consisting of H, alkyl, cycloalkyl, alkenyl, cycloalkenyl, alkynyl, cycloalkynyl and aryl;
said process comprising:
performing a halodemetallation by reacting an electrophilic reactant comprising halogen Y*, with a compound of formula (I) according to claim 1, to form compound of formula (II).

7. The process according to claim 6, wherein the halogen Y* is a radiohalogen.

8. The process according to claim 6, wherein in compound (II), M represents a reactive function, comprising a subsequent step of reacting compound (II) with a vector selected from amino acid, biogenic amine, peptide, heteropeptide, protein, antibody or fragment thereof, monobody, affibody, antibody construct, saccharide, polysaccharide, benzylguanine, biotin, avidin, nucleotide, oligonucleotide, microRNA, hapten, aptamer, ligand, enzyme, enzyme substrate, steroid, hormone, porphyrin, neurotransmitters, sympatomimetic drug, vitamin, phosphonate, nanocarrier, liposome, dendrimer, carbon nanotube; said vector comprising at least one reactive function B; said reactive function B being able to react with the reactive function of compound (II), leading to the labeled vector (III).

9. A device for implementing the labeling process according to claim 6, comprising at least one automaton of synthesis comprising:
   controlling means;
   a vacuum system;
   one reaction vessel;
   a purification cartridge;
   at least one line connected at one end to the reaction vessel and at the other end to a storage vessel, said storage vessel comprising a compound of formula (I);
   at least one line connected at one end to the reaction vessel and at the other end to a storage vessel, said storage vessel containing an electrophilic reactant comprising halogen Y*, or directly connected at the other end to an arrival of an electrophilic reactant comprising halogen Y* or a precursor thereof (distillation apparatus or production line);
   optionally at least one line connected at one end to the reaction vessel and at the other end to a storage vessel, said storage vessel comprising an oxidizing agent;
   at least one line connected at one end to the reaction vessel and at the other end to the top of the purification cartridge;
   at least one output line connected at one end to the bottom end of the purification cartridge, the other end enabling to recover compound (II) as previously defined;
   optionally a line connected to an inert gas arrival.

10. The device according to claim 9, further comprising a second automaton comprising:
   controlling means;
   a vacuum system;
   one reaction vessel;
   a purification cartridge;
   at least one input line connected at one end to the output line of the first automaton and at the other end to the reaction vessel to introduce compound (II) as previously defined, in the second automaton;
   at least one line connected at one end to the reaction vessel and at the other end to a storage vessel, said storage vessel comprising a vector selected from amino acid, biogenic amine, peptide, heteropeptide, protein, antibody or fragment thereof, monobody, affibody, antibody construct, saccharide, polysaccharide, benzylguanine, biotin, avidin, nucleotide, oligonucleotide, microRNA, hapten, aptamer, ligand, enzyme, enzyme substrate, steroid, hormone, porphyrin, neurotransmitters, sympatomimetic drug, vitamin, phosphonate, nanocarrier, liposome, dendrimer, carbon nanotube; said vector comprising at least one reactive function B; said reactive function B being able to react with the reactive function of compound (II), leading to the labeled vector (III);
   at least one line connected at one end to the reaction vessel and at the other end to a storage vessel, said storage vessel comprising an aqueous solvent;
   at least one line connected at one end to the reaction vessel and at the other end to the top of the purification cartridge;
   at least one line connected at one end to the bottom end of the purification cartridge, the other end enabling to recover compound (III") as previously defined;
   optionally a line connected to an inert gas arrival.

11. A kit comprising a compound of formula (I) according to claim 1.

12. The kit according to claim 11, further comprising an oxidizing agent.

13. The kit according to claim 11, further comprising a selectfluor, acetate or triflate salt.

14. The kit according to claim 11, further comprising a metallic catalyst.

15. The kit according to claim 11, further comprising a reducing agent.

16. The compound according to claim 1, wherein $X^-$ represents an anion selected from halide, acetate, trifluoroacetate, triflate (Tf), $NTf_2^-$, alkylsulfate, sulfonate, tetrafluoroborate ($BF_4^-$), tetraarylborate, hexafluorophosphate ($PF_6^-$), $NO_3^-$, $SbF_6^-$, prolinate, hydroxide, hydrogen sulfate, tetrachloroferrate, aluminum tetrachloride, perfluorobutylsulfonate, p-toluenesulfonate, formiate and dihydrogen phosphate.

17. The process according to claim 7, the radiohalogen is selected from $^{125}I$, $^{131}I$, $^{124}I$, $^{123}I$, $^{211}At$, $^{76}Br$ and $^{18}F$.

18. The kit according to claim 12, wherein the oxidizing agent is selected from N-chlorosuccinimide, N-iodosuccinimide, N-Bromosuccinimide, Chloramine-T, hydrogen peroxide, sodium hypochlorite, terbutylhydroperoxyde and potassium dichromate.

19. The kit according to claim 15, wherein the reducing agent is selected from sodium metabisulfite, sodium sulfite, cysteine and dithiothreitol.

* * * * *